United States Patent
Iwuagwu et al.

(10) Patent No.: US 11,919,897 B2
(45) Date of Patent: Mar. 5, 2024

(54) INHIBITORS OF HUMAN IMMUNODEFICIENCY VIRUS REPLICATION

(71) Applicant: VIIV HEALTHCARE UK (No. 5) LIMITED, Middlesex (GB)

(72) Inventors: Christiana Iwuagwu, Branford, CT (US); Kevin M Peese, Branford, CT (US)

(73) Assignee: VIIV HEALTHCARE UK (No. 5) LIMITED, Stevenage (GB)

( * ) Notice: Subject to any disclaimer, the term of this patent is extended or adjusted under 35 U.S.C. 154(b) by 539 days.

(21) Appl. No.: 17/273,748

(22) PCT Filed: Sep. 17, 2019

(86) PCT No.: PCT/IB2019/057814
§ 371 (c)(1),
(2) Date: Mar. 5, 2021

(87) PCT Pub. No.: WO2020/058844
PCT Pub. Date: Mar. 26, 2020

(65) Prior Publication Data
US 2021/0323961 A1  Oct. 21, 2021

Related U.S. Application Data

(60) Provisional application No. 62/733,692, filed on Sep. 20, 2018.

(51) Int. Cl.
C07D 471/04 (2006.01)
A61P 31/18 (2006.01)
A61K 45/06 (2006.01)

(52) U.S. Cl.
CPC .......... *C07D 471/04* (2013.01); *A61K 45/06* (2013.01); *A61P 31/18* (2018.01)

(58) Field of Classification Search
CPC ................................................... C07D 471/04
See application file for complete search history.

(56) References Cited

FOREIGN PATENT DOCUMENTS

WO  2016/033243 A1  3/2016
WO  2018/203235 A1  11/2018

OTHER PUBLICATIONS

Ziwen Wang, et al: Design, syntheses and antiviral activity of novel quinazolinones, European J. of Med. Chem, Elsevier, Amsterdam, NL vol. 53, Apr. 7, 2012 pp. 275-282.

*Primary Examiner* — Shawquia Jackson
(74) *Attorney, Agent, or Firm* — Nora L. Stein

(57) ABSTRACT

Compounds of Formula I, including pharmaceutically acceptable salts thereof, and compositions and methods for treating human immunodeficiency virus (HIV) infection are set forth:

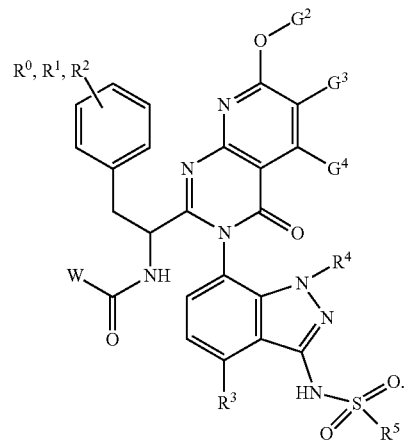

Formula I

25 Claims, No Drawings

INHIBITORS OF HUMAN IMMUNODEFICIENCY VIRUS REPLICATION

This application is a § 371 of International Application No. PCT/IB2019/057814, filed 17 Sep. 2019, which claims the benefit of U.S. Provisional Application No. 62/733,692, filed 20 Sep. 2018.

FIELD OF THE INVENTION

The invention relates to compounds, compositions, and methods for the treatment of human immunodeficiency virus (HIV) infection. More particularly, the invention provides novel inhibitors of HIV, pharmaceutical compositions containing such compounds, and methods for using these compounds in the treatment of HIV infection. The invention also relates to methods for making the compounds hereinafter described.

BACKGROUND OF THE INVENTION

Acquired immunodeficiency syndrome (AIDS) is the result of infection by HIV. HIV continues to be a major global public health issue. In 2015, an estimated 36.7 million people were living with HIV (including 1.8 million children)—a global HIV prevalence of 0.8%. The clear majority of this number live in low- and middle-income countries. In the same year, 1.1 million people died of AIDS-related illnesses.

Current therapy for HIV-infected individuals consists of a combination of approved anti-retroviral agents. Close to four dozen drugs are currently approved for HIV infection, either as single agents, fixed dose combinations or single tablet regimens; the latter two containing 2-4 approved agents. These agents belong to several different classes, targeting either a viral enzyme or the function of a viral protein during the virus replication cycle. Thus, agents are classified as either nucleotide reverse transcriptase inhibitors (NRTIs), non-nucleotide reverse transcriptase inhibitors (NNRTIs), protease inhibitors (PIs), integrase strand transfer inhibitors (INSTIs), or entry inhibitors (one, maraviroc, targets the host CCR5 protein, while the other, enfuvirtide, is a peptide that targets the gp41 region of the viral gp160 protein). In addition, a pharmacokinetic enhancer (cobicistat or ritonavir) can be used in combinations with antiretroviral agents (ARVs) that require boosting.

Despite the armamentarium of agents and drug combinations, there remains a medical need for new anti-retroviral agents. High viral heterogeneity, drug-associated toxicity, tolerability problems, and poor adherence can all lead to treatment failure and may result in the selection of viruses with mutations that confer resistance to one or more antiretroviral agents or even multiple drugs from an entire class (Beyrer, C., Pozniak A. HIV drug resistance—an emerging threat to epidemic control. N. Engl. J. Med. 2017, 377, 1605-1607; Gupta, R. K., Gregson J., et al. HIV-1 drug resistance before initiation or re-initiation of first-line antiretroviral therapy in low-income and middle-income countries: a systematic review and meta-regression analysis. Lancet Infect. Dis. 2017, 18, 346-355; Zazzi, M., Hu, H., Prosperi, M. The global burden of HIV-1 drug resistance in the past 20 years. Peer, J. 2018, DOI 10.7717/peerj.4848). As a result, new drugs are needed that are easier to take, have high genetic barriers to the development of resistance and have improved safety over current agents. In this panoply of choices, novel mechanisms of action (MOAs) that can be used as part of the preferred antiretroviral therapy (ART) can still have a major role to play since they should be effective against viruses resistant to current agents.

Certain potentially therapeutic compounds have now been described in the art and set forth in Blair, Wade S. et. al. Antimicrobial Agents and Chemotherapy (2009), 53(12), 5080-5087, Blair, Wade S. et al. PLoS Pathogens (2010), 6(12), e1001220, Thenin-Houssier, Suzie; Valente, Susana T. Current HIV Research, 2016, 14, 270-282, and PCT Patent applications with the following numbers: WO 2012065062, WO 2013006738, WO 2013006792, WO 2014110296, WO 2014110297, WO 2014110298, WO 2014134566, WO 2015130964, WO$_{2015130966}$, WO 2016033243, WO 2018035359, WO 2018203235, WO 2019161017, and WO 2019161280.

What is now needed in the art are additional compounds which are novel and useful in the treatment of HIV. Additionally, these compounds should provide advantages for pharmaceutical uses, for example, with regard to one or more of their mechanisms of action, binding, inhibition efficacy, target selectivity, solubility, safety profiles, bioavailability or reduced frequency of dosing. Also needed are new formulations and methods of treatment which utilize these compounds.

SUMMARY OF THE INVENTION

Briefly, in one aspect, the present invention discloses a compound of Formula I, or a pharmaceutically acceptable salt thereof:

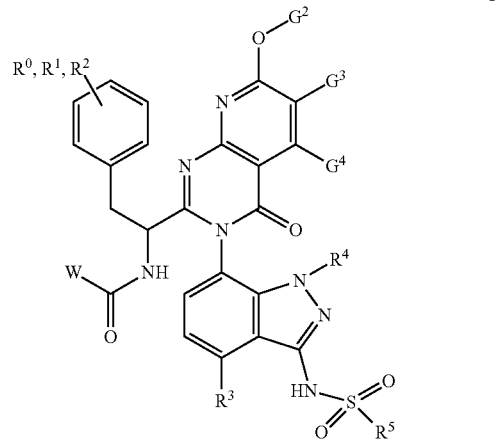

I wherein:
$R^0$, $R^1$, and $R^2$ are each independently hydrogen, Cl, F, —OMe, —CN, —$C_1$-$C_3$alkyl, or —$C_3$-$C_5$ cycloalkyl, wherein $C_1$-$C_3$ alkyl may be optionally substituted with from 1-3 fluorines;
$G^2$ is hydrogen, 6 membered aryl, 5-6 membered heteroaryl, —$C_6$-$C_8$ alkyl, —$C_3$-$C_7$ cycloalkyl, or —$C_1$-$C_3$ alkyl wherein —$C_1$-$C_3$ alkyl is substituted with $G^5$;
$G^3$ is hydrogen, methyl, fluoro, chloro, phenyl, O$C_1$-$C_3$ alkyl, or OPh;
$G^4$ is hydrogen, methyl, fluoro, chloro, phenyl, O$C_1$-$C_3$ alkyl, or OPh;
$G^5$ is —O$G^6$, —$C_3$-$C_7$ cycloalkyl, 6 membered aryl, 5 membered heteroaryl, 4-7 membered heterocycle, —C(O)N($G^7$)($G^8$), C(O)OH, —SO$_2$($G^7$), —N($G^7$)($G^8$), —SO$_2$-morpholine, C(O)-morpholine, or one of the following:

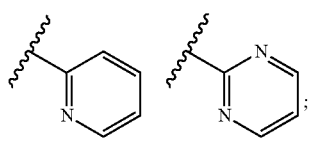

G⁶ is —$C_1$-$C_6$ alkyl, —$C_3$-$C_7$ cycloalkyl, 6 membered aryl, 5 membered heteroaryl, 4-7 membered heterocycle;

G⁷ is —$C_1$-$C_6$ alkyl or $C_3$-$C_6$ cycloalkyl;

G⁸ is —$C_1$-$C_6$ alkyl or $C_3$-$C_6$ cycloalkyl;

$R^3$ is hydrogen, Cl, or F;

$R^4$ is hydrogen, $C_1$-$C_3$ alkyl, or cyclopropyl wherein cyclopropyl or $C_1$-$C_3$ cycloalkyl is optionally substituted with 1-3 fluorines;

$R^5$ is $C_1$-$C_6$ alkyl, $C_3$-$C_6$ cycloalkyl, or N(G⁷)(G⁸);

W is selected from:

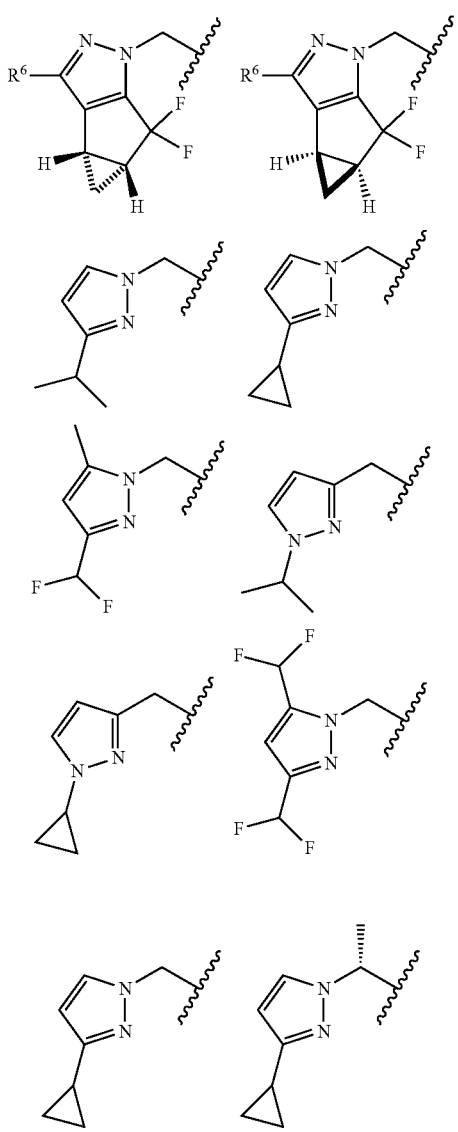

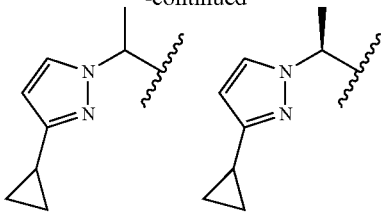

wherein $R^6$ is methyl optionally substituted with 1 to 3 fluorines.

In another aspect, the present invention discloses a pharmaceutical composition comprising a compound of Formula I or a pharmaceutically acceptable salt thereof.

In another aspect, the present invention discloses a method of treating HIV infection comprising administering a composition comprising a compound of Formula I or a pharmaceutically acceptable salt thereof to a patient.

In another aspect, the present invention discloses a compound of Formula (I) or pharmaceutically acceptable salt thereof for use in therapy.

In another aspect, the present invention discloses a compound of Formula (I) or pharmaceutically acceptable salt thereof for use in treating HIV infection.

In another aspect, the present invention discloses the use of a compound of Formula (I) or pharmaceutically acceptable salt thereof in the manufacture of a medicament for the treatment of HIV infection.

DETAILED DESCRIPTION OF THE EMBODIMENTS

In one embodiment $R^0$, $R^1$, and $R^2$ are positioned as shown below

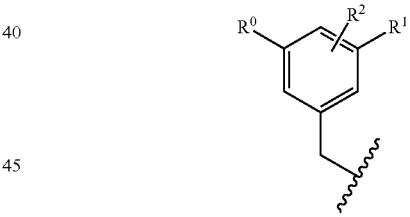

and $R^0$, $R^1$, and $R^2$ are each independently selected from hydrogen, Cl, F, —$OCH_3$, —CN, or —$CH_3$ with the proviso that substituents Cl, —OMe, and —$CH_3$ may not be used more than twice and substituent —CN may not be used more than once. In another embodiment, $R^0$, $R^1$, and $R^2$ are positioned as shown above and $R^0$, $R^1$, and $R^2$ are each independently selected from hydrogen, F, Cl or —$CH_3$ with the proviso that at least one of the groups $R^0$, $R^1$ and $R^2$ is hydrogen. In another embodiment, $R^0$, $R^1$, and $R^2$ are positioned as shown above and $R^0$ is fluorine, $R^1$ is fluorine, and $R^2$ is hydrogen.

In one embodiment, G³ and G⁴ are independently selected from hydrogen, methyl, fluoro, chloro, or O$C_1$-$C_2$ alkyl with the proviso that at least one of G³ and G⁴ must be hydrogen;

In one embodiment $R^3$ is hydrogen, Cl, or F; $R^4$ is hydrogen, $C_1$-$C_3$ alkyl, or cyclopropyl wherein $C_1$-$C_3$ alkyl is optionally substituted with 1-3 fluorines and cyclopropyl is optionally substituted with 1-2 fluorines; and $R^5$ is $C_1$-$C_3$ alkyl or $C_3$-$C_4$ cycloalkyl. In another embodiment $R^3$ is chloride, $R^4$ is methyl, 2,2-difluoroethyl, or 2,2,2-trifluoroethyl; and $R^5$ is methyl or cyclopropyl.

In one embodiment W is

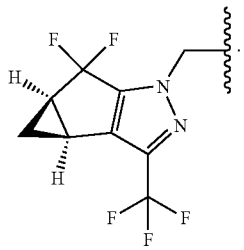

In another embodiment W is

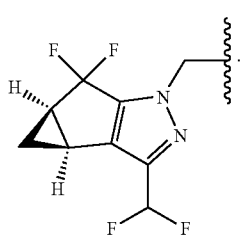

In another embodiment W is one of the following:

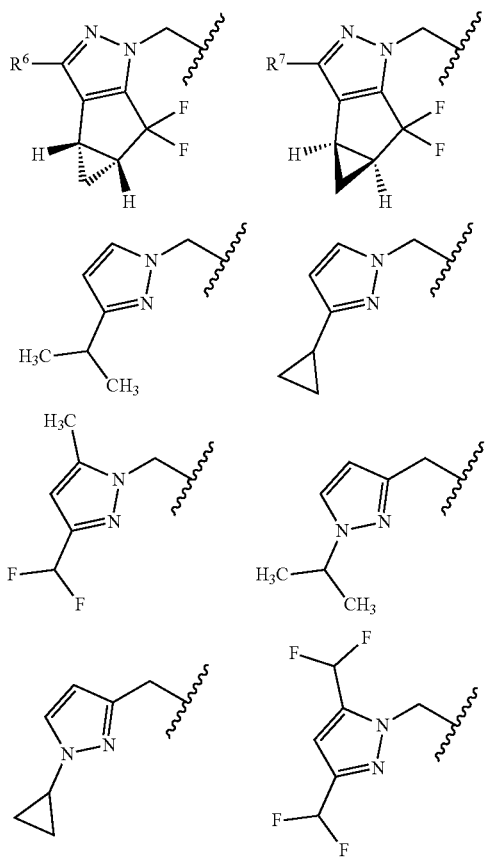

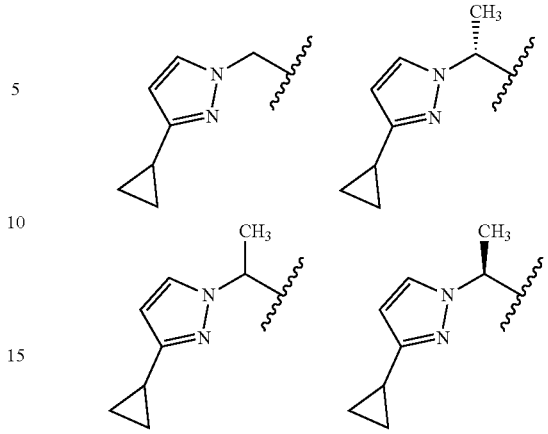

wherein $R^6$ is methyl optionally substituted with one fluorine and $R^7$ is methyl optionally substituted with 1 to 3 fluorines.

In one embodiment $G^2$ is hydrogen, —$C_6$-$C_8$ alkyl, or —$C_1$-$C_3$ alkyl wherein —$C_1$-$C_3$ alkyl is substituted with $G^5$; $G^5$ is —$OG^6$, —$C_3$-$C_6$ cycloalkyl, 6 membered aryl, 5 membered heteroaryl, 4-7 membered heterocycle, —C(O)N($G^7$)($G^8$), —$SO_2$($G^7$), —N($G^7$)($G^8$), —$SO_2$-morpholine, C(O)-morpholine, or one of the following:

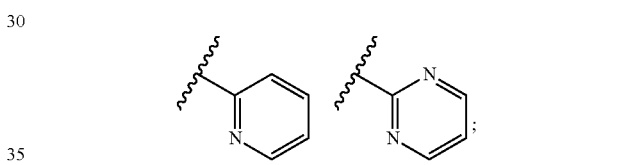

$G^7$ is —$C_1$-$C_3$ alkyl or $C_3$-$C_6$ cycloalkyl; and $G^8$ is —$C_1$-$C_3$ alkyl or $C_3$-$C_6$ cycloalkyl.

In another embodiment $G^2$ is one of the following:

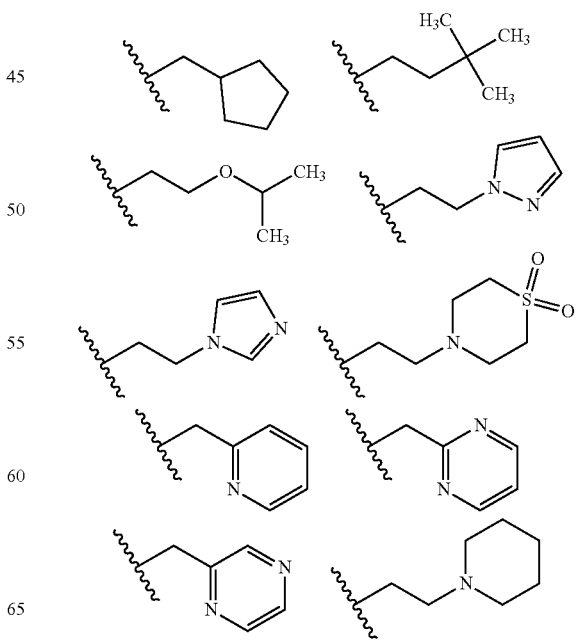

-continued
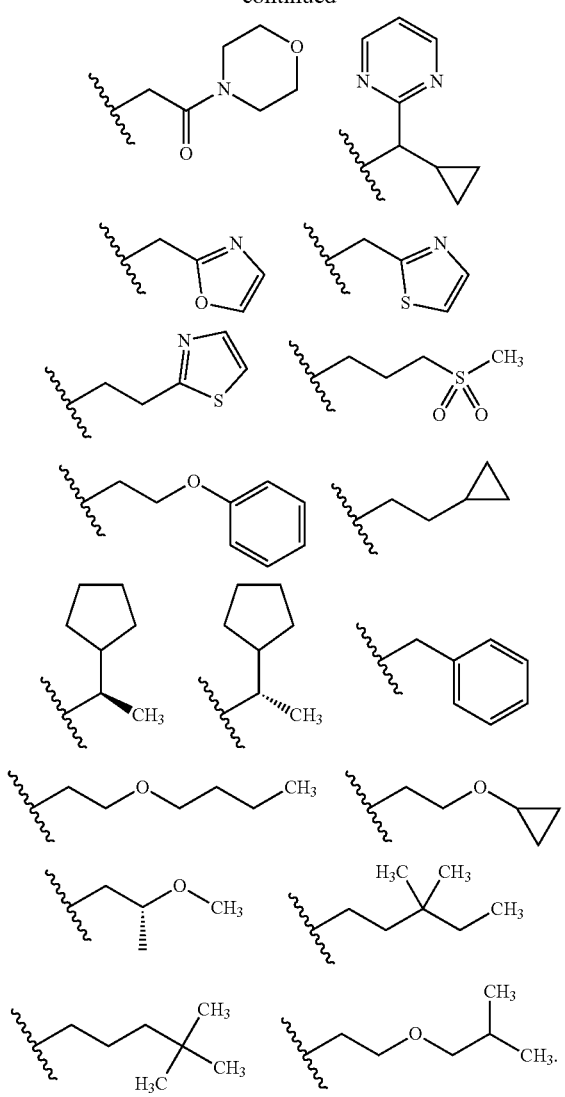
Preferably, the compounds and salts of this invention have the stereochemistry shown below
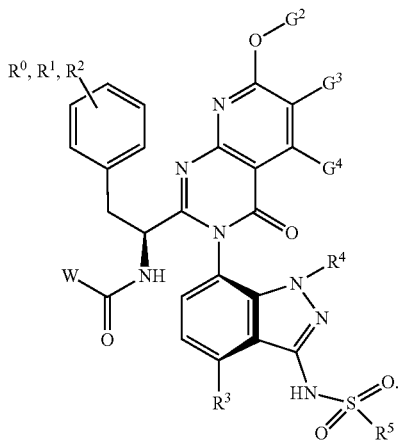
Preferred compounds and salts of this invention include:
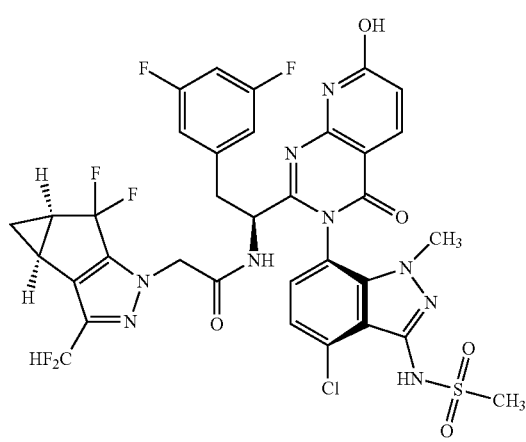
Preferably, the compounds and salts of this invention have the stereochemistry shown below
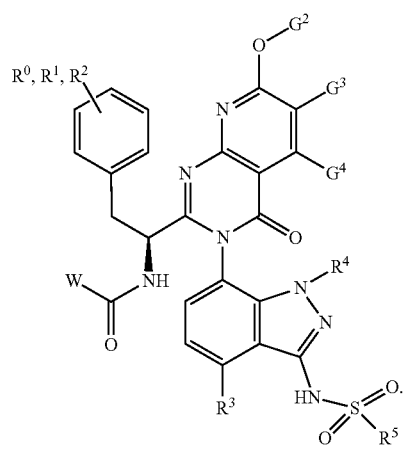
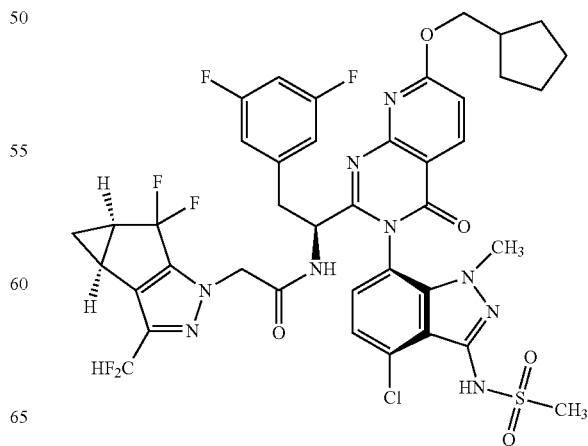

9
-continued
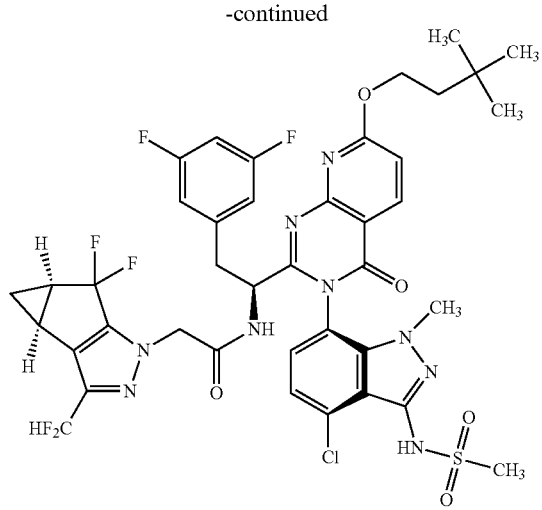
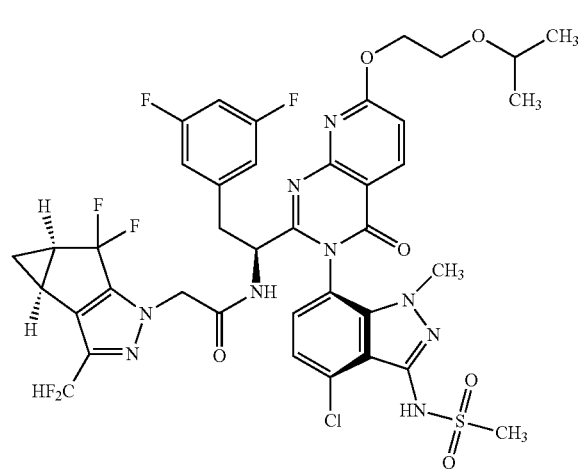
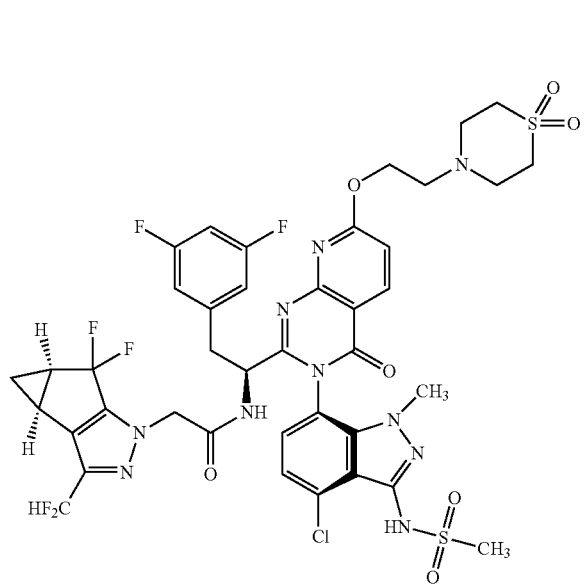
10
-continued
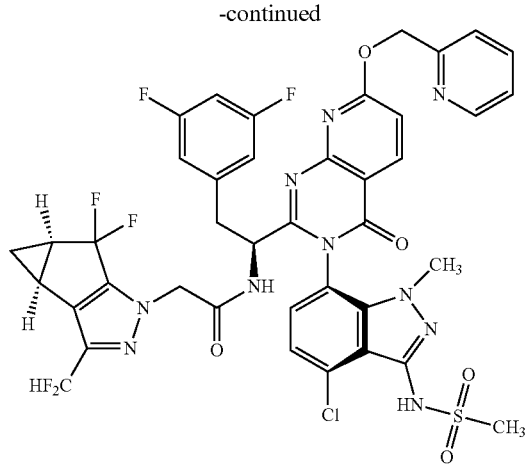
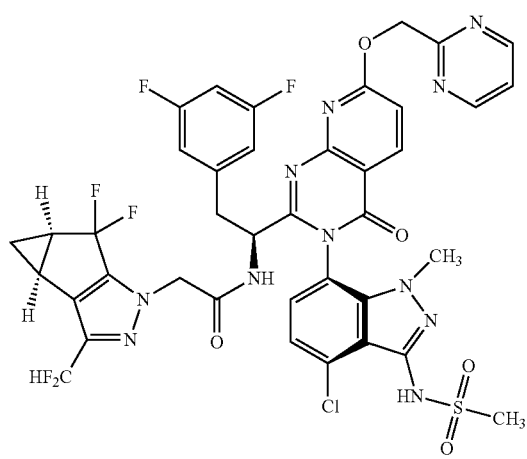
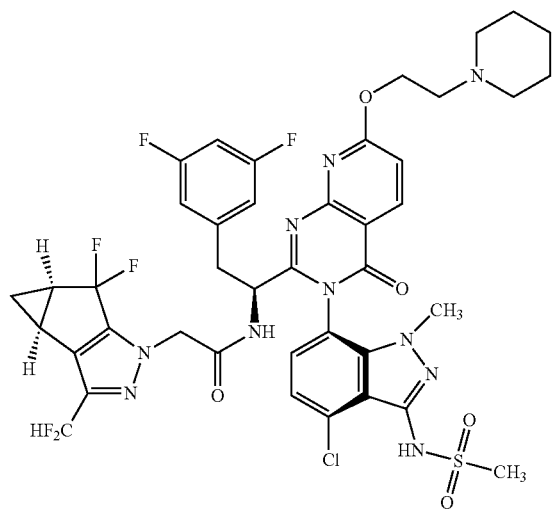
and pharmaceutically acceptable salts thereof.

Preferred compounds and salts of this invention include:
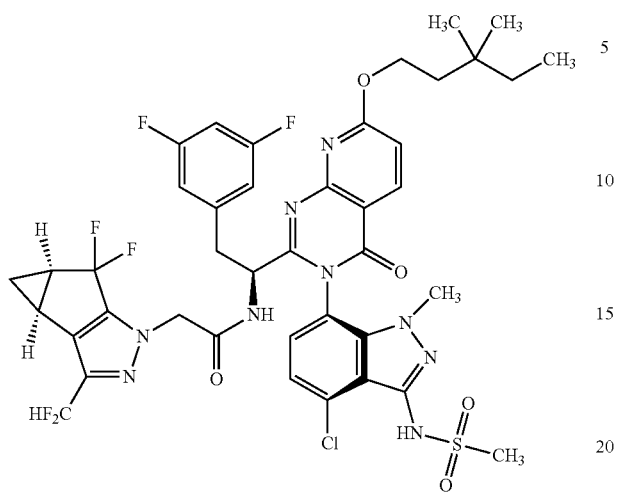
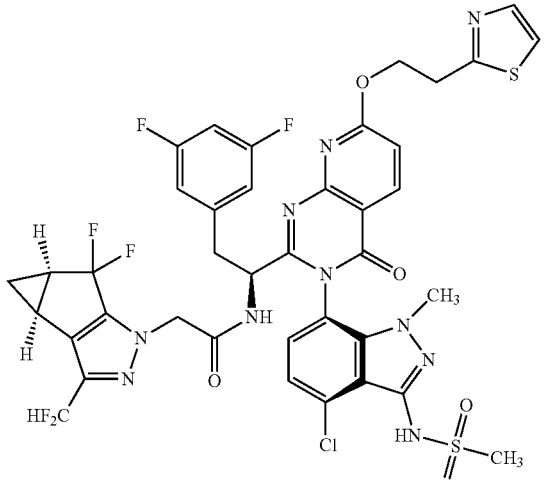
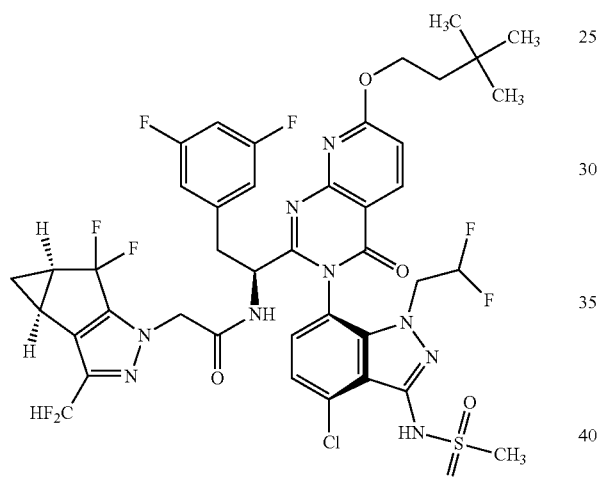
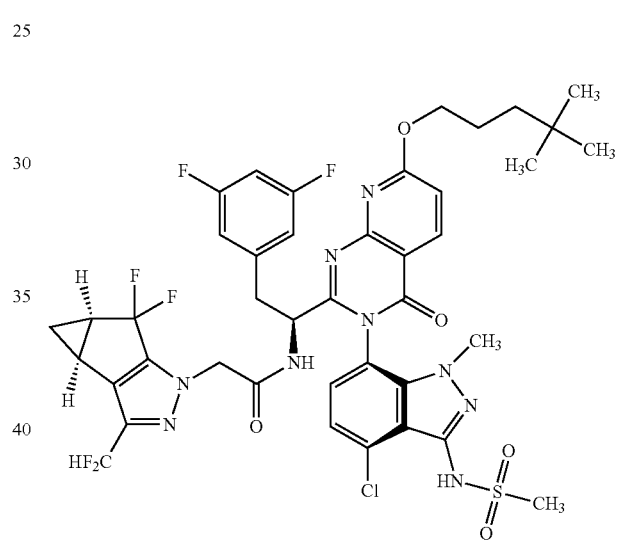
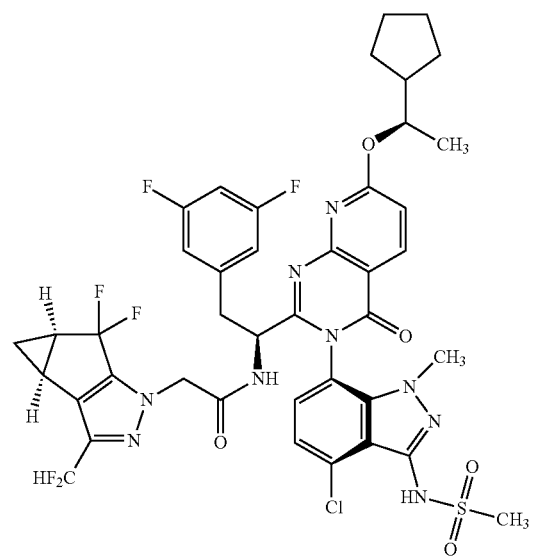
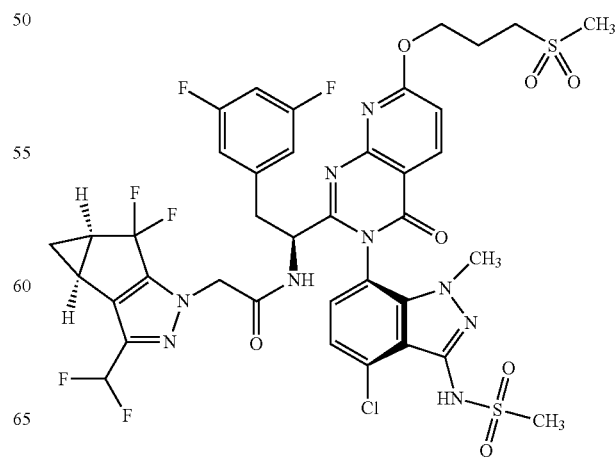

13
-continued
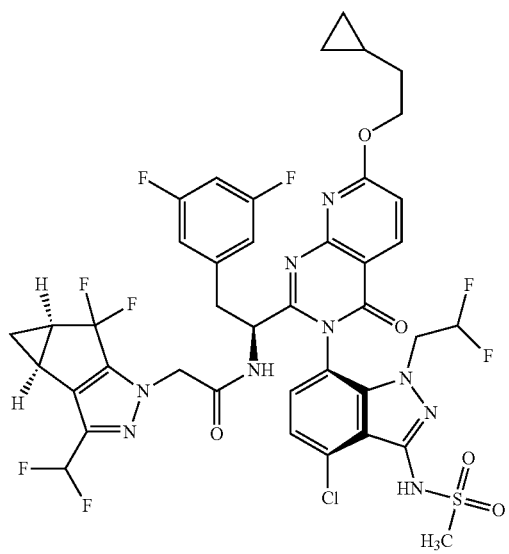
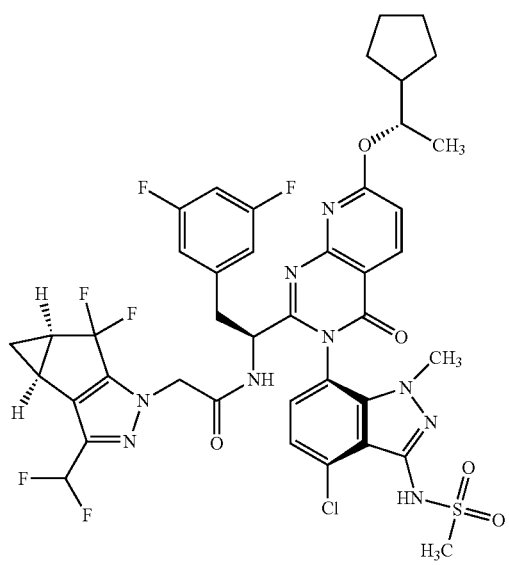
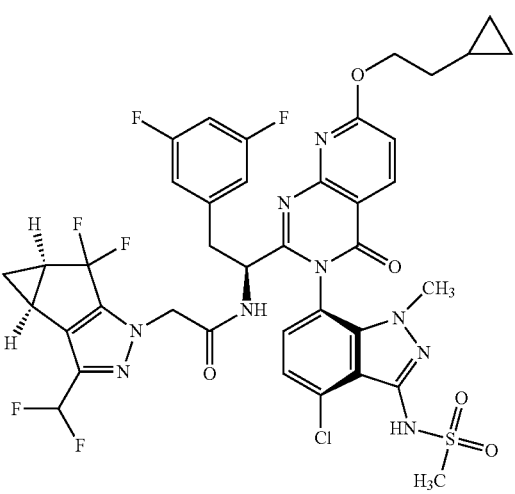
14
-continued
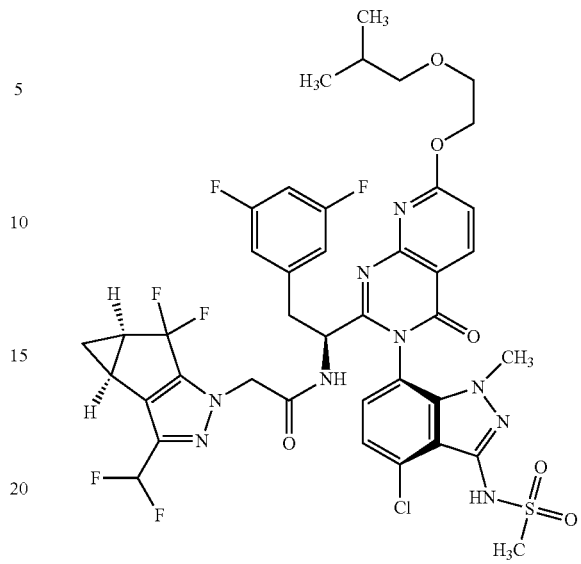
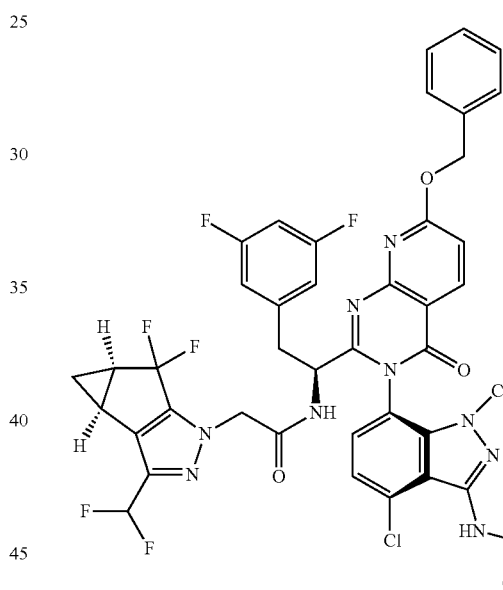
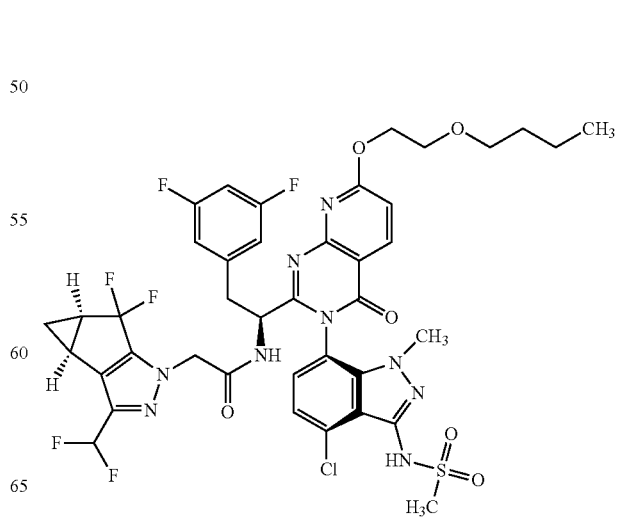

-continued

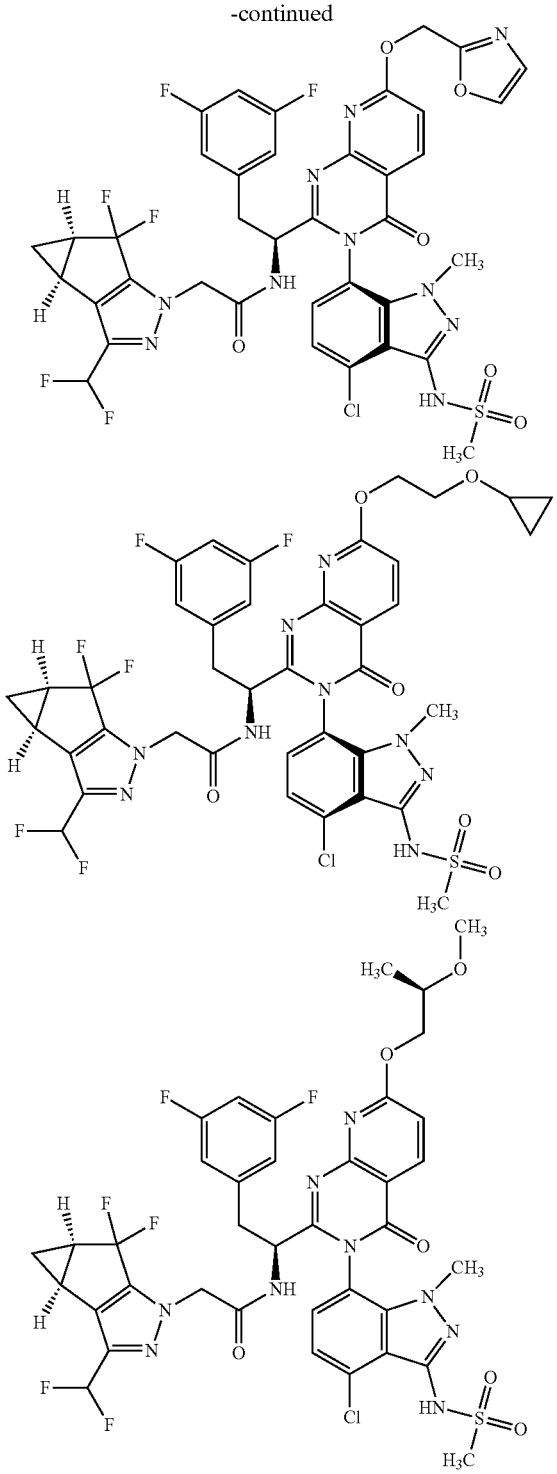

and pharmaceutically acceptable salts thereof.

The salts of compounds of formula (I) are pharmaceutically acceptable. Such salts may be acid addition salts or base addition salts; for a review of suitable pharmaceutically acceptable salts see Berge et al, J. Pharm. Sci., 66, 1-19, 1977. In an embodiment, acid addition salts are selected from the hydrochloride, hydrobromide, hydroiodide, sulphate, bisulfate, nitrate, phosphate, hydrogen phosphate, acetate, benzoate, succinate, saccharate, fumarate, maleate, lactate, citrate, tartrate, gluconate, camsylate, methane- sulfonate, ethanesulfonate, benzenesulfonate, p-toluene- sulfonate and pamoate. In an embodiment, base addition salts include metal salts (such as sodium, potassium, aluminium, calcium, magnesium and zinc) and ammonium salts (such as isopropylamine, diethylamine, diethanolamine salts). Other salts (such as trifluoroacetates and oxalates) may be used in the manufacture of compounds of formula (I) and their pharmaceutically acceptable salts and are included within the scope of the invention. All possible stoichiometric and non-stoichiometric forms of the salts of compounds of formula (I) are included within the scope of the invention. Acid and base addition salts may be prepared by the skilled chemist, by treating a compound of formula (I) with the appropriate acid or base in a suitable solvent, followed by crystallization and filtration.

Some of the compounds of the invention exist in stereoisomeric forms. The invention includes all stereoisomeric forms of the compounds including enantiomers and diastereomers including atropisomers. The term homochiral is used as a descriptor, per accepted convention, to describe a structure which is a single stereoisomer. Absolute stereochemistry was not assigned in all cases. Thus, the compound is drawn at the chiral center as unspecified but labelled as homochiral and in the procedures it is identified by its properties such as for example first eluting off a normal or chiral column per the conventions of chemists. It should be noted that the provided experimental procedures teach how to make the exact compound even if not drawn with absolute configuration. Methods of making and separating stereoisomers are known in the art. The invention includes all tautomeric forms of the compounds. The invention includes atropisomers and rotational isomers.

For the compounds of Formula I, the scope of any instance of a variable substituent can be used independently with the scope of any other instance of a variable substituent. As such, the invention includes combinations of the different aspects. In some examples, the stereochemistry of all the centers were not unambiguously assigned so they can be referred to as diastereomer 1 and diastereomer 2 or enantiomer 1 or enantiomer 2 etc. and these are understood by chemists skilled in the art. In other cases, atropisomers can be observed and these are understood to convert at slow or fast rates or even not at all depending on the conditions for handling the compound. These are referred to as mixtures of atropisomers where they interconvert at ambient temperatures or as atropisomer 1 and atropisomer 2 where they were isolated. Since the compounds are identified by their properties rather than exact structural assignment from a crystal structure, it is understood in the art that where not specified, atropisomers are covered and inferred to be covered by the chemical structure.

In the method of this invention, preferred routes of administration are oral and by injection to deliver subcutaneously. Therefore, preferred pharmaceutical compositions are those compositions suitable for these routes of administration, for example tablets or injectable compositions.

The compounds of this invention are believed to act as Capsid Inhibitors.

The compounds of the present invention and their salts, solvates, or other pharmaceutically acceptable derivatives thereof, may be employed alone or in combination with other therapeutic agents. The compounds of the present invention and any other pharmaceutically active agent(s) may be administered together or separately and, when administered separately, administration may occur simultaneously or sequentially, in any order. The amounts of the compounds of the present invention and the other pharmaceutically active agent(s) and the relative timings of administration will be selected to achieve the desired combined therapeutic effect. The administration in combination of a compound of the present invention and salts, solvates, or other pharmaceutically acceptable derivatives thereof with other treatment agents may be in combination by administration concomitantly in: (1) a unitary pharmaceutical composition including multiple compounds; or (2) separate pharmaceutical compositions each including one of the compounds. Alternatively, the combination may be administered separately in a sequential manner wherein one treatment agent is administered first and the other second or vice versa, and the different agents could be administered on different schedules if appropriate. Such sequential administration may be close in time or remote in time. The amounts of the compound(s) of Formulas I, II, or III or salts thereof and the other pharmaceutically active agent(s) and the relative timings of administration will be selected to achieve the desired combined therapeutic effect.

As such, the compounds of the present invention may be used in combination with one or more agents useful in the prevention or treatment of HIV.

EXAMPLES

The compounds of the invention according to the various embodiments can be made by various methods available in the art, including those of the following schemes in the specific examples which follow. The structure numbering and variable numbering shown in the synthetic schemes may be distinct from, and should not be confused with, the structure or variable numbering in the claims or the rest of the specification. The variables in the schemes are meant only to illustrate how to make some of the compounds of the invention.

Abbreviations used in the schemes generally follow conventions used in the art. Some specific chemical abbreviations used in the examples are defined as follows: "DMF" for N,N-dimethylformamide; "MeOH" for methanol; "Ar" for aryl; "TFA" for trifluoroacetic acid; "BOC" for t-butoxycarbonate, "DMSO" for dimethylsulfoxide; "h" for hours; "rt" for room temperature or retention time (context will dictate); "min" for minutes; "EtOAc" for ethyl acetate; "THF" for tetrahydrofuran; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HATU" for (1-[Bis(dimethylamino)methylene]-1H-1,2,3-triazolo[4,5-b]pyridinium 3-oxid hexafluorophosphate) "DIEA" for diisopropylethylamine.

Certain other abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "1H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

The following examples are provided by way of illustration only and should not be construed as limiting the scope of the invention. Table 1 presents additional compounds of the invention prepared using similar methods. Absolute stereochemistry was not determined in all instances. In the examples where absolute stereochemistry has not been assigned, isomers or slowly interconverting atropisomers that were separated by chiral or other chromatography are labelled as "First", "Second", etc. as per their order of elution from the column.

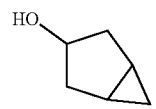

Bicyclo[3.1.0]hexan-3-ol

To a stirred solution of cyclopent-3-enol (130 g, 1545 mmol) in DCM (1200 mL), was added Diethyl zinc (1.0 M in Hexane, 3091 mL, 3091 mmol) drop wise at 0-5° C. over a period of 3 h followed by drop wise addition of Diiodomethane (249 mL, 3091 mmol) in DCM (300 mL) over a period of 1 h at 0° C. Reaction mixture was allowed to warm to 27° C. (Note: white precipitation was observed) and stirred for 16 h under N2 atmosphere. Progress of the reaction was monitored by TLC (SiO$_2$, 20% EtOAc/pet, Rf=0.3, UV-inactive, PMA-active). After completion, the reaction mixture was quenched with aq saturated NH$_4$Cl solution (1.5 L) and filtered through celite bed. The aqueous layer was extracted with DCM (2× 1000 mL). The combined organic layers were dried over anhydrous Na$_2$SO$_4$, filtered and the filtrate was concentrated under reduced pressure to afford crude bicyclo[3.1.0]hexan-3-ol (180 g, Yield: Crude) as reddish liquid. $^1$H NMR (400 MHz, CHLOROFORM-d) δ=4.41-4.35 (m, 1H), 2.18-2.05 (m, 2H), 1.73 (d, J=13.9 Hz, 2H), 1.35-1.25 (m, 2H), 1.21-1.14 (m, 1H), 0.57-0.43 (m, 2H). GCMS: m/z=98.1).

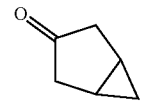

Bicyclo[3.1.0]hexan-3-one

To a stirred solution of bicyclo[3.1.0]hexan-3-ol (210 g, 2054 mmol) in DCM (5000 mL), was added Dess-martin periodinane (954 g, 2249 mmol) portion wise at 0° C. and allowed to warm to 27° C. under N2 atmosphere and stirred for 16 h. Progress of the reaction was monitored by TLC (SiO$_2$, 20% Acetone/Hex, Rf=0.3, UV in-active, PMA-active). After completion, the reaction mixture was filtered through celite bed and the filtrate was washed with 1N NaOH solution (8×1000 mL) and extracted with DCM (5×1000 mL). The combined organic layers were dried over anhydrous Na$_2$SO$_4$ and filtered. The filtrate was concentrated under reduced pressure (Bath temperature: 20° C.) to get crude compound as brown liquid which was purified by downward distillation at 70° C. to afford bicyclo[3.1.0]hexan-3-one (125 g, Yield: 62%, Pale yellow viscous liquid. ¹H NMR (400 MHz, CHLOROFORM-d) δ=2.61-2.54 (m, 2H), 2.17-2.12 (m, 2H), 1.54-1.46 (m, 2H), 0.92-0.86 (m, 1H), −0.01-0.08 (m, 1H), GCMS: M/Z=96.1).

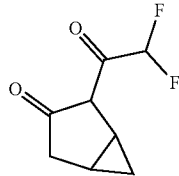 [SMILES: O=C1CC2CC2C1C(=O)C(F)F]

2-(2,2-difluoroacetyl)bicyclo[3.1.0]hexan-3-one

To a stirred solution of bicyclo[3.1.0]hexan-3-one (125 g, 1274 mmol) in THF (1500 mL), was added LDA (2.0 M in THF, 0.701 L, 1402 mmol) at −78° C. under N₂ atmosphere and stirred for 1 h followed by the addition Ethyldifluoroacetate (174 g, 1402 mmol) in THF (300 mL) slowly at −78° C. for 30 min. After the addition the reaction mixture was allowed to warm to 27° C. and stirred for 1 h under N2 atmosphere. Progress of the reaction was monitored by TLC (SiO₂, 20% Acetone/Hexane, Rf=0.3, UV-active). After completion, the reaction mixture was quenched with 1N HCl (2000 mL) and stirred for 30 min and extracted with EtOAc (3×1000 mL). The combined organic layers were washed with brine (1000 mL), dried over anhydrous Na₂SO₄ and filtered. The filtrate was concentrated under reduced pressure to afford 2-(2,2-difluoroacetyl)bicyclo[3.1.0]hexan-3-one (180 g, Yield: 71.2%, pale yellow viscous liquid. ¹H NMR (400 MHz, CHLOROFORM-d) δ=6.18 (t, J=54.8 Hz, 1H), 2.70-2.62 (m, 1H), 2.35 (d, J=19.4 Hz, 1H), 2.14 (br s, 1H), 1.26-1.21 (m, 1H), 1.04-1.03 (m, 1H), 0.22-0.21 (m, 1H), LCMS: M/Z=173.17).

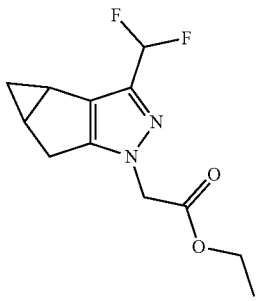 [SMILES: CCOC(=O)Cn1nc(C(F)F)c2c1CC1CC21]

Ethyl 2-(3-(difluoromethyl)-3b,4,4a,5-tetrahydro-1H-cyclopropa[3,4]cyclopenta[1,2-c]pyrazol-1-yl)acetate To a stirred solution of 2-(2,2-difluoroacetyl)bicyclo[3.1.0]hexan-3-one (180 g, 910 mmol) in Ethanol (2 L), was added ethyl 2-hydrazinylacetate hydrochloride (422 g, 2729 mmol) followed by the addition of sulfuric acid (20 mL, 375 mmol) at 27° C. under N2 atmosphere and stirred for 30 min. The reaction mixture was further heated to 100° C. and stirred for 16 h. Progress of the reaction was monitored by TLC (SiO₂, 20% Acetone/Hexane, Rf=0.3, UV-active). After completion, the reaction mixture was evaporated under reduced pressure, the residue was dissolved in EtOAc (2000 mL) and washed with water (2×1 L), brine (1.0 L), dried over anhydrous Na₂SO₄ and filtered. The filtrate was concentrated under reduced pressure to obtain crude (N66158-21-A1, 440 g). The above crude compound was purified by column chromatography (silica gel: 100-200 mesh) with 0-2% Acetone/Pet as eluent. The fractions containing product were collected and concentrated under reduced pressure to afford ethyl2-(3-(difluoromethyl)-3b,4,4a,5-tetrahydro-1H-cyclopropa[3,4]cyclopenta[1,2-c]pyrazol-1-yl)acetate (110 g, Yield: 46.4%, as an off white solid. ¹H NMR (400 MHz, DMSO-d₆) δ=6.86 (t, J=54.8 Hz, 1H), 4.93 (s, 2H), 4.14 (q, J=7.2 Hz, 2H), 2.88-2.79 (m, 1H), 2.76-2.68 (m, 1H), 2.14-2.04 (m, 2H), 1.19 (t, J=7.2 Hz, 3H), 1.10-1.03 (m, 1H), 0.14 (q, J=4.3 Hz, 1H). LCMS M+H=257.13.

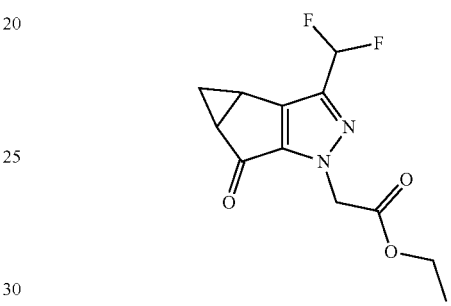

Ethyl 2-(3-(difluoromethyl)-5-oxo-3b,4,4a,5-tetrahydro-1H-cyclopropa[3,4]cyclopenta[1,2-c]pyrazol-1-yl)acetate To a stirred solution of ethyl 2-(3-(difluoromethyl)-3b,4,4a,5-tetrahydro-1H-cyclopropa[3,4]cyclopenta[1,2-c]pyrazol-1-yl)acetate (110 g, 422 mmol) and celite (395 g) in Cyclohexane (3.5 L) at 0° C., pyridinium dichromate (794 g, 2110 mmol) was added portion wise followed by the addition of tert-butyl hydro peroxide (355 mL, 2130 mmol) drop wise over a period of 10 min under N2 atmosphere. The reaction mixture was warmed to 27° C. and stirred for 48 h. Progress of the reaction was monitored by TLC (SiO₂, 30% Acetone/pet, Rf=0.4, UV-active). After completion, the reaction mixture was filtered and washed with EtOAc (1000 mL). The organic layer was washed with saturated aq. Na₂S₂O₃ (2×500 ml), saturated FeSO₄ (300 ml) and brine (500 ml). The organic layer was dried over anhydrous Na₂SO₄, filtered and evaporated under reduced pressure to obtain crude compound (150 g).

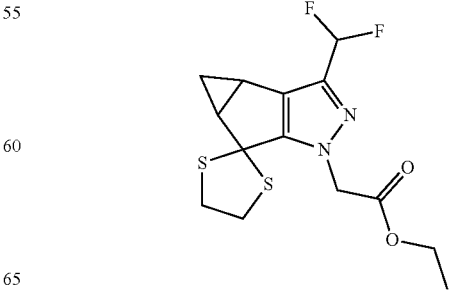

Ethyl 2-(3-(difluoromethyl)-4,4a-dihydrospiro[cyclopropa[3,4]cyclopenta[1,2-c]pyrazole-5,2'-[1,3]dithiolane]-1(3bH)-yl)acetate To a stirred solution of ethyl 2-(3-(difluoromethyl)-5-oxo-3b,4,4a,5-tetrahydro-1H-cyclopropa[3,4]cyclopenta[1,2-c]pyrazol-1-yl)acetate (75 g, 269 mmol) in DCM (1500 mL), was added ethane-1,2-dithiol (43.0 mL, 511 mmol) and followed by the addition of Boron trifluoride acetic acid (72.6 mL, 511 mmol) at 27° C. under Nz atmosphere and stirred for 16 h at 27° C. Progress of the reaction was monitored by TLC (SiO$_2$, 20% Acetone/Pet, Rf=0.35, UV-Active). After completion, the reaction mixture was cooled to 0° C. and neutralized with saturated NaHCO$_3$ (500 mL) and extracted with DCM (2×1000 mL). The combined organics were washed with brine (1000 mL), dried over anhydrous Na$_2$SO$_4$, filtered and evaporated under reduced pressure to obtain crude N66187-25-A1 as brown liquid. The above crude was purified by column chromatography using silica gel (100-200 mesh) with 5-10% EtOAc/Pet as eluent. The fractions containing product were collected and concentrated under reduced pressure to afford ethyl 2-(3-(difluoromethyl)-4,4a-dihydrospiro[cyclopropa[3,4]cyclopenta[1,2-c]pyrazole-5,2'-[1,3]dithiolane]-1(3bH)-yl)acetate (80 g, Yield:74.0%) as an Off-white solid. $^1$H NMR (400 MHz, CHLOROFORM-d) δ=6.61 (t, J=55.2 Hz, 1H), 5.00-4.85 (m, 2H), 4.29-4.19 (m, 2H), 3.55-3.46 (m, 4H), 2.63-2.53 (m, 1H), 2.49-2.38 (m, 1H), 1.30-1.24 (m, 4H), 0.65-0.60 (m, 1H). LCMS M+H=346.9.

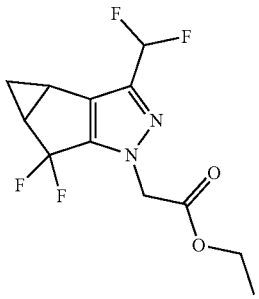 [SMILES: CCOC(=O)Cn1nc(C(F)F)c2c1C(F)(F)C1CC21]

Ethyl 2-(3-(difluoromethyl)-5,5-difluoro-3b,4,4a,5-tetrahydro-1H-cyclopropa[3,4]cyclopenta[1,2-c]pyrazol-1-yl)acetate To a stirred solution of 1,3-dibromo-5,5-dimethylimidazolidine-2,4-dione (26.3 g, 92 mmol) in DCM (20 mL) was added HF-pyridine (2.460 g, 24.83 mmol) at −70° C. under N2 atmosphere and stirred for 30 min followed by the addition of ethyl 2-(3-(difluoromethyl)-4,4a-dihydrospiro[cyclopropa[3,4]cyclopenta[1,2-c]pyrazole-5,2'-1,3]dithiolane]-1(3bH)-yl)acetate (10 g 24.83 mmol) in DCM (20 mL) at the same temperature. The reaction mixture was allowed to warm to −40° C. and stirred for 1 h. Progress of the reaction was monitored by TLC (SiO$_2$, 30% EtOAc/Pet, Rf=0.3, UV in-active). After completion, the reaction mixture was neutralized with sat. NaHCO$_3$ (200 mL) and extracted with EtOAc (2×100 mL) at 27° C. The combined organics were washed with brine (50 ml), dried over anhydrous Na$_2$SO$_4$, filtered and evaporated under reduced pressure to get crude (15 g) as brown gum. The above crude compound was purified by column chromatography using silica gel (100-200 mesh) with 0-25% EtOAc/Pet as eluent. The fractions containing product were collected and concentrated under reduced pressure to afford ethyl 2-(3-(difluoromethyl)-5,5-difluoro-3b,4,4a,5-tetrahydro-1H-cyclopropa[3,4]cyclopenta[1,2-c]pyrazol-1-yl)acetate (8.5 g, Yield: 91%) as a pale-yellow solid. $^1$H NMR (400 MHz, CHLOROFORM-d) δ=6.62 (t, J=55.2 Hz, 1H), 4.82 (s, 2H), 4.30-4.18 (m, 2H), 2.51-2.37 (m, 2H), 1.42-1.35 (m, 1H), 1.31-1.23 (m, 3H), 1.14-1.08 (m, 1H). LCMS M+H=293.07.

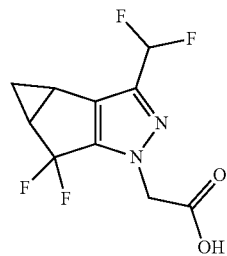 [SMILES: O=C(O)Cn1nc(C(F)F)c2c1C(F)(F)C1CC21]

2-(3-(difluoromethyl)-5,5-difluoro-3b,4,4a,5-tetrahydro-1H-cyclopropa[3,4]cyclopenta[1,2-c]pyrazol-1-yl)acetic acid To a stirred solution of ethyl 2-(3-(difluoromethyl)-5,5-difluoro-3b,4,4a,5-tetrahydro-1H-cyclopropa[3,4]cyclopenta[1,2-c]pyrazol-1-yl)acetate (15 g, 49.8 mmol) in THF (17 mL) and MeOH (65.6 mL), was added LiOH (1.788 g, 74.7 mmol in water 65.6 mL) at 0° C. under N2 atmosphere. The reaction mixture was stirred for 3 h at 27° C. Progress of the reaction was monitored by TLC (SiO$_2$, 5% MeOH/DCM, Rf=0.2, UV Active). After completion, the reaction mixture was evaporated under reduced pressure, diluted with water (50 mL) and washed with EtOAc (2×250 mL) to remove impurities. The Aqueous layer was acidified with 1N HCl up to pH=2-3, extracted with EtOAc (3×1000 mL). The combined organics were dried over anhydrous Na$_2$SO$_4$, filtered and evaporated under reduced pressure to afford 2-(3-(difluoromethyl)-5,5-difluoro-3b,4,4a,5-tetrahydro-1H-cyclopropa[3,4]cyclopenta[1,2-c]pyrazol-1-yl)acetic acid (14 g, Yield: 98%) as an off white solid. LCMS M+H=265.15.

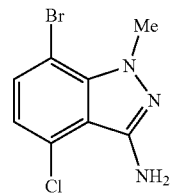 [SMILES: Cn1nc(N)c2c(Cl)ccc(Br)c21]

7-bromo-4-chloro-1-methyl-1H-indazol-3-amine

To a solution of 3-bromo-6-chloro-2-fluorobenzonitrile (360.0 g, 1.55 mol, 1.0 equiv.) in ethanol (1.08 L) was added methylhydrazine sulphate (1.11 kg, 7.73 mol, 5.0 equiv.) followed by the addition of triethylamine (1.3 L, 9.3 mol, 6.0 equiv.) at 25-35° C. The reaction mixture was heated to 110° C. and maintained for 15 h (the reaction was monitored by TLC). After completion of the reaction the mixture was cooled to room temperature. Water (3.0 L) was added and the mixture was stirred for 1 h at room temperature. The solids were isolated via filtration and were washed with water. The wet solid was dried under vacuum at 50° C. for 12-15 hours. The crude solid was purified by column chromatography (10% EA/hexanes to 40% EA/Hexanes) to afford the product as a pale-yellow solid. Yield: 185.0 g (46.0%).

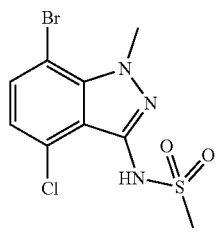 [SMILES: Cn1nc(NS(C)(=O)=O)c2c(Cl)ccc(Br)c21]

N-(7-bromo-4-chloro-1-methyl-1H-indazol-3-yl) methanesulfonamide

To a solution of 7-bromo-4-chloro-1-methyl-1H-indazol-3-amine (1.40 g, 5.37 mmol) in DCM (30 mL) was added Hunig's Base (3.75 mL, 21.5 mmol) and then the reaction was cooled in an ice bath and methanesulfonyl chloride (1.26 mL, 16.1 mmol) was added. The reaction mixture was stirred at this temperature for 1 h (precipitate formed). Mixture was then diluted with dichloromethane (100 mL) and washed with water, 1 M HCl and brine, dried (Na$_2$SO$_4$), filtered and concentrated in vacuo. The residue was taken up in EtOH (30 ml) and 10 ml of 20% aq. NaOH. The resulted mixture heated with a heat gun until it became a homogeneous solution and stirred at rt for 30 min. The mixture was diluted with water (80 mL) and acidified with 1 N HCl (60 mL). The precipitate was filtered, washed with water, and dried in vacuo to afford the title product (1.5 g) as an off-white solid. $^1$H NMR (500 MHz, CDCl$_3$) δ7.48 (d, J=7.9 Hz, 1H), 7.24 (br s, 1H), 6.95 (d, J=7.9 Hz, 1H), 4.38 (s, 3H), 3.42 (s, 3H). LC/MS (M+H)$^+$=337.80.

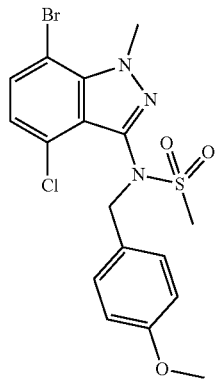 [SMILES: COc1ccc(CN(c2nn(C)c3c(Br)ccc(Cl)c23)S(C)(=O)=O)cc1]

N-(7-bromo-4-chloro-1-methyl-1H-indazol-3-yl)-N-(4-methoxybenzyl)methanesulfonamide To a mixture of N-(7-bromo-4-chloro-1-methyl-1H-indazol-3-yl)methanesulfonamide (1.3 g, 3.84 mmol) and 1-(chloromethyl)-4-methoxybenzene (0.625 mL, 4.61 mmol) in DMF (30 mL) was added cesium carbonate (1.626 g, 4.99 mmol) and the mixture was heated at 80° C. for 2 h. The mixture was poured into water (100 mL) and extracted with EtOAc (50 ml, 2×). The combined organic layer was washed with brine, dried over MgSO$_4$, filtered and concentrated in vacuo. The residue was purified by Biotage (0-35% EtOAc-hexanes) to afford the title product (1.5 g) as a white foam. $^1$H NMR (500 MHz, CDCl$_3$) δ7.44 (d, J=7.9 Hz, 1H), 7.31 (d, J=8.5 Hz, 2H), 6.99 (d, J=7.9 Hz, 1H), 6.84 (d, J=8.5 Hz, 2H), 4.99 (br s, 1H), 4.76 (br s, 1H), 4.40 (s, 3H), 3.80 (s, 3H), 3.01 (s, 3H).

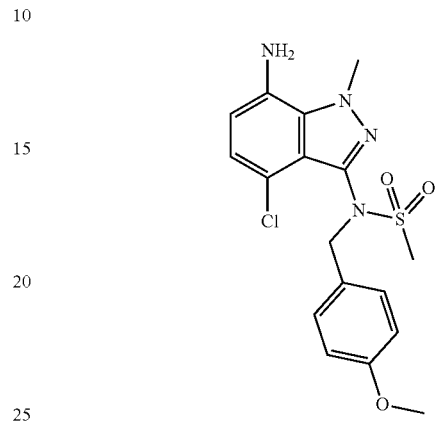

N-(7-amino-4-chloro-1-methyl-1H-indazol-3-yl)-N-(4-methoxybenzyl)methanesulfonamide Following the reference: Andersen, Jacob et al, Synlett 2005 (14), 2209-2213. To a mixture of N-(7-bromo-4-chloro-1-methyl-1H-indazol-3-yl)-N-(4-methoxybenzyl) methane sulfonamide (600.0 mg, 1.308 mmol), copper(I) iodide (49.8 mg, 0.262 mmol), sodium ascorbate (518 mg, 2.62 mmol) and (1R,2R)—N1,N2-dimethylcyclohexane-1,2-diamine (46.5 mg, 0.327 mmol) in NMP (10 mL) was added a solution of sodium azide (255 mg, 3.92 mmol) in Water (2.0 mL). The mixture was then sealed and heated in a microwave system at 120° C. for 2.5 h. The mixture was then filtered through a pad of Celite and the pad was washed with EtOAc. The filtrate was poured into water (100 mL) and extracted with EtOAc (50 ml, 2×). The combined organic layer was washed with brine, dried over MgSO$_4$, filtered and evaporated in vacuo. The residue was purified by Biotage (5-100% EtOAc/hexanes) to afford the title product (400 mg) as an off-white solid. $^1$H NMR (400 MHz, CDCl$_3$) δ7.33-7.29 (m, 2H), 6.89 (d, J=7.8 Hz, 1H), 6.85-6.79 (m, 2H), 6.48 (d, J=7.8 Hz, 1H), 5.11 (br.s, 1H), 4.81 (br.s, 1H), 4.30 (s, 3H), 3.80 (br s, 2H), 3.79 (s, 3H), 2.99 (s, 3H). LC/MS (M+H)$^+$=395.00.

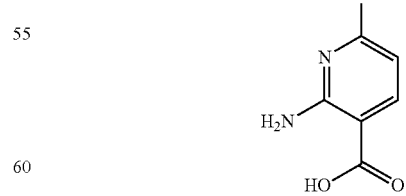

2-amino-6-(benzyloxy)nicotinic acid

A solution of 2-amino-6-chloronicotinic acid (5 g, 29 mmol) and potassium tert-butoxide (9.75 g, 87 mmol) in benzyl alcohol (97 mL) was heated to 120° C. for 3 h. After cooling to ambient temperature, the very dark reaction mixture was added to water and washed with ether (×3). The aqueous layer was then acidified with 0.5 M citric acid. The tan precipitate filtered to provide the product (4.4 g, 62%) which was used in the next reaction without further purification. $^1$H NMR (500 MHz, DMSO-d6) δ12.40 (br s, 1H), 7.94 (d, J=8.55 Hz, 1H), 7.06-7.52 (m, 5H), 6.04 (d, J=8.24 Hz, 1H), 5.33 (s, 2H). LC/MS: m/z=245.15 [M+1]$^+$.

Preparation of N-[(6P)-7-{2-[(1S)-1-amino-2-(3,5-difluorophenyl)ethyl]-7-hydroxy-4-oxo-3H,4H-pyrido[2,3-d]pyrimidin-3-yl}-4-chloro-1-methyl-1H-indazol-3-yl]-N-[(4-methoxyphenyl)methyl] methanesulfonamide Approach #1, Scheme

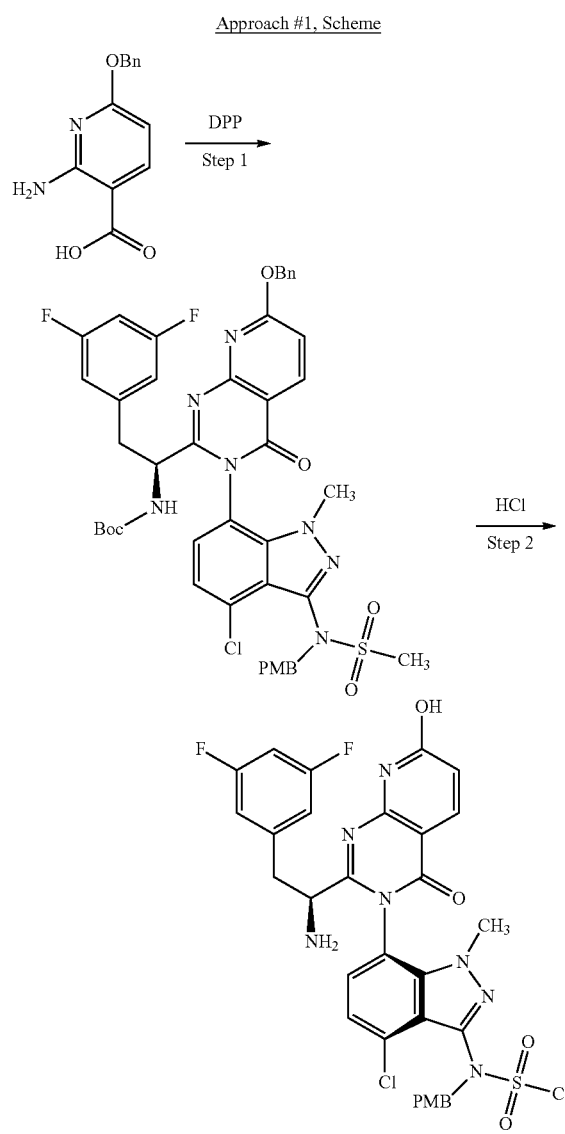

Step 1:

A mixture of (S)-2-((tert-butoxycarbonyl)amino)-3-(3,5-difluorophenyl)propanoic acid (0.247 g, 0.819 mmol), N-(7-amino-4-chloro-1-methyl-1H-indazol-3-yl)-N-(4-methoxybenzyl)methanesulfonamide (0.323 g, 0.819 mmol), and diphenyl phosphite ("DPP", 0.634 mL, 3.28 mmol) in pyridine (3 mL) was heated at 75° C. for 2.5 h. Upon cooling to ambient temperature, the reaction mixture was concentrated in vacuo and purified using silica gel flash chromatography (120 g Isco column) using 0-45% ethyl acetate in hexanes. The desired fractions were pooled and concentrated to afford a pale yellow foamy solid (0.34 g, 47%), tert-butyl (1-(7-(benzyloxy)-3-(4-chloro-3-(N-(4-methoxybenzyl)methylsulfonamido)-1-methyl-1H-indazol-7-yl)-4-oxo-3,4-dihydropyrido[2,3-d]pyrimidin-2-yl)-2-(3,5-difluorophenyl) ethyl)carbamate (mixture of four stereoisomers) wherein (S)-tert-butyl (1-(7-(benzyloxy)-3-(4-chloro-3-(N-(4-methoxybenzyl)methylsulfonamido)-1-methyl-1H-indazol-7-yl)-4-oxo-3,4-dihydropyrido[2,3-d]pyrimidin-2-yl)-2-(3, 5-difluorophenyl)ethyl)carbamate is the major component. LC/MS: m/z=886.25 [M+1]$^+$.

Step 2:

4 N HCl in dioxane (8.46 ml, 33.8 mmol) was added to a solution of tert-butyl (1-(7-(benzyloxy)-3-(4-chloro-3-(N-(4-methoxybenzyl)methylsulfonamido)-1-methyl-1H-indazol-7-yl)-4-oxo-3,4-dihydropyrido[2,3-d]pyrimidin-2-yl)-2-(3,5-difluorophenyl)ethyl)carbamate (Product from Step 1, 3 g, 3.38 mmol) in DCM (16.92 ml). The mixture was stirred for 1 h. More 4 N HCl in dioxane (8.46 ml, 33.8 mmol) was added followed by methanol until a homogenous solution was formed. After stirring for 1 h, the pale-yellow solution was concentrated in vacuo. The crude product was taken up in DCM, washed with saturated aqueous NaHCO$_3$, dried over Na$_2$SO$_4$, and concentrated in vacuo to give a yellow solid. The crude solid was purified by reverse phase chromatography on a RediSep Gold C$_{18}$ column using a gradient of Solvent A: Solvent B 90:10→40:20 (Solvent A=95:5 CH$_3$CN:water with 0.1% TFA; Solvent B=95:5 Water:Acetonitrile with 0.1% TFA) to separate the atropisomers. Two peaks contain the desired product mass; the second (major) eluting peak was collected and concentrated in vacuo to remove acetonitrile. The resultant white suspension was neutralized with 1 N NaOH and the mixture was extracted with ethyl acetate. The EtOAc extracts were dried over Na$_2$SO$_4$ and concentrated in vacuo to provide 1.25 g of the major atropisomer. This material was further purified by HPLC on a Chiralpak IC column using a pre-conditioned column (0.1% iPrNH$_2$) and neutral solvents (40:60 EtOH: Heptane) isolating the major peak to provide the chirally pure product N-[(6P)-7-{2-[(1S)-1-amino-2-(3,5-difluorophenyl)ethyl]-7-hydroxy-4-oxo-3H,4H-pyrido[2,3-d]pyrimidin-3-yl}-4-chloro-1-methyl-1H-indazol-3-yl]-N-[(4-methoxyphenyl)methyl]methanesulfonamide (0.96 g, 41%). $^1$H NMR (500 MHz, DMSO-d6) δ7.86-7.98 (m, 1H) 7.15-7.37 (m, 4H) 6.97-7.06 (m, 1 H) 6.70-6.89 (m, 4H) 6.40-6.48 (m, 1H) 4.70-4.88 (m, 2H) 3.41-3.81 (m, 7H) 3.20-3.28 (m, 1H) 3.08-3.12 (m, 3H) 2.71-2.79 (m, 1H) 1.69-2.00 (m, 2H). LC/MS: m/z=696.20[M+1]$^+$.

Approach #2, Scheme

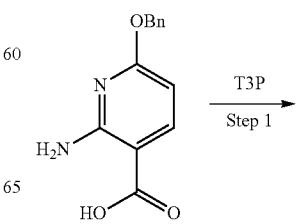

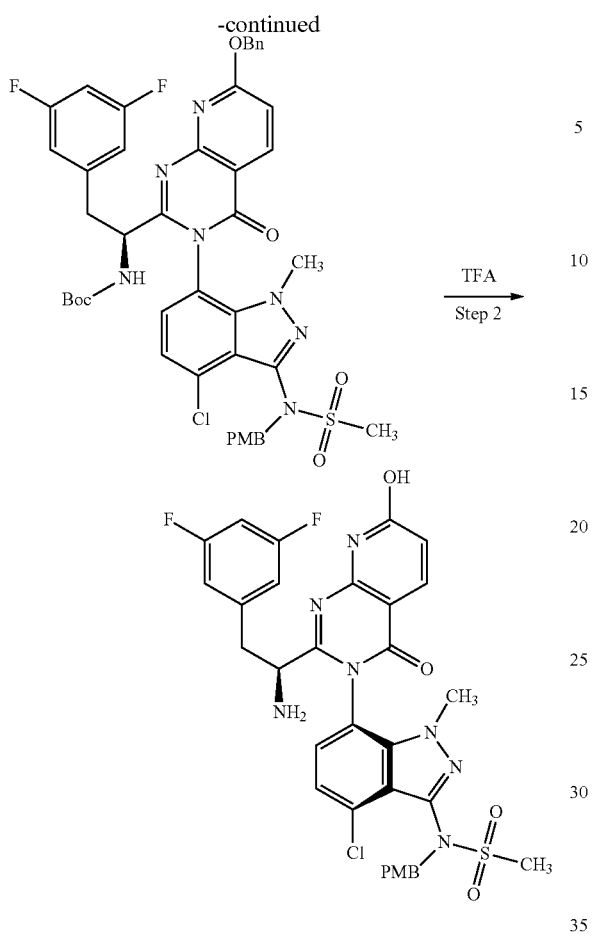

Step 1:

To a suspension of (S)-2-((tert-butoxycarbonyl)amino)-3-(3,5-difluorophenyl)propanoic acid (5.49 g, 18.23 mmol) and 2-amino-6-(benzyloxy)nicotinic acid (4.45 g, 18.23 mmol) in acetonitrile (92 mL) (yellow solution) at −25° C. was added pyridine (9.83 mL, 122 mmol) followed by 2,4,6-tripropyl-1,3,5,2,4,6-trioxatriphosphinane 2,4,6-trioxide ("T3P", 45.2 ml, 76 mmol). The reaction mixture (became a clear solution after T3P addition) was stirred at −25° C. to 10° C. over 4.5 h, then N-(7-amino-4-chloro-1-methyl-1H-indazol-3-yl)-N-(4-methoxybenzyl)methanesulfonamide (6 g, 15.19 mmol) was added and the mixture was stirred for 18 h while warming to rt. The reaction mixture was diluted with ethyl acetate, washed with 1N NaOH, then water, then 0.5 M citric acid, then water, then dried over $Na_2SO_4$ and concentrated in vacuo. The resulting residue was purified on silica (330 g RediSep Gold column) using 0-60% ethyl acetate in hexanes over 15 CV, then holding at 60% EtOAc for 10 CV. The desired fractions were pooled and concentrated to afford a pale yellow solid (8.1 g, 9.14 mmol, 60.1% yield), a mixture of tert-butyl N-[(1S)-1-[(3P,3P)-7-(benzyloxy)-3-(4-chloro-3-{N-[(4-methoxyphenyl)methyl]methanesulfonamido}-1-methyl-1H-indazol-7-yl)-4-oxo-3H,4H-pyrido[2,3-d]pyrimidin-2-yl]-2-(3,5-difluorophenyl)ethyl]carbamate (major) and tert-butyl N-[(1S)-1-[(3M,3M)-7-(benzyloxy)-3-(4-chloro-3-{N-[(4-methoxyphenyl)methyl]methanesulfonamido}-1-methyl-1H-indazol-7-yl)-4-oxo-3H,4H-pyrido[2,3-d]pyrimidin-2-yl]-2-(3,5-difluorophenyl)ethyl]carbamate (minor). LC/MS: m/z=886.25[M+1]+.

Step 2:

TFA (21.1 mL, 274 mmol) was added to a solution of tert-butyl (S)-(1-(7-(benzyloxy)-3-(4-chloro-3-(N-(4-methoxybenzyl)methylsulfonamido)-1-methyl-1H-indazol-7-yl)-4-oxo-3,4-dihydropyrido[2,3-d]pyrimidin-2-yl)-2-(3,5-difluorophenyl)ethyl)carbamate (Product from Step 1, 8.1 g, 9.14 mmol) in dichloromethane (45.7 mL). The mixture was stirred at rt for 2 h. The resultant pale-yellow solution was concentrated. The residue was taken up in ethyl acetate, then washed three times with 1 N NaOH, then dried over $Na_2SO_4$ and then concentrated in vacuo to afford an oily residue. The residue was purified on silica gel (330 g RediSep Gold column) by a gradient method of Solvent A: Solvent B 65:35→0:100 (2 CV), then 0:100 (9 CV); Solvent A=hexanes; Solvent B=9:9:2 hexanes:ethyl acetate:MeOH. The first eluting isomer (major) was collected and concentrated in vacuo to afford N-[(6P)-7-{2-[(1S)-1-amino-2-(3,5-difluorophenyl)ethyl]-7-hydroxy-4-oxo-3H,4H-pyrido[2,3-d]pyrimidin-3-yl}-4-chloro-1-methyl-1H-indazol-3-yl]-N-[(4-methoxyphenyl)methyl]methanesulfonamide (4.1 g, 5.89 mmol, 64.5% yield). $^1$H NMR (500 MHz, DMSO-d6) δ7.86-7.98 (m, 1H) 7.15-7.37 (m, 4H) 6.97-7.06 (m, 1H) 6.70-6.89 (m, 4H) 6.40-6.48 (m, 1H) 4.70-4.88 (m, 2H) 3.41-3.81 (m, 7H) 3.20-3.28 (m, 1H) 3.08-3.12 (m, 3H) 2.71-2.79 (m, 1H) 1.69-2.00 (m, 2H). LC/MS: m/z=696.20 [M+1]+.

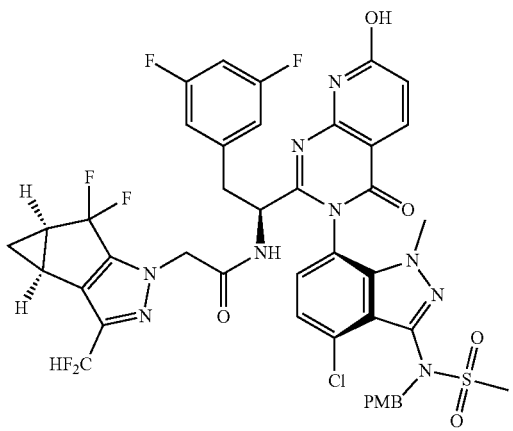

N—((S)-1-((3P)-3-(4-chloro-3-(N-(4-methoxybenzyl)methylsulfonamido)-1-methyl-1H-indazol-7-yl)-7-hydroxy-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide To a stirred solution of N-[(6P)-7-{2-[(1S)-1-amino-2-(3,5-difluorophenyl)ethyl]-7-hydroxy-4-oxo-3H,4H-pyrido[2,3-d]pyrimidin-3-yl}-4-chloro-1-methyl-1H-indazol-3-yl]-N-[(4-methoxyphenyl)methyl]methanesulfonamide (0.926 g, 1.330 mmol) in DMF (13 ml) was added 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (0.351 g, 1.330 mmol), 2-(3H-[1,2,3]triazolo[4,5-b]pyridin-3-yl)-1,1,3,3-tetramethylisouronium hexafluorophosphate (V) ("HATU", 0.531 g, 1.397 mmol), and DIPEA (0.581 ml, 3.33 mmol). The reaction mixture was stirred for 2 h after which the reaction mixture was diluted with water and extracted with ethyl acetate. The combined EtOAc extractions were washed with brine, dried over Na$_2$SO$_4$, and concentrated in vacuo. The crude product was purified via silica gel flash chromatography using 10-100% ethyl acetate in hexanes to provide N—((S)-1-((3P)-3-(4-chloro-3-(N-(4-methoxybenzyl)methylsulfonamido)-1-methyl-1H-indazol-7-yl)-7-hydroxy-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (1.1 g, 88%) as an off-white foamy solid. LC/MS: m/z=942.25 [M+1]$^+$.

EXAMPLE 1

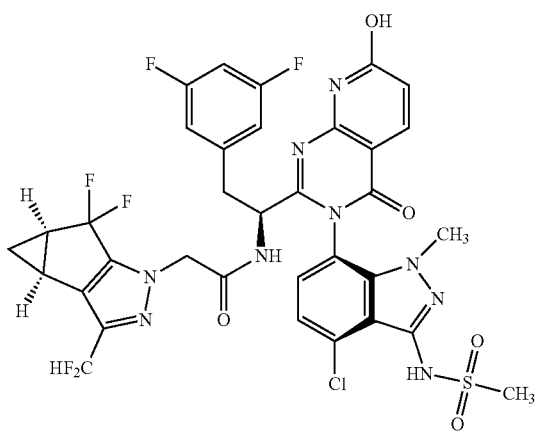

N—((S)-1-((3P)-3-(4-chloro-1-methyl-3-(methylsulfonamido)-1H-indazol-7-yl)-7-hydroxy-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide To a solution of N—((S)-1-((3P)-3-(4-chloro-3-(N-(4-methoxybenzyl)methylsulfonamido)-1-methyl-1H-indazol-7-yl)-7-hydroxy-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (0.05 g, 0.053 mmol) in DCM (1 mL) and TFA (0.250 mL) was added triflic acid (0.014 mL, 0.159 mmol). The resultant purple solution was stirred for 1 h and then concentrated in vacuo. The crude residue was taken up in ethyl acetate and washed with saturated aqueous NaHCO3. The organic layer was concentrated and then purified by reverse phase preparative chromatography. Purification Conditions: Column: Waters Xterra C18, 19×100 mm, 10 μm particles; Solvent A=0.1% NH4OH in 100% Water. Solvent B=Acetonitrile. Flow Rate=40 mL/min. Start % B=37.6. Final % B=57.6. Gradient Time=6 min, then a 2 min hold at 98% B. Wavelength=215 and 254 nm. ESI+Range: 150 to 1500 dalton. Sample was loaded at 25% B. The product was isolated (26 mg, 59%). $^1$H NMR (500 MHz, METHANOL-d4) δ8.09-8.17 (m, 1H) 7.27-7.32 (m, 1H) 7.16-7.21 (m, 1H) 6.58-6.85 (m, 5H) 4.81-4.83 (m, 2H) 4.42-4.47 (m, 2H) 3.65-3.70 (m, 3H) 3.43-3.49 (m, 1H) 3.23-3.27 (m, 3H) 3.06-3.14 (m, 1H) 2.41-2.50 (m, 2H) 1.35-1.41 (m, 1H) 0.96-1.02 (m, 1H). LC/MS retention time=1.15 min; m/z=822.6[M+H]$^+$ (Column: Acquity UPLC BEH C$_{18}$, 2.1×30 mm, 1.7 μm particles; Solvent A=0.1% Formic acid in 100% Water. Solvent B=0.1% Formic Acid in 100% Acetonitrile. Flow Rate=0.8 mL/min. Start % B=5. Final % B=95. Gradient Time=1.6 min, then a 0.25 min hold at 95% B. Wavelength=215 nm.

EXAMPLE 2

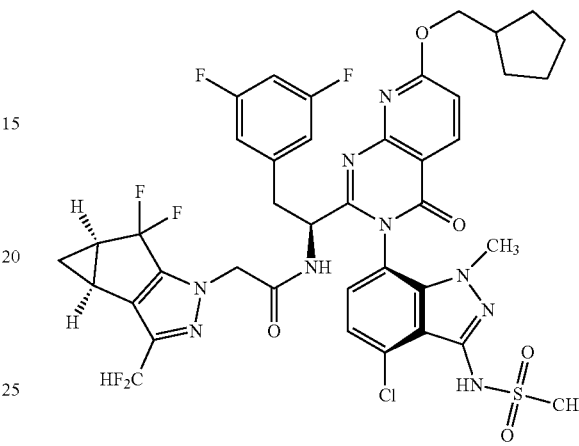

N—((S)-1-((3P)-3-(4-chloro-1-methyl-3-(methylsulfonamido)-1H-indazol-7-yl)-7-(cyclopentylmethoxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide A solution of diisopropyl (E)-diazene-1,2-dicarboxylate (0.031 mL, 0.159 mmol) in THF (0.2 mL) was added dropwise to a mixture of N—((S)-1-((3P)-3-(4-chloro-3-(N-(4-methoxybenzyl)methylsulfonamido)-1-methyl-1H-indazol-7-yl)-7-hydroxy-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (0.05 g, 0.053 mmol), cyclopentylmethanol (0.016 g, 0.159 mmol), and triphenylphosphine (0.045 g, 0.170 mmol) in THF (0.8 mL). The reaction mixture was stirred for 18 h after which the reaction mixture was concentrated in vacuo. The crude intermediate was taken up in DCM (0.5 ml) and TFA (0.25 mL) and triflic acid (0.014 mL, 0.159 mmol) was added. The resultant purple solution was stirred for 1 h and concentrated in vacuo. The crude product was taken up in ethyl acetate and washed with saturated aqueous NaHCO3. The organic layer was concentrated in vacuo and purified by reverse phase preparative HPLC. Purification Conditions: Column: Zorbax Eclipse Plus C18, 21.2×100 mm, 5 μm particles; Solvent A=0.1% Formic Acid in 100% Water. Solvent B=Acetonitrile. Flow Rate=40 mL/min. Start % B=61.6 Final % B=81.6. Gradient Time=7 min, then a 2 min hold at 98% B. Wavelength=215 and 254 nm. ESI+Range: 150 to 1500 dalton. Sample was loaded at 61.6% B. The product was isolated (20 mg, 42%). $^1$H NMR (500 MHz, METHANOL-d4) δ8.45-8.52 (m, 1H) 7.29-7.34 (m, 1H) 7.19-7.24 (m, 1H) 7.03-7.08 (m, 1H) 6.55-6.84 (m, 4H) 4.42-4.62 (m, 5H) 3.59-3.64 (m, 3H) 3.45-3.50 (m, 1H) 3.23-3.27 (m, 3H) 3.08-3.16 (m, 1H) 2.38-2.57 (m, 3H)

1.87-1.97 (m, 2H) 1.63-1.80 (m, 5H) 1.43-1.52 (m, 2H) 1.35-1.40 (m, 1H) 0.99-1.04 (m, 1H). LC/MS retention time=1.58 min; m/z=904.8[M+H]$^+$ (Column: Acquity UPLC BEH C18, 2.1×30 mm, 1.7 μm particles; Solvent A=0.1% Formic acid in 100% Water. Solvent B=0.1% Formic Acid in 100% Acetonitrile. Flow Rate=0.8 mL/min. Start % B=5. Final % B=95. Gradient Time=1.6 min, then a 0.25 min hold at 95% B. Wavelength=215 nm.

EXAMPLE 3

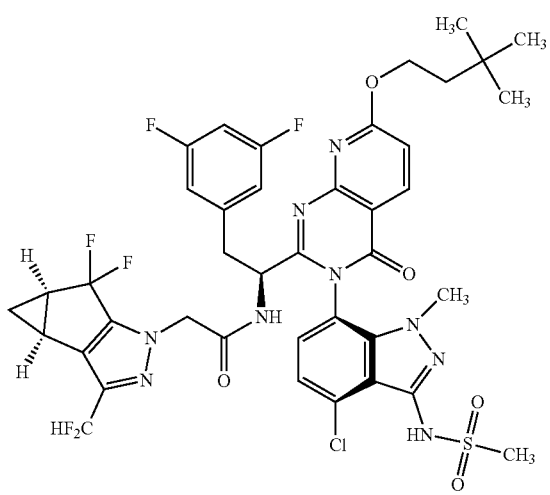

N—((S)-1-((3P)-3-(4-chloro-1-methyl-3-(methyl-sulfonamido)-1H-indazol-7-yl)-7-(3,3-dimethylbu-toxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide Prepared in 37% yield (18 mg) from 3,3-dimethylbutan-1-ol using 50 mg starting pyridone following the same procedure as Example 2. Purification Conditions: Column: Zorbax Eclipse Plus C18, 21.2×100 mm, 5 μm particles; Solvent A=0.1% Formic Acid in 100% Water. Solvent B=Acetonitrile. Flow Rate=40 mL/min. Start % B=62.8 Final % B=82.8. Gradient Time=7 min, then a 2 min hold at 98% B. Wavelength=215 and 254 nm. ESI+Range: 150 to 1500 dalton. Sample was loaded at 62.8% B. $^1$H NMR (500 MHz, METHANOL-d$_4$) δ8.44-8.54 (m, 1H) 7.27-7.34 (m, 1H) 7.19-7.24 (m, 1H) 7.00-7.06 (m, 1H) 6.54-6.83 (m, 4H) 4.83-4.85 (m, 2H) 4.53-4.69 (m, 4H) 3.59-3.64 (m, 3H) 3.43-3.51 (m, 1H) 3.22-3.26 (m, 3H) 3.10-3.16 (m, 1H) 2.39-2.46 (m, 2H) 1.82-1.88 (m, 2H) 1.33-1.40 (m, 1H) 1.06-1.10 (m, 9H) 0.98-1.04 (m, 1H). LC/MS retention time=1.54 min; m/z=906.8[M+H]$^+$ (Column: Acquity UPLC BEH C18, 2.1×30 mm, 1.7 μm particles; Solvent A=0.1% Formic acid in 100% Water. Solvent B=0.1% Formic Acid in 100% Acetonitrile. Flow Rate=0.8 mL/min. Start % B=5. Final % B=95. Gradient Time=1.6 min, then a 0.25 min hold at 95% B. Wavelength=215 nm.

EXAMPLE 4

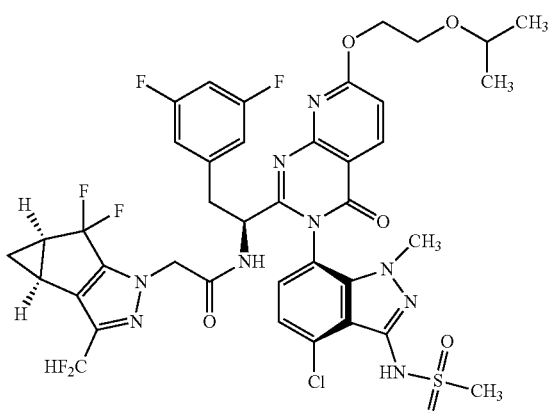

N—((S)-1-((3P)-3-(4-chloro-1-methyl-3-(methyl-sulfonamido)-1H-indazol-7-yl)-7-(2-isopropoxy-ethoxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide Prepared in 33% yield (16 mg) from 2-isopropoxyethan-1-ol using 50 mg starting pyridone following the same procedure as Example 2. Purification Conditions: Column: Zorbax Eclipse Plus C18, 21.2×100 mm, 5 μm particles; Solvent A=0.1% Formic Acid in 100% Water. Solvent B=Acetonitrile. Flow Rate=40 mL/min. Start % B=53.1 Final % B=73.1. Gradient Time=7 min, then a 2 min hold at 98% B. Wavelength=215 and 254 nm. ESI+Range: 150 to 1500 dalton. Sample was loaded at 35% B. $^1$H NMR (500 MHz, METHANOL-d$_4$) δ8.46-8.54 (m, 1H) 7.29-7.33 (m, 1H) 7.19-7.22 (m, 1H) 7.08-7.12 (m, 1H) 6.56-6.83 (m, 4H) 4.66-4.71 (m, 2H) 4.52-4.62 (m, 2H) 3.89-3.94 (m, 2H) 3.72-3.81 (m, 1H) 3.61-3.65 (m, 3H) 3.44-3.50 (m, 1H) 3.23-3.26 (m, 3H) 3.09-3.16 (m, 1H) 2.39-2.47 (m, 2H) 1.33-1.40 (m, 1H) 1.20-1.25 (m, 6H) 0.98-1.04 (m, 1H) [some proton peak may be under the solvent peak]. LC/MS retention time=1.39 min; m/z=908.6[M+H]$^+$ (Column: Acquity UPLC BEH C18, 2.1×30 mm, 1.7 μm particles; Solvent A=0.1% Formic acid in 100% Water. Solvent B=0.1% Formic Acid in 100% Acetonitrile. Flow Rate=0.8 mL/min. Start % B=5. Final % B=95. Gradient Time=1.6 min, then a 0.25 min hold at 95% B. Wavelength=215 nm.

EXAMPLE 7

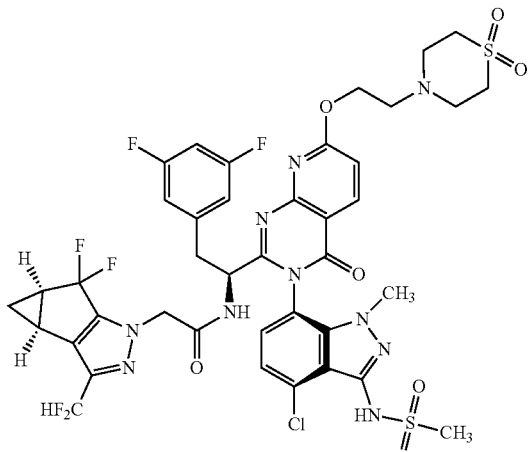

N—((S)-1-((3P)-3-(4-chloro-1-methyl-3-(methyl-sulfonamido)-1H-indazol-7-yl)-7-(2-(1,1-dioxidothiomorpholino)ethoxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide Prepared in 16% yield (7 mg) from 4-(2-hydroxyethyl)thiomorpholine 1,1-dioxide using 40 mg starting pyridone following the same procedure as Example 2. Purification conditions: Column: Zorbax Eclipse Plus C18, 21.2×100 mm, 5 μm particles; Solvent A=0.1% Formic Acid in 100% Water. Solvent B=Acetonitrile. Flow Rate=40 mL/min. Start % B=40.50 Final % B=60.50. Gradient Time=7 min, then a 2 min hold at 98% B. Wavelength=215 and 254 nm. ESI+ Range: 150 to 1500 dalton. Sample was loaded at 30% B. $^1$H NMR (500 MHz, METHANOL-$d_4$) δ ppm 8.47-8.54 (m, 1H) 7.29-7.35 (m, 1H) 7.20-7.26 (m, 1H) 7.06-7.12 (m, 1H) 6.55-6.84 (m, 4H) 4.68-4.79 (m, 2H) 4.50-4.62 (m, 3H) 3.61-3.65 (m, 3H) 3.45-3.51 (m, 1H) 3.18-3.27 (m, 7H) 3.08-3.16 (m, 7H) 2.39-2.49 (m, 2H) 1.34-1.41 (m, 1H) 0.97-1.04 (m, 1H). LC/MS retention time=1.15 min; m/z=983.9[M+H]$^+$. Column: Acquity UPLC BEH C18, 2.1×30 mm, 1.7 μm particles; Solvent A=0.1% Formic acid in 100% Water. Solvent B=0.1% Formic Acid in 100% Acetonitrile. Flow Rate=0.8 mL/min. Start % B=5. Final % B=95. Gradient Time=1.6 min, then a 0.25 min hold at 95% B. Wavelength=215 nm.

EXAMPLE 9

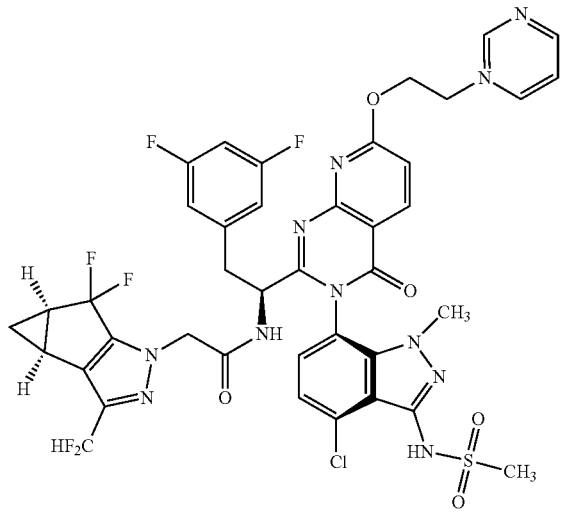

N—((S)-1-((3P)-3-(4-chloro-1-methyl-3-(methyl-sulfonamido)-1H-indazol-7-yl)-4-oxo-7-(pyrimidin-2-ylmethoxy)-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide Prepared in 38% yield (19 mg) from pyrimidin-2-yl-methanol using 50 mg starting pyridone following the same procedure as Example 2. Purification Conditions: Column: Zorbax Eclipse Plus C18, 21.2×100 mm, 5 μm particles; Solvent A=0.1% Formic Acid in 100% Water. Solvent B=Acetonitrile. Flow Rate=40 mL/min. Start % B=43.3 Final % B=63.3. Gradient Time=7 min, then a 2 min hold at 98% B. Wavelength=215 and 254 nm. ESI+Range: 150 to 1500 dalton. Sample was loaded at 30% B. $^1$H NMR (500 MHz, METHANOL-d4) δ ppm 8.79-8.88 (m, 2H) 8.52-8.59 (m, 1H) 7.44-7.51 (m, 1H) 7.16-7.34 (m, 3H) 6.53-6.83 (m, 4H) 5.80-5.90 (m, 2H) 4.82-4.85 (m, 2H) 4.49-4.61 (m, 2H) 3.58-3.63 (m, 3H) 3.39-3.44 (m, 1H) 3.22-3.27 (m, 3H) 3.02-3.10 (m, 1H) 2.39-2.46 (m, 2H) 1.33-1.40 (m, 1H) 0.97-1.03 (m, 1H). LC/MS retention time=1.25 min; m/z=914.8[M+H]$^+$ (Column: Acquity UPLC BEH C18, 2.1×30 mm, 1.7 μm particles; Solvent A=0.1% Formic acid in 100% Water. Solvent B=0.1% Formic Acid in 100% Acetonitrile. Flow Rate=0.8 mL/min. Start % B=5. Final % B=95. Gradient Time=1.6 min, then a 0.25 min hold at 95% B. Wavelength=215 nm.

EXAMPLE 11

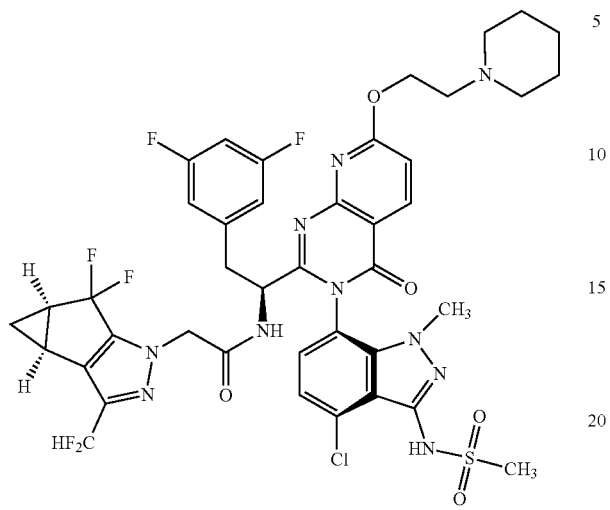

N—((S)-1-((3P)-3-(4-chloro-1-methyl-3-(methyl-sulfonamido)-1H-indazol-7-yl)-4-oxo-7-(2-(piperidin-1-yl)ethoxy)-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide Prepared in 13% yield (7 mg) from 2-(piperidin-1-yl)ethan-1-ol using 50 mg starting pyridone following the same procedure as Example 2. Purification Conditions: Column: Zorbax Eclipse Plus C18, 21.2×100 mm, 5 μm particles; Solvent A=0.1% Formic Acid in 100% Water. Solvent B=Acetonitrile. Flow Rate=40 mL/min. Start % B=25.8 Final % B=45.8. Gradient Time=7 min, then a 2 min hold at 98% B. Wavelength=215 and 254 nm. ESI+Range: 150 to 1500 dalton. Sample was loaded at 15% B. $^1$H NMR (500 MHz, METHANOL-$d_4$) δ8.12-8.19 (m, 1H) 7.34-7.37 (m, 2H) 6.55-6.89 (m, 6H) 4.72-4.77 (m, 1H) 4.32-4.59 (m, 3H) 3.64-3.67 (m, 3H) 3.45-3.52 (m, 1H) 3.14-3.28 (m, 9H) 2.41-2.50 (m, 3H) 1.87-1.95 (m, 1H) 1.77-1.86 (m, 4H) 1.62-1.69 (m, 2H) 1.37-1.43 (m, 1H) 0.97-1.01 (m, 1H). LC/MS retention time=1.32 min; m/z=933.2[M+H]$^+$ (Column: Acquity UPLC BEH C18, 2.1×30 mm, 1.7 μm particles; Solvent A=0.1% Formic acid in 100% Water. Solvent B=0.1% Formic Acid in 100% Acetonitrile. Flow Rate=0.8 mL/min. Start % B=5. Final % B=95. Gradient Time=1.6 min, then a 0.25 min hold at 95% B. Wavelength=215 nm.

Alternate preparation of N-(7-amino-4-chloro-1-methyl-1H-indazol-3-yl)-N-(4-methoxybenzyl)methanesulfonamide

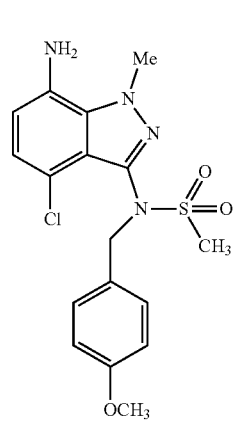 [SMILES: COc1ccc(CN(c2nn(C)c3c(N)ccc(Cl)c23)S(C)(=O)=O)cc1]

Synthesis Scheme:

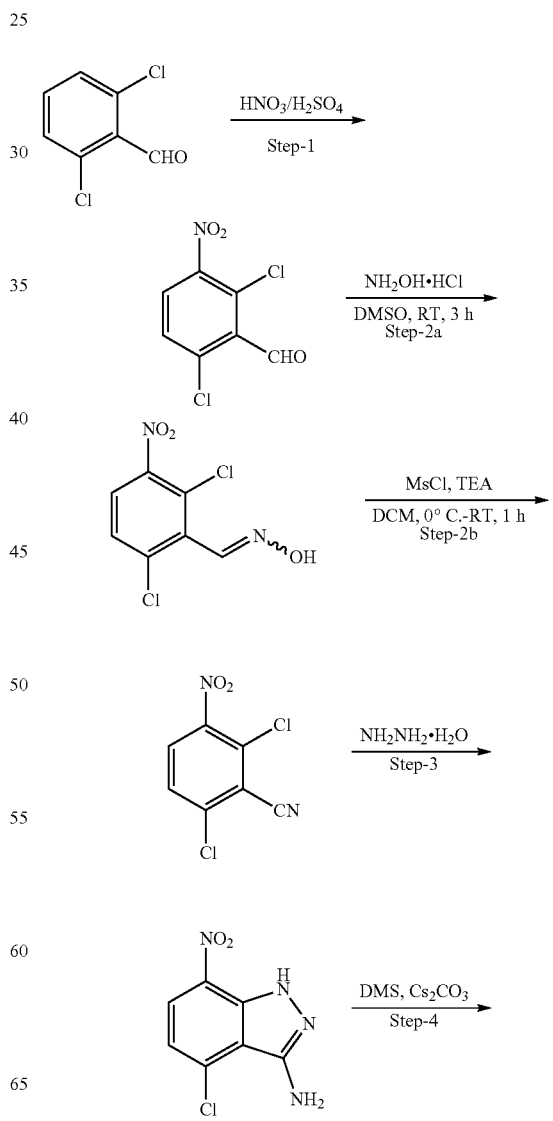

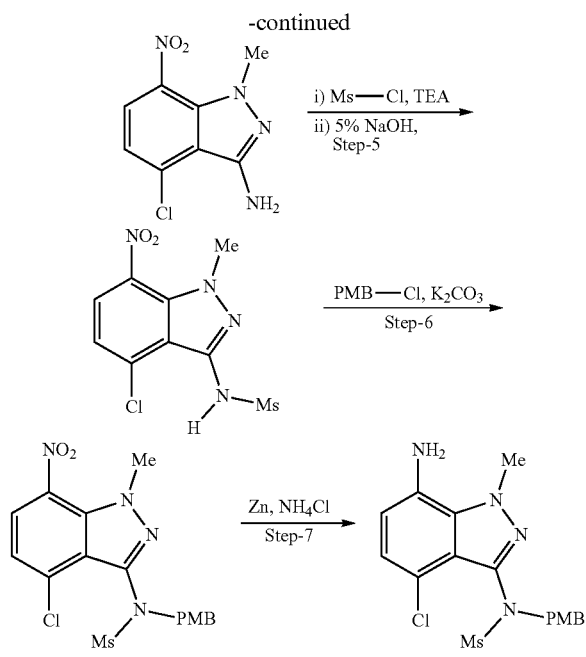

Step 1: Preparation of 2,6-dichloro-3-nitrobenzaldehyde

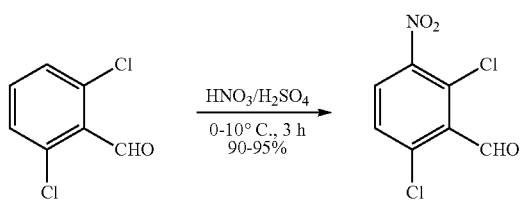 [SMILES: O=Cc1c(Cl)cccc1Cl ; "0-10° C., 3 h90-95%" ; "HNO3/H2SO4" ; O=Cc1c(Cl)ccc([N+](=O)[O-])c1Cl]

To a solution of sulfuric acid ($H_2SO_4$) (5.63 L, 4.5 V) in a round-bottom flask at 0-5° C. was added 2,6-dichlorobenzaldehyde (1.25 kg, 7.10 mol, 1.0 equiv.) in portions at below 15° C. The reaction mass was stirred at 0-5° C. for 30 min. A solution of freshly prepared nitration mixture [Prepared from Conc. $H_2SO_4$ (0.425 L, 0.34 V) and 70% $HNO_3$ (0.85 kg, 13.49 mol, 1.30 equiv.) at 0° C.] was added to the above reaction mixture at below 10° C. [Note: Reaction is slightly exothermic (3-6° C.); so that addition is preferred at lower temperature]. The reaction mixture was stirred at 5-10° C. for 2-3 h. After completion of the reaction (monitored by TLC), it was quenched with ice cold water (18.75 L, 15 V) at below 25° C. Then the reaction mass was allowed warm to room temperature and stirred for 2 h. The solids were isolated by filtration and then were washed with water (2.5 L, 2.0 V). Bulk residual water was removed from the solids by maintaining vacuum filtration for 60-90 min. The crude wet solid was initially dried under air atmosphere; then in a hot air oven at 50-55° C. for 10-12 h (until moisture content is not more than 5.0%) to get the dried title product, 2,6-dichloro-3-nitrobenzaldehyde (1.44 kg, 92% yield) as a yellow solid. $^1$H NMR (400 MHz, $CDCl_3$): δ10.44 (s, 1H), 7.88 (d, J=8.4 Hz, 1H), 7.56 (d, J=8.8 Hz, 1H).

Step 2: Preparation of 2,6-dichloro-3-nitrobenzonitrile

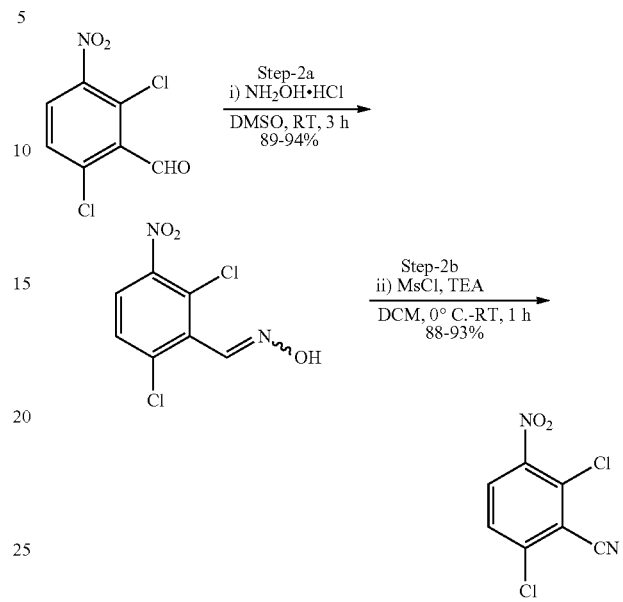

(Step-2a) To a solution of DMSO (5.9 L, 5.0 V)) in a round-bottom flask was added 2,6-dichloro-3-nitrobenzaldehyde (1.17 kg, 5.31 mol, 1.0 equiv.) at room temperature. After being stirred for 30 min at room temperature, hydroxylamine hydrochloride (0.63 kg, 9.04 mol, 1.70 equiv.) was added and the reaction mass was stirred at room temperature for 3 h. After completion of the reaction (monitored by TLC), the reaction mass was quenched by the addition of ice-cold water (18.0 L, 15.0 V) added at a rate sufficient to maintain the temperature below 30° C. (Observation: Solids formed upon water addition). The reaction mass was stirred at room temperature for 60-90 min. The solids were isolated by filtration; washed with water (2.5 L, 2.0 V); followed by washing with a mixture of acetone and hexanes (6.0 L, 1:1 ratio). Bulk residual water was removed from the solids by maintaining vacuum filtration for 60-90 min. The wet solid was initially air dried and then finally dried in a hot air oven at 50-55° C. for 10-12 h (until moisture content was not more than 1.0%) to get the dried target product, 2,6-dichloro-3-nitrobenzaldehyde oxime (1.22 kg, 92% yield) as an off-white solid. The crude product (which contains 10-20% of 2,6-dichloro-3-nitrobenzonitrile) was used directly in the next step without further purification.

(Step-2b) To a stirred solution of the crude oxime (preparation described above, 1.13 kg, 4.80 mol, 1.0 equiv.) in DCM (9.04 L, 8.0 V) at 0-5° C. was added triethylamine ("TEA", 1.02 kg, 10.09 mol, 2.1 equiv.). After being stirred for 5 min, methanesulfonyl chloride (0.60 kg, 5.29 mol, 1.1 equiv.) was added (Observation: An exotherm is noted during the addition) slowly at 15° C. Then the reaction mass was stirred at room temperature for 30-45 min. After completion of the reaction (progress of reaction was monitored by TLC; mobile phase: 20% ethyl acetate in hexanes), the reaction mass was diluted with water (6.78 L, 6.0 V); the organic layer was separated; and the aqueous layer was extracted with DCM (3.4 L, 3.0 V). The combined organic layers were washed with brine (5.65 L, 5.0 V); dried over $Na_2SO_4$; and concentrated under vacuum. The resulting crude solids were triturated with hexanes (4.50 L, 4.0 V) at room temperature. The wet material was dried in a hot air oven at 50-55° C. for 5-6 h to get the dried product, 2,6-dichloro-3-nitrobenzonitrile (0.95 kg, 91% yield) as a yellow solid. $^1$H NMR (400 MHz, CDCl$_3$): δ8.07 (d, J=8.8 Hz, 1H), 7.63 (d, J=8.8 Hz, 1H).

Step 3: Preparation of 4-chloro-7-nitro-1H-indazol-3-amine

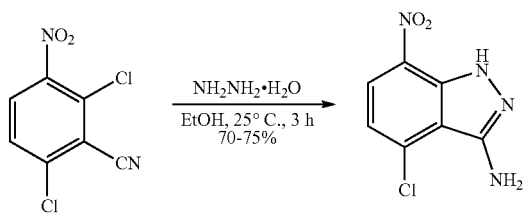 [SMILES: N#Cc1c(Cl)ccc([N+](=O)[O-])c1Cl ; "NH2NH2·H2O" ; "EtOH, 25° C., 3 h70-75%" ; Nc1n[nH]c2c([N+](=O)[O-])ccc(Cl)c12]

To a stirred solution of 2,6-dichloro-3-nitrobenzonitrile (750.0 g, 3.45 mol, 1.0 equiv.) in ethanol (7.5 L, 10.0 V) at 15-20° C. was slowly added hydrazine hydrate (519.0 g, 10.36 mol, 3.0 equiv.) while maintaining the reaction mass below 25° C. (Observation: Addition is slightly exothermic and solid formation will begin upon addition). The reaction mixture temperature was slowly raised to room temperature and then the mixture was stirred for 3 h (Observation: the quantity of solids will increase during this time). After completion of the reaction (monitored by TLC), the mixture was diluted with water (7.5 L, 10.0 V) and further stirred for 1 h at room temperature. The solids were isolated via filtration and then were washed with water (2.25 L, 3.0 V). The wet solid was washed with a 1:1 ratio mixture of acetone (1.875 L, 2.5 V) and hexanes (1.875 L, 2.5 V). Bulk residual water was removed from the solids by maintaining vacuum filtration for 60-90 min. The wet solid was finally dried in a hot air oven for 7-8 h at 50° C. (until moisture content reaches below 1.5%) to get the dried product, 4-chloro-7-nitro-1H-indazol-3-amine (549.0 g, 75% yield) as a brick red-colored solid. $^1$H NMR (400 MHz, CDCl$_3$): δ10.36 (bs, 1H), 8.20 (d, J=8.4 Hz, 1H), 7.07 (d, J=8.40 Hz, 1H), 4.73 (bs, 2H).

Step 4: Preparation of 4-chloro-1-methyl-7-nitro-1H-indazol-3-amine

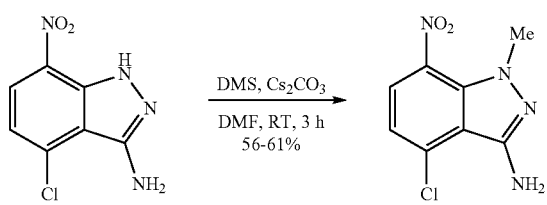

To a stirred solution of 4-chloro-7-nitro-1H-indazol-3-amine (500 g, 0.42 mol, 1.0 equiv.) in DMF (5.0 L, 10.0 V) at 5-10° C. was slowly added cesium carbonate (Cs$_2$CO$_3$) (1.91 kg, 5.88 mol, 2.5 equiv.) while maintaining the reaction mass below 10° C. After being stirred for 5-10 min, dimethyl sulphate (326.3 g, 2.59 mol, 1.1 equiv.) was added while maintaining the reaction mass below 10° C. (Note: Slow addition is preferred for obtaining more favorable regio-selectivity). Then, the reaction temperature was slowly raised to room temperature and stirring was continued an additional 2 h at the same temperature. After completion of the reaction (monitored by TLC), the reaction mass was quenched by the addition of ice-cold water (15.0 L, 30.0 V) and the resulting mixture was then stirred for 6-8 h at room temperature. The solids were isolated via filtration and were then washed with water (1.5 L, 3.0 V). The wet solid was washed with IPA (1.5 L, 3.0 V) followed by hexanes (1.0 L, 2.0 V). Bulk residual water was removed from the solids by maintaining vacuum filtration for 60-90 min. The wet solid was dried in a hot air oven for 7-8 h at 50° C. (until moisture content is below 1.0%). The isolated material, 4-chloro-1-methyl-7-nitro-1H-indazol-3-amine (319.0 g, 60% yield), was used in the next step without further purification. $^1$H NMR (400 MHz, CDCl$_3$): δ7.97 (d, J=8.32 Hz, 1H), 6.97 (d, J=8.24 Hz, 1H), 4.63 (bs, 2H), 3.96 (s, 3H).

Step 5: Preparation of N-(4-chloro-1-methyl-7-nitro-1H-indazol-3-yl)methanesulfonamide

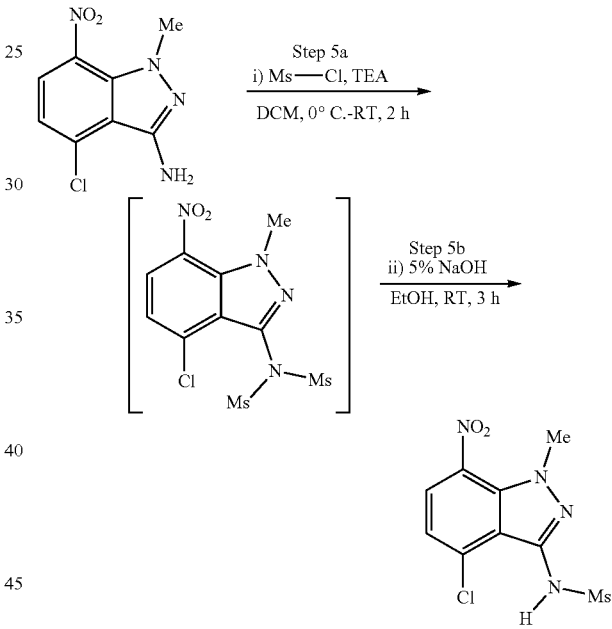

(Step 5a) To a solution of 4-chloro-1-methyl-7-nitro-1H-indazol-3-amine (625.0 g, 2.76 mol, 1.0 equiv.) in DCM (6.25 L, 10.0 V) at 0-5° C. was added triethylamine (TEA) (837.0 g, 8.27 mol, 3.0 equiv.); followed by the addition of 4-dimethylaminopyridine (DMAP) (20.60 g, 0.165 mol, 0.06 equiv.). The reaction mass was stirred for 5-10 min., then methanesulfonyl chloride (MsCl) (790.0 g, 6.89 mol, 2.5 equiv.) added slowly while maintaining the reaction mass below 10° C. The reaction mixture was allowed to warm to room temperature and was then stirred for 1.5-2.0 h. After completion of the reaction (monitored by TLC), the mixture was diluted with water (6.25 L, 10.0 V) and then stirred at room temperature for 15 min. The organic layer was separated, and the aqueous layer was extracted with DCM (6.25 L, 10.0 V). The combined organic layers were washed with brine (1.25 L, 2.0 V), dried over Na$_2$SO$_4$ and concentrated to get the crude solids. The solids were triturated with hexanes (1.25 L, 2.0 V) at room temperature to obtain the intermediate, N-(4-chloro-1-methyl-7-nitro-1H- indazol-3-yl)-N-(methylsulfonyl)methanesulfonamide, which was used directly in the next step.

(ii) To a stirred solution of N-(4-chloro-1-methyl-7-nitro-1H-indazol-3-yl)-N-(methylsulfonyl)methanesulfonamide (prepared above) in ethanol (10.5 L, 20.0 V) at room temperature was added slowly an aq. 5% NaOH solution (4.38 L, 7.0 V) [Note: Slow addition is preferred via dropping funnel]. The reaction mass was stirred at the same temperature for 3 h. After completion of the reaction (monitored by TLC) [Sample preparation for TLC analysis: ~1.0 ml of sample acidified with aq. 2.0 N HCl to reach the pH: 2-3, extract it with ethyl acetate and analyze the organic layer by TLC], the reaction mass was cooled to 0-5° C. and the pH was adjusted to 2-3 by the addition of aq. 2.0 N HCl (3.13 L, 5.0 V) while maintain the reaction temperature below 10° C. [Note: Precipitation occurred upon addition of HCl and increased with stirring]. The reaction mixture was warmed to room temperature and then stirred for 1.5-2.0 h. Solids obtained were isolated via filtration and were then washed with water (1.25 L, 2.0 V); followed by washing with hexanes (1.25 L, 2.0 V). Bulk residual water was removed from the solids by maintaining vacuum filtration for 60-90 min. The wet material was dried in a hot air oven at 50° C. for 6-7 h (Until the moisture content is below 1.0%) to get the dried product, N-(4-chloro-1-methyl-7-nitro-1H-indazol-3-yl)methanesulfonamide (640.0 g, 76%) as a yellow solid. $^1$H NMR (400 MHz, CDCl$_3$): δ8.05 (d, J=8.32 Hz, 1H), 7.32 (bs, 1H), 7.17 (d, J=8.28 Hz, 1H), 4.15 (s, 3H), 3.45 (s, 3H).

Step 6: Preparation of N-(4-chloro-1-methyl-7-nitro-1H-indazol-3-yl)-N-(4-methoxybenzyl)methanesulfonamide

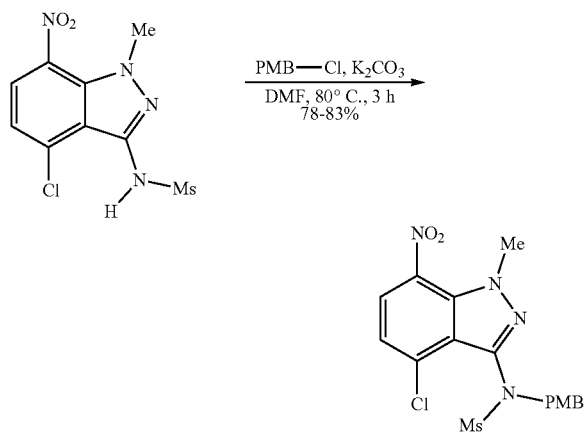

To a mixture of N-(4-chloro-1-methyl-7-nitro-1H-indazol-3-yl)methanesulfonamide (635.0 g, 2.08 mol, 1.0 equiv.) and 1-(chloromethyl)-4-methoxybenzene (359.0 g, 2.30 mol, 1.1 equiv.) in DMF (6.35 L, 10.0 V) at room temperature was added potassium carbonate (374.7 g, 2.70 mol, 1.3 equiv.). The reaction mixture was heated to 80-90° C. and maintained at that temperature for 3 h. After completion of the reaction (monitored by TLC), the mixture was poured into ice cold water (19.05 L, 30.0 V) [Note: Slow quenching with vigorous stirring is preferred to avoid clumping as the product precipitates]. The resulting solids were isolated via filtration and washed with water (1.90 L, 3.0 V); then the solids were washed with hexanes (1.27 L, 2.0 V). Bulk residual water was removed from the solids by maintaining vacuum filtration for 60-90 min. The isolated solid was dissolved in Ethyl acetate (12.7 L, 20.0 V) and charcoal was added (63.5 g). The mixture was heated to 60-70° C. and then stirred for 30-45 min. at that temperature. The mixture was filtered while still hot (40-50° C.) through a pad of Celite and the Celite pad was then extracted with ethyl acetate (3.17 L, 5.0 V). The combined filtrates were concentrated to dryness under reduced pressure at below 50° C. Ethyl acetate (0.635 L, 1.0 V) was added to the solids at room temperature. The resultant solid suspension was stirred for 30 min. The solids were isolated via filtration and then were washed with hexanes (1.27 L, 2.0 V). Residual water was removed from the solids by maintaining vacuum filtration for 45-60 min. to afford the product N-(4-chloro-1-methyl-7-nitro-1H-indazol-3-yl)-N-(4-methoxybenzyl)methane sulfonamide (705.0 g, 80% yield) as a yellow solid. $^1$H NMR (400 MHz, CDCl$_3$): δ7.99 (d, J=8.24 Hz, 1H), 7.27 (d, J=8.68 Hz, 2H), 7.19 (d, J=8.24 Hz, 1H), 6.80 (d, J=8.44 Hz, 2H), 4.95-4.76 (m, 2H), 4.17 (s, 3H), 3.76 (s, 3H), 3.01 (s, 3H).

Step 7: Preparation of N-(7-Amino-4-chloro-1-methyl-1H-indazol-3-yl)-N-(4-methoxybenzyl)methanesulfonamide

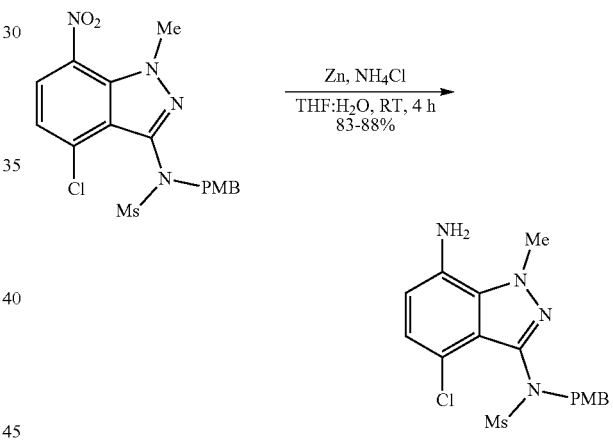

To a stirred suspension of zinc powder (540.0 g, 8.23 mol, 10.0 equiv.) in a mixture of THF (3.50 L, 10.0 V) and water (7.0 L, 20.0 V) at room temperature was added ammonium chloride (NH$_4$Cl) (449.0 g, 8.23 mol, 10.0 equiv.). To the mixture was added N-(4-chloro-1-methyl-7-nitro-1H-indazol-3-yl)-N-(4-methoxybenzyl)methanesulfonamide (350 g, 0.823 mol, 1.0 equiv.) in THF (7.0 L, 20.0 V). The reaction mixture was stirred at room temperature for 3-4 h. After completion of the reaction (monitored by in-process TLC/HPLC), the mixture was diluted with ethyl acetate (3.5 L, 10.0 V) and water (1.12 L, 2.5 V). The mixture was stirred for 15 min. The reaction mass was filtered through a pad of Celite bed washing with ethyl acetate (1.75 L, 5.0 V). The bi-phasic filtrate was collected, and the phases were separated. The aqueous layer was extracted with ethyl acetate (3.50 L, 10.0 V). The combined organic layers were washed with brine (3.50 L, 10 V), dried over Na$_2$SO$_4$, and then concentrated in vacuo to afford a crude solid. To the crude product was added MTBE (3.25 L, 10 V) and the suspension was stirred for 30 min at room temperature. The solids were isolated by filtration. Bulk residual water was removed from the solids by maintaining vacuum filtration for 30-45 min. The wet product was dried in a hot air oven (50° C.) for 2 h to afford the title product, N-(7-amino-4-chloro-1-methyl-1H-indazol-3-yl)-N-(4-methoxybenzyl)methanesulfonamide (276.0 g, 85% yield) as off-white solid. $^1$H NMR (400 MHz, CDCl$_3$): δ7.29-7.26 (m, 2H), 6.86-6.79 (m, 2H), 6.42 (d, J=7.80 Hz, 1H), 4.99-4.70 (m, 2H), 4.25 (s, 3H), 3.77 (s, 5H), 2.98 (s, 3H).

Preparation of N-(7-amino-4-chloro-1-(2,2-difluoroethyl)-1H-indazol-3-yl)-N-(4-methoxybenzyl)methanesulfonamide

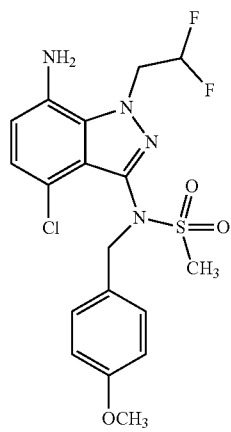 [SMILES: COc1ccc(CN(c2nn(CC(F)F)c3c(N)ccc(Cl)c23)S(C)(=O)=O)cc1]

Synthesis Scheme:

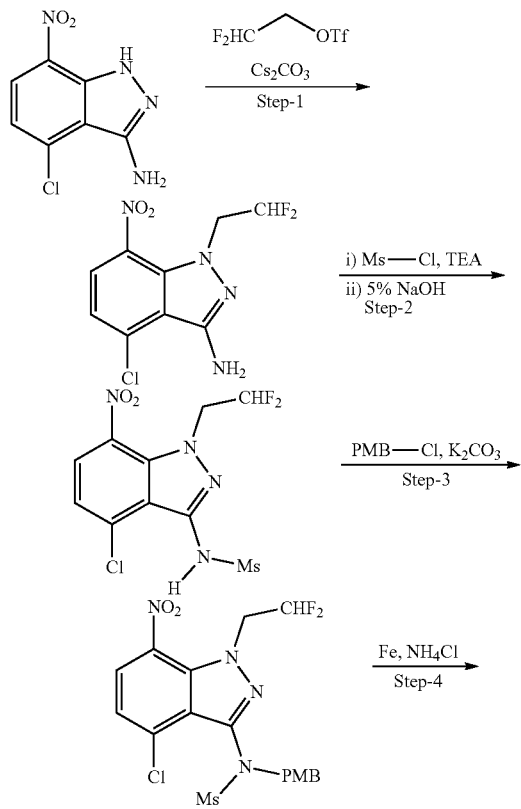

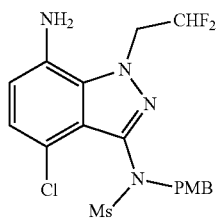

Step 1: Preparation of 4-chloro-1-(2,2-difluoroethyl)-7-nitro-1H-indazol-3-amine

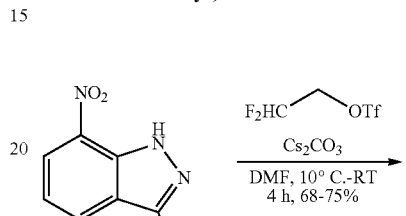

To a stirred solution of 4-chloro-7-nitro-1H-indazol-3-amine (180 g, 0.85 mol, 1.0 equiv.) in DMF (1.8 L, 10.0 V) at 10-15° C. was added cesium carbonate (Cs$_2$CO$_3$) (551 g, 1.70 mol, 2.0 equiv.) at a rate necessary to maintaining the reaction mass below 20° C. The mixture was stirred for 5-10 min, then to the stirred mixture at 10-15° C. was added 2,2-difluoroethyl trifluoromethanesulfonate (133 mL, 0.93 mol, 1.1 equiv.) at a rate necessary to maintain the reaction mass below 20° C. (Note: Slow addition is preferred to obtain more favorable regio-selectivity). The reaction mass was allowed to slowly warm to room temperature and was then stirred at the same temperature for 3 h. After completion of the reaction (monitored by TLC), the reaction mass was quenched by the addition of ice-cold water (5.4 L, 30.0 V) and the resulting mixture was allowed to warm to room temperature with stirring for 6-8 h. The solids were isolated via filtration and were then washed with water (540 mL, 3.0 V). The wet solid was washed with hexanes (0.9 L, 5.0 V). Bulk residual water was removed from the solids by maintaining vacuum filtration for 60-90 min. The wet solid was dried in a hot air oven for 7-8 h at 50° C. (until the moisture content was below 1.0%). The isolated material, 4-chloro-1-(2,2-difluoroethyl)-7-nitro-1H-indazol-3-amine (160 g, 71% yield), was used in the next step without further purification. $^1$H NMR (400 MHz, CDCl$_3$): δ8.05 (d, J=8.4 Hz, 1H), 7.07 (d, J=8.4 Hz, 1H), 6.00 (tt, J$_1$=3.9 Hz, J$_2$=7.7 Hz, 1H), 4.76-4.84 (m, 4H).

Step 2: Preparation of N-(4-chloro-1-(2,2-difluoroethyl)-7-nitro-1H-indazol-3-yl)methane sulfonamide

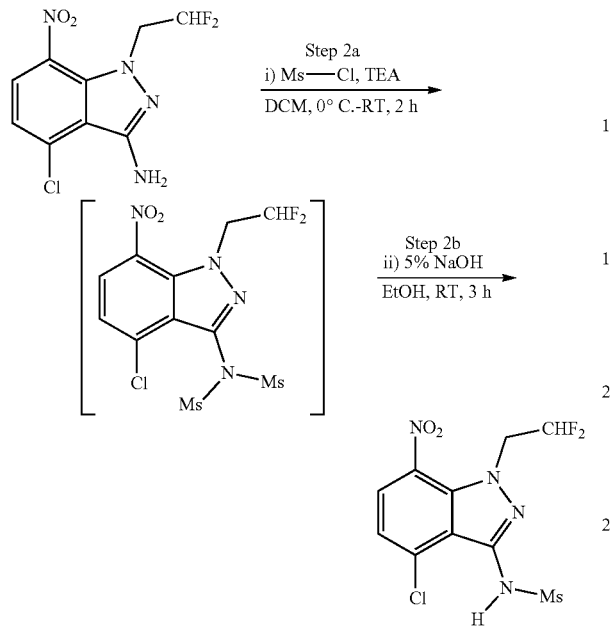

Step 2a: To a solution of 4-chloro-1-(2,2-difluoroethyl)-7-nitro-1H-indazol-3-amine (170.0 g, 0.96 mol, 1.0 equiv.) in DCM (1.7 L, 10.0 V) at 0-5° C. was added triethyl amine (264 mL, 2.88 mol, 3.0 equiv.), followed by 4-dimethylaminopyridine (3.4 g, 0.048 mol, 0.05 equiv.). The reaction mass was stirred for 5-10 min., then methanesulfonyl chloride (120 mL, 2.4 mol, 2.5 equiv.) was added slowly while maintaining the reaction mass below 10° C. The reaction mixture was allowed to warm to room temperature and then was stirred for 1.5-2.0 h. After completion of the reaction (monitored by TLC), the mixture was diluted with water (1.7 L, 10.0 V) and then stirred at room temperature for 15 min. The organic layer was separated, and the aqueous layer was extracted with DCM (1.7 L, 10.0 V). The combined organic layers were washed with 10% brine solution (340 mL, 2.0 V), dried over $Na_2SO_4$ and concentrated to afford the product as a crude solid. The solids were triturated with hexanes (340 mL, 2.0 V) at room temperature to obtain N-(4-chloro-1-(2,2-difluoroethyl)-7-nitro-1H-indazol-3-yl)-N-(methylsulfonyl) methanesulfonamide which was used directly in the next step.

Step 2b: To a stirred solution of N-(4-chloro-1-(2,2-difluoroethyl)-7-nitro-1H-indazol-3-yl)-N-(methylsulfonyl) methanesulfonamide (entirety of material prepared above) in ethanol (1.7 L, 10.0 V) at room temperature was added slowly aq. 5% NaOH solution (1.19 L, 7.0 V) [Note: Slow addition is preferred via dropping funnel]. The reaction mass was stirred at the same temperature for 3 h. After completion of the reaction [Sample preparation for TLC analysis: an aliquot of reaction solution (~1 mL) was acidified with aq. 2.0 N HCl to reach the pH 2-3; then the mixture was extracted with ethyl acetate and organic layer was analyzed by TLC], the reaction mass was cooled to 0-5° C. and the pH was adjusted to 2-3 by the addition of aq. 2.0 N HCl (~850 mL, 5.0 V) at below 10° C. [Note: Precipitation occurred upon addition of HCl and the solids increased gradually with stirring]. The reaction mixture was warmed to room temperature and then stirred for 1.5-2.0 h. Solids obtained were isolated via filtration and were then washed with water (340 mL, 2.0 V); followed by washing with hexanes (340 mL, 2.0 V). Bulk residual water was removed from the solids by maintaining vacuum filtration for 60-90 min. The wet material was dried in a hot air oven at 50° C. for 6-7 h (until the moisture content was below 1.0%) to afford the dried product, N-(4-chloro-1-(2,2-difluoroethyl)-7-nitro-1H-indazol-3-yl)methanesulfonamide (170.0 g, 75%) as a yellow solid. $^1$H NMR (400 MHz, $CDCl_3$): δ8.15 (d, J=8.3 Hz, 1H), 7.52 (bs, 1H), 7.24 (d, J=8.3 Hz, 1H), 6.04 (tt, $J_1$=3.7 Hz, $J_2$=7.9 Hz, 1H), 5.02 (td, $J_1$=3.9 Hz, $J_2$=14.3 Hz, 2H), 3.42 (s, 4H).

Step 3: Preparation of N-(4-chloro-1-(2,2-difluoroethyl)-7-nitro-1H-indazol-3-yl)-N-(4-methoxy benzyl)methanesulfonamide

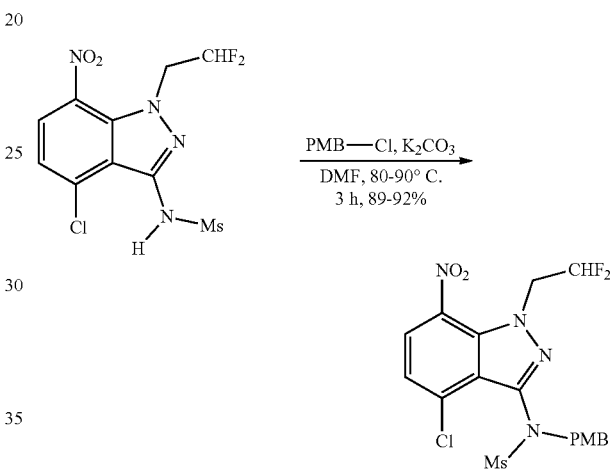

To a mixture of N-(4-chloro-1-(2,2-difluoroethyl)-7-nitro-1H-indazol-3-yl)methane sulfonamide (160.0 g, 0.45 mol, 1.0 equiv.) and 1-(chloromethyl)-4-methoxybenzene (67.6 mL, 0.5 mol, 1.1 equiv.) in DMF (1.6 L, 10.0 V) at room temperature was added potassium carbonate (93.8 g, 0.59 mol, 1.3 equiv.). The reaction mixture was heated to 80-90° C. and maintained at the same temperature for 3 h. After completion of the reaction (monitored by TLC), the mixture was poured into ice cold water (4.8 L, 60.0 V) [Note: Slow quenching with vigorous stirring is preferred to avoid clumping as the product precipitates]. The resulting solids were isolated via filtration and washed with water (480 mL, 3.0 V); then the solids were washed with hexanes (320 mL, 2.0 V). Bulk residual water was removed from the solids by maintaining vacuum filtration for 1-2 h. The isolated solid was dissolved in ethyl acetate (1.6 L, 10.0 V) and charcoal was added (16.0 g). The mixture was heated to 60-70° C. and then stirred for 30-45 min. at that temperature. The mixture was filtered while hot (40-50° C.) through a pad of Celite and the Celite pad was then extracted with ethyl acetate (800 mL, 5.0 V). The combined filtrates were concentrated to dryness under reduced pressure at below 50° C. To the resulting solids at room temperature was added ethyl acetate (160 mL, 1.0 V). The suspension was stirred for 30 min. The solids were isolated via filtration and then were washed with hexanes (320 mL, 2.0 V). Residual water was removed from the solids by maintaining vacuum filtration for 45-60 min. to afford the product N-(4-chloro-1-(2,2-difluoroethyl)-7-nitro-1H-indazol-3-yl)-N-(4-methoxybenzyl)methanesulfonamide (180.0 g, 92% yield) as a yellow solid. $^1$H NMR (400 MHz, CDCl$_3$): δ8.06 (d, J=8.4 Hz, 1H), 7.52 (bs, 1H), 7.27-7.21 (m, 4H), 6.77 (d, J=8.3 Hz, 2H), 6.01 (tt, J$_1$=3.8 Hz, J$_2$=7.9 Hz, 1H), 5.12-4.78 (m, 4H), 3.74 (s, 3H), 3.02 (s, 3H).

Step 4: Preparation of N-(7-amino-4-chloro-1-(2,2-difluoroethyl)-1H-indazol-3-yl)-N-(4-methoxybenzyl)methanesulfonamide

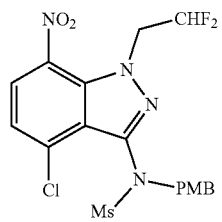

To a stirred suspension of iron powder (76.5 g, 1.37 mol, 5.0 equiv.) in a mixture of EtOH (650 mL, 5.0 V) and water (780 mL, 6.0 V) at room temperature was added ammonium chloride (118.0 g, 2.18 mol, 8.0 equiv.). To the mixture was added N-(4-chloro-1-(2,2-difluoroethyl)-7-nitro-1H-indazol-3-yl)-N-(4-methoxybenzyl)methanesulfonamide (130 g, 0.27 mol, 1.0 equiv.) in EtOH (520 mL, 4.0 V). The reaction mixture was heated to 60° C. and then stirred for 2 h. After completion of the reaction (monitored by in-process TLC/HPLC), the mixture was cooled to room temperature and diluted with ethyl acetate (1.3 L, 10.0 V) and water (390 mL, 3.0 V). The mixture was stirred for 15 min. The mixture was filtered through a pad of Celite and the Celite pad was then extracted with ethyl acetate (650 mL, 5.0 V). The bi-phasic filtrate was partitioned, and the organic phase was reserved while the aqueous layer was extracted with ethyl acetate (650 mL, 5.0 V). The combined organic layers were washed with brine (1.3 L, 10 V), dried over Na$_2$SO$_4$, and then concentrated in vacuo to afford a crude solid. To the crude product was added MTBE (650 mL, 5.0 V) and the suspension was stirred for 30 min. at room temperature. The solids were isolated via filtration. Bulk residual water was removed from the solids by maintaining vacuum filtration for 30-45 min. The wet product was dried in a hot air oven (50° C.) for 2 h to afford the title compound N-(7-amino-4-chloro-1-(2,2-difluoroethyl)-1H-indazol-3-yl)-N-(4-methoxy benzyl)methanesulfonamide (100.0 g, 70% yield) as off-white solid. $^1$H NMR (400 MHz, CDCl$_3$): δ7.21 (d, J=8.5 Hz, 2H), 6.87 (d, J=8.4 Hz, 1H), 6.78 (d, J=8.5 Hz, 2H), 6.52 (d, J=8.3 Hz, 1H), 6.01 (tt, J$_1$=3.8 Hz, J$_2$=7.7 Hz, 1H), 4.98-4.69 (m, 4H), 3.75 (s, 3H), 2.98 (s, 3H).

Preparation of N-(7-amino-4-chloro-1-(2,2-difluoroethyl)-1H-indazol-3-yl)-N-(4-methoxybenzyl)cyclopropanesulfonamide

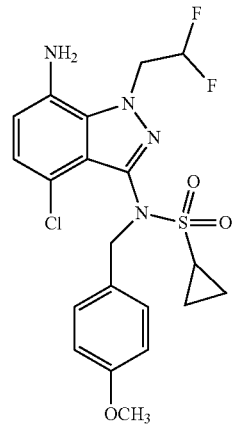 [SMILES: COc1ccc(CN(c2nn(CC(F)F)c3c(N)ccc(Cl)c23)S(=O)(=O)C2CC2)cc1]

Synthesis Scheme:

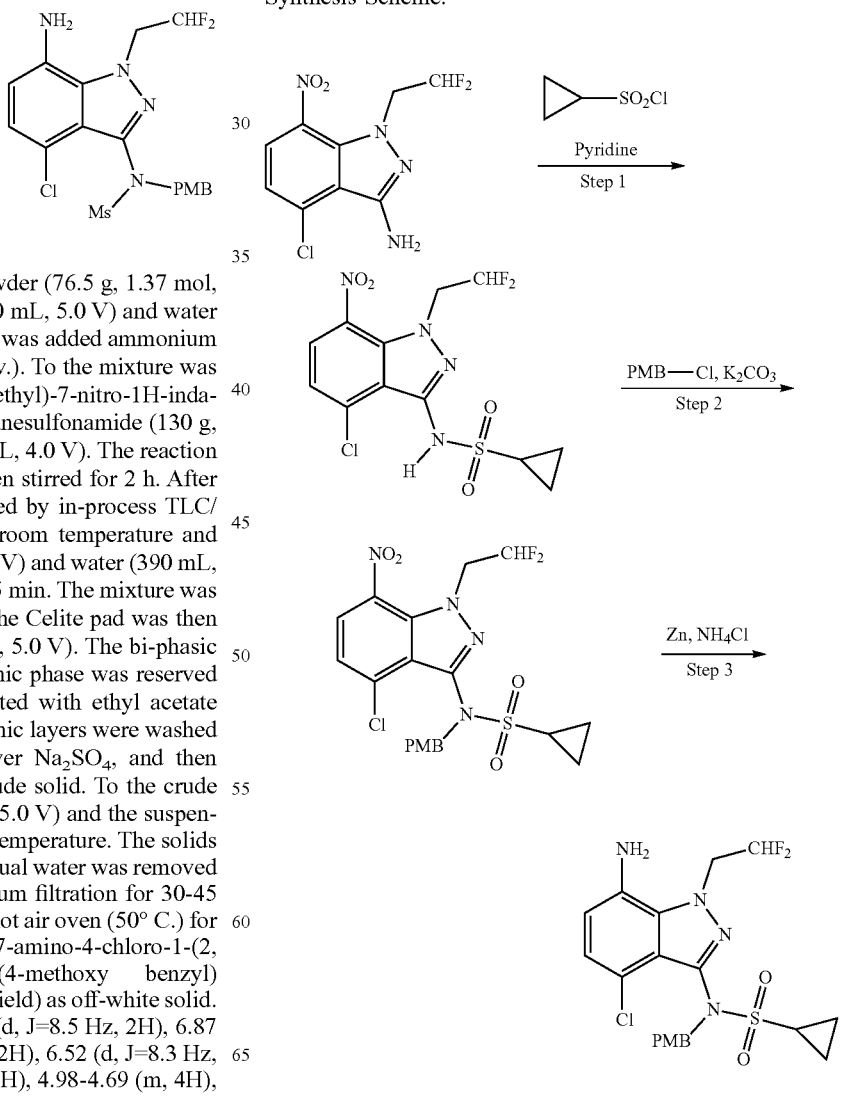

Step 1: Preparation of N-(4-chloro-1-(2,2-difluoro-ethyl)-7-nitro-1H-indazol-3-yl)cyclopropanesulfonamide

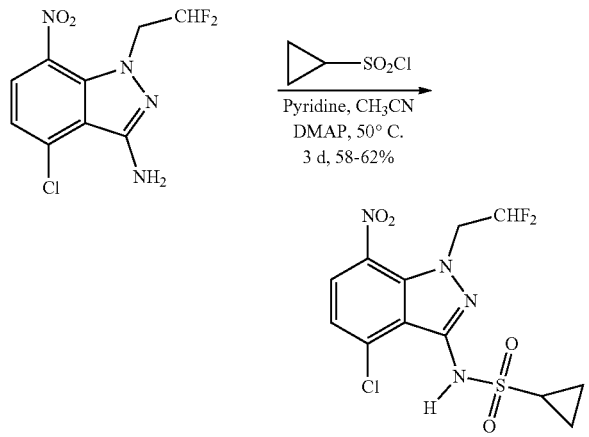

To a stirred solution of 4-chloro-1-(2,2-difluoroethyl)-7-nitro-1H-indazol-3-amine (150.0 g, 0.54 mol, 1.0 equiv.) in acetonitrile (600 mL, 4.0 V) at room temperature was added pyridine (600 mL, 4.0 V), followed by the addition of 4-dimethylaminopyridine (30.0 g, 0.27 mol, 0.5 equiv.). The reaction mass was stirred for 5-10 min., then cyclopropylsulfonyl chloride (114 mL, 1.08 mol, 2.0 equiv.) was added at room temperature. The reaction mixture was heated to 50° C. and then stirred at that temperature for 3 days. After completion of the reaction (monitored by TLC), the mixture was cooled to room temperature and diluted with water (1.5 L, 10.0 V) and ethyl acetate (1.5 L, 10.0 V), then stirred at room temperature for 15 min. The organic layer was separated, and the aqueous layer was extracted with EtOAc (300 mL, 2.0 V). The combined organic layers were washed with aq. 1.0 N HCl (600 mL, 4.0 V), followed by 10% brine solution (1.5 L, 10.0 V). The organic layer was dried over Na$_2$SO$_4$, filtered, and then concentrated under reduced pressure to afford N-(4-chloro-1-(2,2-difluoroethyl)-7-nitro-1H-indazol-3-yl)cyclopropanesulfonamide (124.0 g, 61%) as a viscous liquid. $^1$H NMR (400 MHz, CDCl$_3$): δ8.11 (d, J=8.5 Hz, 1H), 7.25 (d, J=8.5 Hz, 1H), 6.04 (tt, J$_1$=3.8 Hz, J$_2$=7.7 Hz, 1H), 5.05 (td, J$_1$=3.8 Hz, J$_2$=14.4 Hz, 2H), 3.06-3.00 (m, 1H), 1.65-1.42 (m, 2H), 1.19-1.13 (m, 2H).

Step 2: Preparation of N-(4-chloro-1-(2,2-difluoro-ethyl)-7-nitro-1H-indazol-3-yl)-N-(4-methoxyben-zyl)cyclopropanesulfonamide

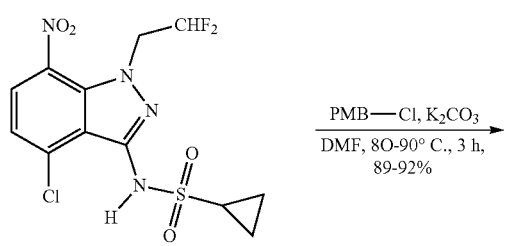

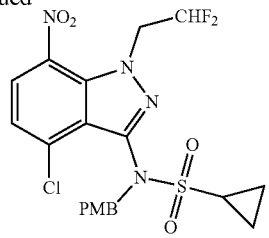

To a mixture of N-(4-chloro-1-(2,2-difluoroethyl)-7-nitro-1H-indazol-3-yl)cyclopropanesulfonamide (100.0 g, 0.20 mol, 1.0 equiv.) and 1-(chloromethyl)-4-methoxybenzene (39.2 mL, 0.22 mol, 1.1 equiv.) in DMF (1.0 L, 10.0 V) at room temperature was added potassium carbonate (128 g, 0.33 mol, 1.3 equiv.). The reaction mixture was heated to 80-90° C. and maintained at that temperature for 3 h. After completion of the reaction (monitored by TLC), the mixture was poured into ice cold water (3.0 L, 30.0 V) [Note: Slow quenching with vigorous stirring is preferred to avoid clumping as the product precipitates]. The resulting solids were isolated via filtration and washed with water (300 mL, 3.0 V); then the solids were washed with hexanes (300 mL, 3.0 V). Bulk residual water was removed from the solids by maintaining vacuum filtration for 1-2 h. The wet solid was dissolved in ethyl acetate (500 mL, 5.0 V) and charcoal was added (10.0 g). The mixture was heated to 60-70° C. and then stirred for 30-45 minutes at that temperature. The mixture was filtered while hot (40-50° C.) through a pad of Celite and the Celite pad was extracted with ethyl acetate (500 mL, 5.0 V). The combined filtrates were concentrated to dryness under reduced pressure at below 50° C. to afford N-(4-chloro-1-(2,2-difluoroethyl)-7-nitro-1H-indazol-3-yl)-N-(4-methoxy-benzyl)cyclopropanesulfonamide (122.0 g, 92% yield) as a yellow solid. $^1$H NMR (400 MHz, CDCl$_3$): δ8.05 (d, J=8.6 Hz, 1H), 7.26-7.22 (m, 3H), 6.73 (d, J=8.5 Hz, 2H), 5.98 (tt, J$_1$=3.7 Hz, J$_2$=7.8 Hz, 1H), 5.09-4.88 (m, 4H), 3.72 (s, 3H), 2.65-2.60 (m, 1H), 1.15-1.06 (m, 2H), 0.89-0.86 (m, 2H).

Step 3: Preparation of N-(7-amino-4-chloro-1-(2,2-difluoroethyl)-1H-indazol-3-yl)-N-(4-methoxyben-zyl)cyclopropanesulfonamide

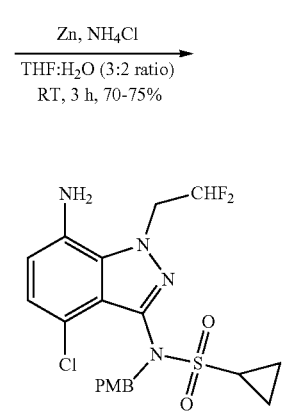

To a stirred suspension of zinc powder (156.0 g, 2.4 mol, 10.0 equiv.) in a mixture of THF (1.2 L, 10.0 V) and water (2.4 L, 20.0 V) at room temperature was added ammonium chloride (129.0 g, 2.40 mol, 10.0 equiv.). To the mixture was added N-(4-chloro-1-(2,2-difluoroethyl)-7-nitro-1H-indazol-3-yl)-N-(4-methoxybenzyl)cyclopropanesulfonamide (120 g, 0.2 mol, 1.0 equiv.) in THF (2.4 L, 20.0 V). The reaction mixture was stirred at room temperature for 2 h. After completion of the reaction (monitored by in-process TLC/HPLC), the mixture was diluted with ethyl acetate (1.2 L, 10.0 V) and water (360 mL, 3.0 V). The mixture was stirred for 15 min. The mixture was filtered through Celite and the Celite pad was extracted with ethyl acetate (600 mL, 5.0 V). The bi-phasic filtrate was partitioned, and the organic phase was reserved while the aqueous layer was extracted with ethyl acetate (600 mL, 5.0 V). The combined organic layers were washed with 10% brine solution (1.2 L, 10 V), dried over $Na_2SO_4$, filtered, and then concentrated in vacuo to afford a crude solid. To the crude product was added MTBE (600 mL, 5.0 V) and the suspension was stirred for 30-45 min. at room temperature. The solids were isolated by filtration and then bulk residual water was removed from the solids by maintaining vacuum filtration for 30-45 min. The wet product was dried in a hot air oven (50° C.) for 2 h to afford the product, N-(7-amino-4-chloro-1-(2,2-difluoroethyl)-1H-indazol-3-yl)-N-(4-methoxybenzyl)cyclopropanesulfonamide (81.0 g, 73% yield) as off-white solid. $^1$H NMR (400 MHz, $CDCl_3$): δ7.25 (d, J=8.5 Hz, 2H), 6.93 (d, J=8.4 Hz, 1H), 6.75 (d, J=8.3 Hz, 2H), 6.57 (d, J=8.4 Hz, 1H), 6.03 (tt, $J_1$=3.7 Hz, $J_2$=7.9 Hz, 1H), 4.80-4.95 (m, 4H), 3.74 (s, 3H), 2.67-2.61 (m, 1H), 1.14 (d, J=2.4 Hz, 2H), 0.96 (d, J=2.3 Hz, 2H).

Preparation of N-(7-amino-4-chloro-1-(2,2,2-trifluoroethyl)-1H-indazol-3-yl)-N-(4-methoxybenzyl)methanesulfonamide

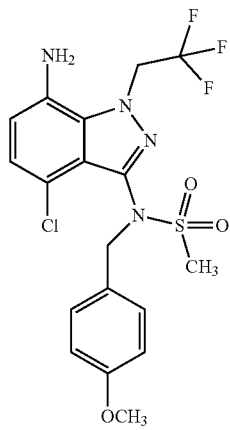 [SMILES: COc1ccc(CN(c2nn(CC(F)(F)F)c3c(N)ccc(Cl)c23)S(C)(=O)=O)cc1]

Synthesis Scheme:

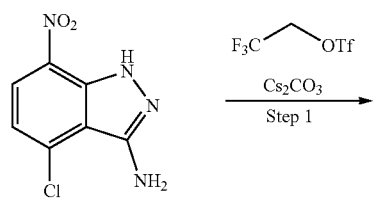

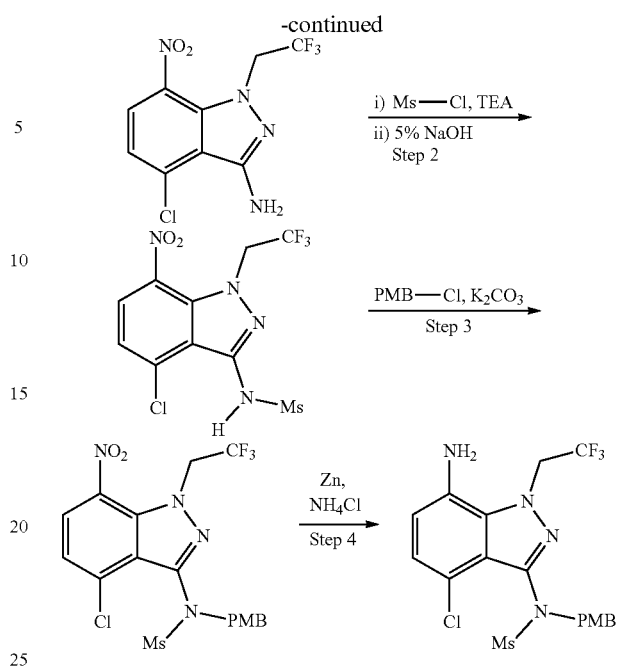

Step 1: Preparation of 4-chloro-7-nitro-1-(2,2,2-trifluoroethyl)-1H-indazol-3-amine

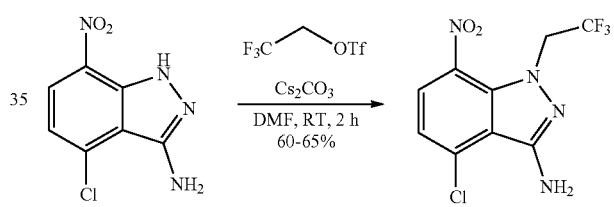

To a stirred solution of 4-chloro-7-nitro-1H-indazol-3-amine (50 g, 0.23 mol, 1.0 equiv.) in DMF (500 mL, 10.0 V) at 10-15° C. was added cesium carbonate ($Cs_2CO_3$) (153.3 g, 0.47 mol, 2.0 equiv.) at a rate sufficient to maintain the reaction mass below 20° C. The mixture was stirred for 5-10 min, then to the stirred mixture at 10-15° C. was added 2,2,2-trifluoroethyl trifluoromethanesulfonate (60.18 g, 0.26 mol, 1.1 equiv.) at a rate sufficient to maintain the reaction mass below 20° C. (Note: slow addition is preferred for obtaining more favorable regio-selectivity). The reaction mass was allowed to slowly warm to room temperature and was then stirred at the same temperature for 2 h. After completion of the reaction (monitored by TLC), the reaction mass was quenched via the addition of ice-cold water (1.5 L, 30.0 V) and the resulting mixture was allowed to warm to room temperature with stirring for 6-8 h. The solids were isolated via filtration and were then washed with water (150 mL, 3.0 V). The wet solid was washed with hexanes (250 mL, 5.0 V) and then bulk residual water was removed from the solids by maintaining vacuum filtration for 60-90 min. The wet solid was dried in a hot air oven for 7-8 h at 50° C. (until the moisture content was below 1.0%). The isolated material, 4-chloro-7-nitro-1-(2,2,2-trifluoroethyl)-1H-indazol-3-amine (45.0 g, 60% yield) was used directly in the next step without further purification. $^1$H-NMR (400 MHz, $CDCl_3$): δ8.09 (d, J=8.40 Hz, 1H), 7.12 (d, J=8.40 Hz, 1H), 5.14 (q, J=8.52 Hz, 2H), 4.77 (bs, H).

Step 2: Preparation of N-(4-chloro-7-nitro-1-(2,2,2-trifluoroethyl)-1H-indazol-3-yl)methanesulfonamide

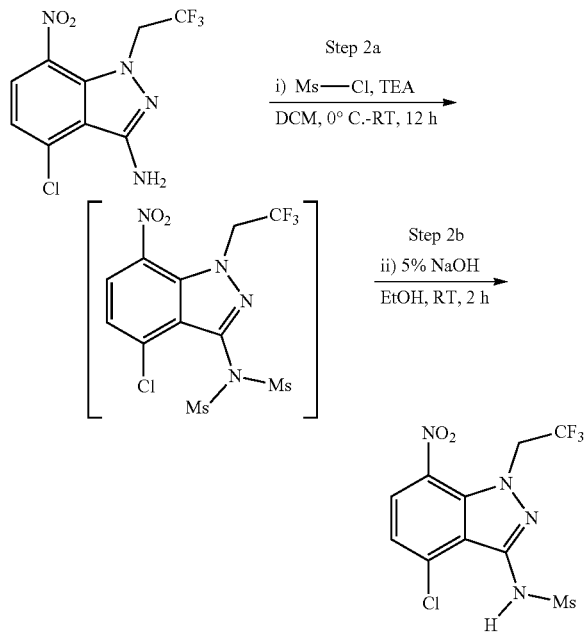

(Step 2a): To a solution of 4-chloro-7-nitro-1-(2,2,2-trifluoroethyl)-1H-indazol-3-amine (20.0 g, 0.068 mol, 1.0 equiv.) in DCM (200 mL, 10.0 V) at 0-5° C. was added triethylamine (29.0 mL, 0.204 mol, 3.0 equiv.), followed by the addition of 4-dimethylaminopyridine (415 mg, 0.03 mol, 0.05 equiv.). The reaction mass was stirred for 5-10 min., then to the mixture was added methanesulfonyl chloride (13.25 mL, 0.17 mol, 2.5 equiv) at a rate sufficient to maintain the reaction mass below 10° C. The reaction mixture was allowed to warm to room temperature with stirring for 12 h. After completion of the reaction (monitored by TLC), the mixture was diluted with water (200 mL, 10.0 V) and then stirred at room temperature for 15 min. The organic layer was separated, and the aqueous layer was extracted with DCM (200 mL, 10.0 V). The combined organic layers were washed with 10% brine solution (60 mL, 3.0 V), dried over Na$_2$SO$_4$, filtered, and concentrated to afford the crude solids. The solids were triturated with hexanes (60 mL, 3.0 V) at room temperature to obtain the intermediate, N-(4-chloro-7-nitro-1-(2,2,2-trifluoroethyl)-1H-indazol-3-yl)-N-(methylsulfonyl)methanesulfonamide, which was used directly in the next step.

(Step 2b): To a stirred solution of N-(4-chloro-7-nitro-1-(2,2,2-trifluoroethyl)-1H-indazol-3-yl)-N-(methylsulfonyl)methanesulfonamide (entirety of the material prepared above) in ethanol (200 mL, 10.0 V) at room temperature was added slowly aq. 5% NaOH solution (140 mL, 7.0 V) [Note: Slow addition is preferred via dropping funnel]. The reaction mass was stirred at the same temperature for 2 h. After completion of the reaction [Sample preparation for TLC analysis: An aliquot of the reaction solution (~1.0 ml) was acidified by the addition of aq. 2.0 N HCl to reach pH 2-3; then the mixture was extracted with ethyl acetate and the organic phase was analyzed by TLC], the reaction mass was cooled to 0-5° C. and the pH was adjusted to 2-3 by the addition of aq. 2.0 N HCl (100 mL, 5.0 V) while maintain the temperature below 10° C. [Note: Precipitation occurred upon addition of HCl and increased with stirring]. The reaction mixture was warmed to room temperature and then stirred for 1.5-2.0 h. The solids were isolated via filtration and were then washed with water (60 mL, 3.0 V), followed by washing with hexanes (60 mL, 3.0 V). Bulk residual water was removed from the solids by maintaining vacuum filtration for 60-90 min. The wet material was dried in a hot air oven at 50° C. for 6-7 h (until the moisture content was below 1.0%) to afford N-(4-chloro-7-nitro-1-(2,2,2-trifluoroethyl)-1H-indazol-3-yl)methanesulfonamide (22.1 g, 87%) as a yellow solid. $^1$H NMR (400 MHz, CDCl$_3$): δ8.19 (d, J=8.40 Hz, 1H), 7.56 (bs, 1H), 7.30 (d, J=8.40 Hz, 1H), 5.34 (q, J=8.30 Hz, 2H), 3.46 (s, 3H).

Step 3: Preparation of N-(4-chloro-7-nitro-1-(2,2,2-trifluoroethyl)-1H-indazol-3-yl)-N-(4-methoxybenzyl)methanesulfonamide

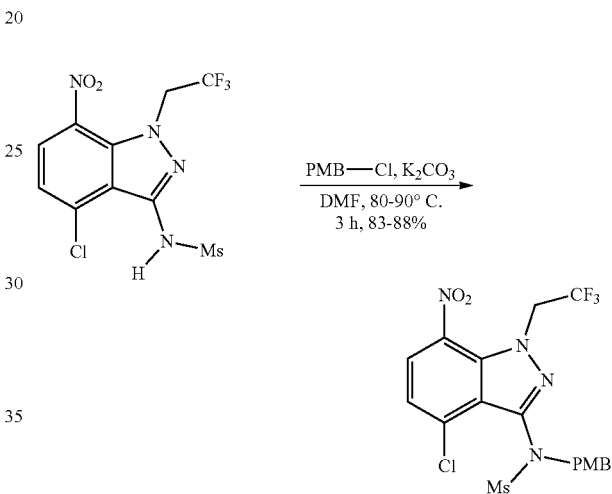

To a mixture of N-(4-chloro-7-nitro-1-(2,2,2-trifluoroethyl)-1H-indazol-3-yl)methanesulfonamide (50.0 g, 0.134 mol, 1.0 equiv.) and 1-(chloromethyl)-4-methoxybenzene (23.0 g, 0.147 mol, 1.1 equiv.) in DMF (500 mL, 10.0 V) at room temperature was added potassium carbonate (27.8 g, 0.201 mol, 1.5 equiv.). The reaction mixture was heated to 80-90° C. and maintained at that temperature for 3 h. After completion of the reaction (monitored by TLC), the mixture was poured into ice cold water (2.0 L, 40.0 V) [Note: Slow quenching with vigorous stirring is preferred to avoid clumping as the product precipitates]. The resulting solids were isolated via filtration and washed with water (150 mL, 3.0 V); then the solids were washed with hexanes (150 mL, 3.0 V). Bulk residual water was removed from the solids by maintaining vacuum filtration for 1-2 h. The solids were dissolved in ethyl acetate (500 mL, 10.0 V) and to the solution was added charcoal (5.0 g). The mixture was heated to 60-70° C. and then stirred at that temperature for 30-45 min. The mixture was filtered while hot (40-50° C.) through a pad of Celite and the Celite pad was extracted with ethyl acetate (250 mL, 5.0 V). The combined filtrate was concentrated to dryness under reduced pressure at below 50° C. The solids were combined with ethyl acetate (50 mL, 1.0 V) at room temperature. The resulting suspension was stirred for 30 min. The solids were isolated via filtration and then were washed with hexanes (100 mL, 2.0 V). Residual water was removed from the solids by maintaining vacuum filtration for 45-60 min. to afford N-(4-chloro-7-nitro-1-(2,2,2-trifluoroethyl)-1H-indazol-3-yl)-N-(4-methoxybenzyl)methanesulfonamide (56.0 g, 85% yield) as a yellow solid. $^1$H NMR (400 MHz, CDCl$_3$): δ8.12 (d, J=8.36 Hz, 1H), 7.31 (d, J=8.36 Hz, 1H), 7.22 (d, J=8.44 Hz, 2H), 6.77 (d, J=8.44 Hz, 2H), 5.50-5.25 (m, 2H), 4.94-4.79 (m, 2H), 3.75 (s, 3H), 3.02 (s, 3H).

Step 4: Preparation of N-(7-amino-4-chloro-1-(2,2,2-trifluoroethyl)-1H-indazol-3-yl)-N-(4-methoxybenzyl)methanesulfonamide

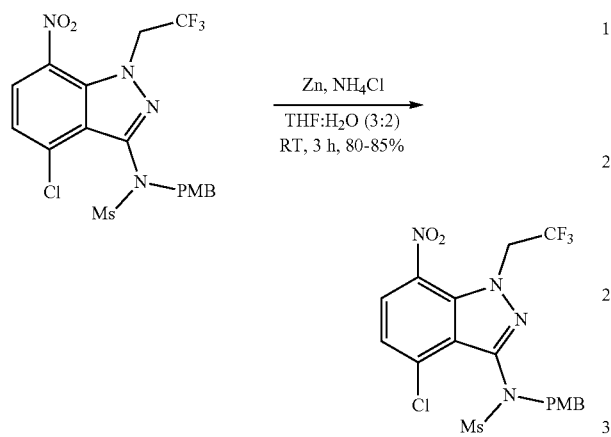

To a stirred suspension of zinc powder (66.31 g, 1.01 mol, 10.0 equiv.) in THF (500 mL, 10.0 V) and water (1.0 L, 20.0 V) at room temperature was added ammonium chloride (54.78 g, 1.01 mol, 10.0 equiv.). To the mixture was added a solution of N-(4-chloro-7-nitro-1-(2,2,2-trifluoroethyl)-1H-indazol-3-yl)-N-(4-methoxybenzyl)methanesulfonamide (50.0 g, 0.101 mol, 1.0 equiv.) in THF (1.0 L, 20.0 V). The reaction mixture was stirred at room temperature for 3 h. After completion of the reaction (monitored by in-process TLC/HPLC), the mixture was diluted with ethyl acetate (1.0 L, 20.0 V) and water (250 mL, 5.0 V). The mixture was stirred for 15 min. The mixture was filtered through a pad of Celite and the Celite pad was extracted with ethyl acetate (250 mL, 5.0 V). The bi-phasic filtrate was partition and the organic layer was reserved while the aqueous layer was extracted with ethyl acetate (500 mL, 10.0 V). The combined organic layers were washed with 10% brine solution (500 mL, 10.0 V), dried over Na$_2$SO$_4$, filtered, and then concentrated in vacuo to afford a crude solid. To the crude product was added MTBE (250 mL, 5.0 V) and the resulting suspension was stirred for 30 min. at room temperature. The solids were isolated by filtration and then bulk residual water was removed from the solids by maintaining vacuum filtration for 30-45 min. The wet product was dried in a hot air oven (50° C.) for 2 h to afford the title product N-(7-amino-4-chloro-1-(2,2,2-trifluoroethyl)-1H-indazol-3-yl)-N-(4-methoxybenzyl)methanesulfonamide (39.0 g, 83% yield) as off-white solid. $^1$H NMR (400 MHz, CDCl$_3$): δ7.25 (d, J=8.48 Hz, 2H), 6.98 (d, J=7.80 Hz, 1H), 6.79 (d, J=8.48 Hz, 2H), 6.66 (d, J=7.84 Hz, 1H), 5.35-4.75 (m, 4H), 3.77 (s, 3H), 3.56 (bs, 2H), 2.98 (s, 3H).

Preparation of N-[(6P)-7-{2-[(1S)-1-amino-2-(3,5-difluorophenyl)ethyl]-7-hydroxy-4-oxo-3H,4H-pyrido[2,3-d]pyrimidin-3-yl}-4-chloro-1-(2,2-difluoroethyl)-1H-indazol-3-yl]-N-[(4-methoxyphenyl)methyl]methane sulfonamide Scheme:

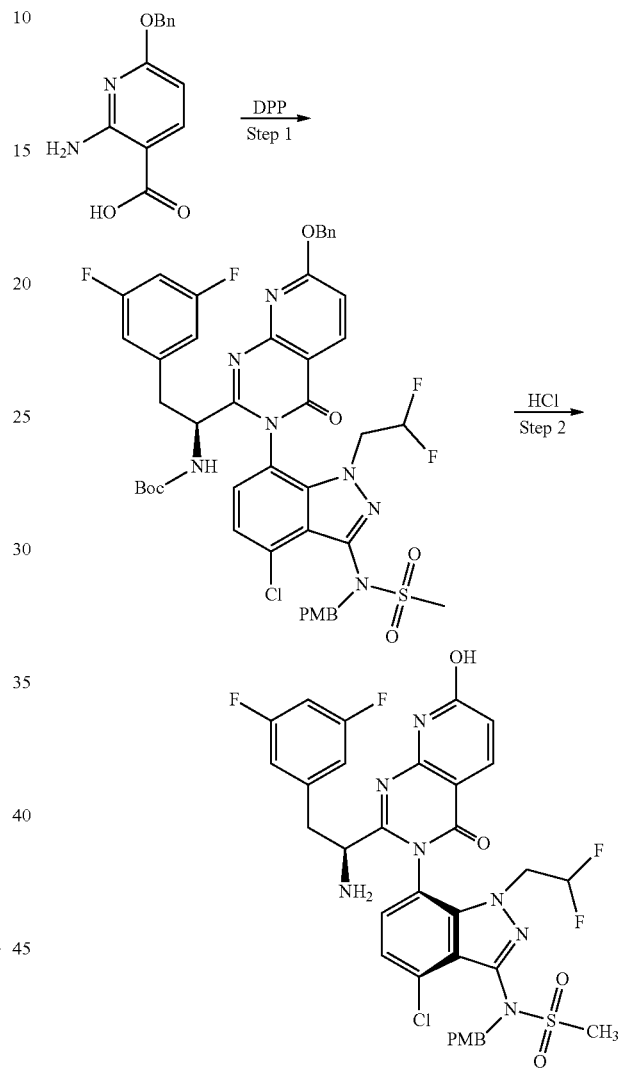

Step 1:

A mixture of 2-amino-6-(benzyloxy)nicotinic acid (1.0 g, 4.09 mmol), (S)-2-((tert-butoxycarbonyl)amino)-3-(3,5-difluorophenyl)propanoic acid (1.234 g, 4.09 mmol), N-(7-amino-4-chloro-1-(2,2-difluoroethyl)-1H-indazol-3-yl)-N-(4-methoxybenzyl)methanesulfonamide (1.821 g, 4.09 mmol) and diphenyl phosphonate (3.14 mL, 16.38 mmol) in Pyridine (11.70 mL) in a pressure vial was heated at 75° C. for 9 hours, then cooled to rt. The reaction mixture was diluted with EtOAc and then washed with aq. 0.5 M citric acid, dried over Na$_2$SO$_4$ and concentrated in vacuo. The resulting residue was purified on silica gel (330 g RediSep column) using 0-45% ethyl acetate in hexanes over 15 CV, then at 45% EtOAc for 10 CV. The desired fractions were pooled and concentrated to afford a pale yellow foamy solid (1.0 g, 26%), tert-butyl (1-(7-(benzyloxy)-3-(4-chloro-1-(2, 2-difluoroethyl)-3-(N-(4-methoxybenzyl)methylsulfonamido)-1H-indazol-7-yl)-4-oxo-3,4-dihydropyrido[2,3-d]pyrimidin-2-yl)-2-(3,5-difluorophenyl)ethyl)carbamate (4 stereoisomers) wherein tert-butyl N-[(1S)-1-[(3P, 3P)-7-(benzyloxy)-3-[4-chloro-1-(2,2-difluoroethyl)-3-{N-[(4-methoxyphenyl)methyl]methanesulfonamido}indazol-7-yl]-4-oxopyrido[2,3-d]pyrimidin-2-yl]-2-(3,5-difluorophenyl)ethyl]carbamate is the major component. LC/MS: m/z=936.15[M+1]⁺.

Step 2:

TFA (1.646 mL, 21.36 mmol) was added to a solution of tert-butyl (1-(7-(benzyloxy)-3-(4-chloro-1-(2,2-difluoroethyl)-3-(N-(4-methoxybenzyl)methylsulfonamido)-1H-indazol-7-yl)-4-oxo-3,4-dihydropyrido[2,3-d]pyrimidin-2-yl)-2-(3,5-difluorophenyl)ethyl)carbamate (Product from Step 1, 1.0 g, 1.068 mmol) in dichloromethane (5.3 ml). The mixture was stirred at ambient temperature for 1 h. The resultant pale-yellow solution was concentrated in vacuo. The resulting residue was taken up in ethyl acetate, washed with sat. NaHCO₃, dried over Na₂SO₄ and concentrated in vacuo to give a yellow solid. The solid was subject to silica gel chromatography (two 80 g RediSep Gold columns connected in series) using 10-100% ethyl acetate in hexanes over 20 CV, then at 100% ethyl acetate for 5 CV and finally at 12.5% methanol in ethyl acetate for 3 CV to separate the atropisomers. Two peaks contain the desired product mass; the first eluting isomer (major) was collected and concentrated in vacuo to afford a white fluffy solid (0.8 g). This material was further subjected to chiral HPLC using a Chiralpak IC (5 microns, 30 mm×250 mm) column (preconditioned with ammonium acetate) eluting isocratic with 60:40 n-heptane:ethanol. Fractions of the major peak were pooled and concentrated to afford N-[(6P)-7-{2-[(1S)-1-amino-2-(3,5-difluorophenyl)ethyl]-7-hydroxy-4-oxo-3H,4H-pyrido[2,3-d]pyrimidin-3-yl}-4-chloro-1-(2,2-difluoroethyl)-1H-indazol-3-yl]-N-[(4-methoxyphenyl)methyl] methanesulfonamide as a white solid (410 mg), a single stereoisomer. LC/MS: m/z=746.05[M+1]⁺.

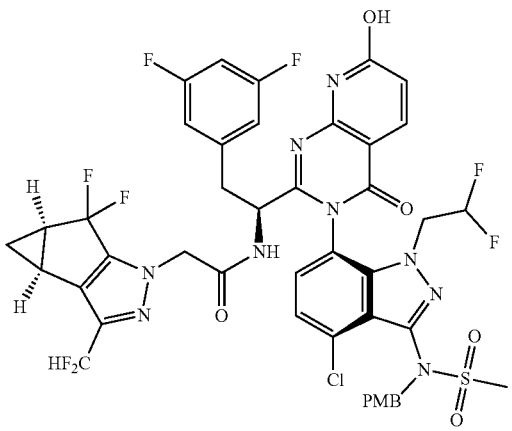

N—((S)-1-((3P)-3-(4-chloro-1-(2,2-difluoroethyl)-3-(N-(4-methoxybenzyl)methylsulfonamido)-1H-indazol-7-yl)-7-hydroxy-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide To a stirred solution of N-[(6P)-7-{2-[(1S)-1-amino-2-(3,5-difluorophenyl)ethyl]-7-hydroxy-4-oxo-3H,4H-pyrido[2,3-d]pyrimidin-3-yl}-4-chloro-1-(2,2-difluoroethyl)-1H-indazol-3-yl]-N-[(4-methoxyphenyl)methyl] methanesulfonamide (0.20 g, 0.268 mmol) in Tetrahydrofuran (2 mL):N,N-Dimethylformamide (0.5 mL) were added 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (0.071 g, 0.268 mmol), HATU (0.102 g, 0.268 mmol) and DIPEA (0.117 mL, 0.670 mmol). The reaction mixture was stirred for 1 h at rt, then the mixture was directly subjected to silica gel column chromatography (40 g RediSep column) using 10-100% ethyl acetate in hexanes over 20 CV. The desired fractions were pooled and concentrated to give N—((S)-1-((3P)-3-(4-chloro-1-(2,2-difluoroethyl)-3-(N-(4-methoxybenzyl)methylsulfonamido)-1H-indazol-7-yl)-7-hydroxy-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (0.27 g, 100% yield) as a pale yellow solid. LC/MS: m/z=992.10[M+1]⁺.

EXAMPLE 13

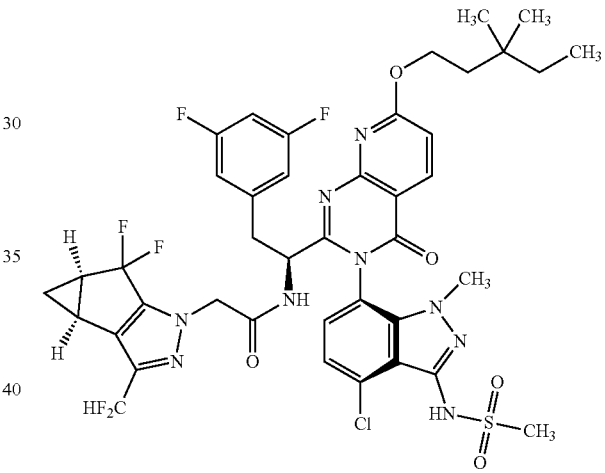

N—((S)-1-((3P)-3-(4-chloro-1-methyl-3-(methylsulfonamido)-1H-indazol-7-yl)-7-((3,3-dimethylpentyl)oxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide A solution of diisopropyl (E)-diazene-1,2-dicarboxylate (0.019 mL, 0.096 mmol) in THF (0.2 mL) was added dropwise to a solution of N—((S)-1-((3P)-3-(4-chloro-3-(N-(4-methoxybenzyl)methylsulfonamido)-1-methyl-1H-indazol-7-yl)-7-hydroxy-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (0.03 g, 0.032 mmol), 3,3-dimethylpentan-1-ol (0.011 g, 0.096 mmol), and triphenylphosphine (0.027 g, 0.102 mmol) in THF (0.8 mL). The reaction mixture was stirred for 18 h at ambient temperature and then concentrated in vacuo. The residue was taken up in DCM (0.5 mL) and TFA (0.25 mL). Triflic acid (8.48 μL, 0.096 mmol) was added. The resultant purple solution was stirred for 1 h and then concentrated in vacuo. The crude product was taken up in ethyl acetate (1.5 mL) and washed with saturated aqueous NaHCO₃ (1 mL). The organic layer was concentrated and then purified by preparatory HPLC using the following conditions: Column: Zorbax Eclipse Plus C18, 21.2×100 mm, 5 µm particles; Solvent A=0.1% Formic Acid in 100% Water. Solvent B=Acetonitrile. Flow Rate=40 mL/min. Start % B=66 Final % B=86. Gradient Time=8 min, then a 2 min hold at 98% B. Wavelength=215 and 254 nm. ESI+Range: 150 to 1500 dalton. Sample was loaded at 66% B and afforded N—((S)-1-((3P)-3-(4-chloro-1-methyl-3-(methylsulfonamido)-1H-indazol-7-yl)-7-((3,3-dimethylpentyl)oxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (0.0056 g, 6.08 µmol, 19% yield). ¹H NMR (500 MHz, METHANOL-d₄) δ ppm 8.45-8.52 (m, 1H), 7.26-7.32 (m, 1H), 7.16-7.23 (m, 1H), 7.00-7.08 (m, 1H), 6.54-6.84 (m, 4H), 4.82-4.87 (m, 1H), 4.51-4.65 (m, 4H), 3.59-3.63 (m, 3H), 3.44-3.51 (m, 1H), 3.21-3.24 (m, 3H), 3.08-3.17 (m, 1H), 2.39-2.48 (m, 2H), 1.80-1.86 (m, 2H), 1.35-1.46 (m, 3H), 1.00-1.04 (m, 7H), 0.94-0.97 (m, 3H). LC/MS retention time=1.64 min; m/z=920.3[M+H]⁺ Column: Acquity BEH C18, 2.1×30 mm, 1.7 µm particles; Solvent A=0.1% Formic acid in 100% Water. Solvent B=0.1% Formic Acid in 100% Acetonitrile. Flow Rate=0.8 mL/min. Start % B=5. Final % B=95. Gradient Time=1.7 min, then a 0.2 min hold at 95% B. Wavelength=215 and 254 nm. ESI+ Range: 150 to 1500 Dalton. System: Agilent 1290 Infinity II.

EXAMPLE 14

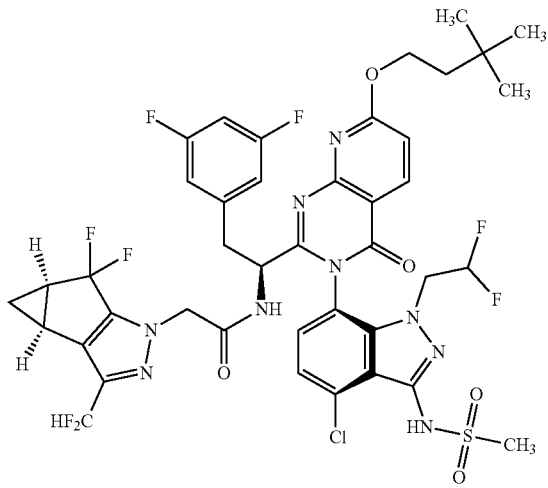

N—((S)-1-((3P)-3-(4-chloro-1-(2,2-difluoroethyl)-3-(methylsulfonamido)-1H-indazol-7-yl)-7-(3,3-dimethylbutoxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide A solution of diisopropyl (E)-diazene-1,2-dicarboxylate (0.030 mL, 0.151 mmol) in THF (0.2 mL) was added dropwise to a mixture of N—((S)-1-((3P)-3-(4-chloro-1-(2,2-difluoroethyl)-3-(N-(4-methoxybenzyl)methylsulfonamido)-1H-indazol-7-yl)-7-hydroxy-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (0.05 g, 0.050 mmol), 3,3-dimethylbutan-1-ol (0.015 g, 0.151 mmol) and triphenylphosphine (0.042 g, 0.161 mmol) in THF (0.8 mL) at ambient temperature. The reaction mixture was stirred for 18 h and then concentrated in vacuo. The residue was taken up in DCM (0.5 mL) and TFA (0.25 mL). Triflic acid (0.013 mL, 0.151 mmol) was added. The resultant purple solution was stirred for 1 h and concentrated in vacuo. The crude residue was taken up in ethyl acetate (1.5 mL) and washed with saturated aqueous NaHCO₃ (1 mL). The organic layer was concentrated in vacuo and purified by preparatory HPLC using the following conditions: Column: Zorbax Eclipse Plus C18, 21.2×100 mm, 5 µm particles; Solvent A=0.1% Formic Acid in 100% Water. Solvent B=Acetonitrile. Flow Rate=40 mL/min. Start % B=64.3 Final % B=84.3. Gradient Time=7 min, then a 2 min hold at 98% B. Wavelength=215 and 254 nm. ESI+ Range: 150 to 1500 dalton. Sample was loaded at 64.3% B and afforded (N—((S)-1-((3P)-3-(4-chloro-1-(2,2-difluoroethyl)-3-(methylsulfonamido)-1H-indazol-7-yl)-7-(3,3-dimethylbutoxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (0.0113 g, 0.012 mmol, 23% yield). ¹H NMR (400 MHz, Solvent) δ ppm 8.43-8.50 (m, 1H), 7.36-7.40 (m, 1H), 7.26-7.31 (m, 1H), 7.02-7.07 (m, 1H), 6.54-6.84 (m, 4H), 5.89-6.16 (m, 1H), 4.73-4.79 (m, 1H), 4.59-4.71 (m, 4H), 4.31-4.43 (m, 1H), 3.90-4.02 (m, 1H), 3.39-3.45 (m, 1H), 3.25-3.27 (m, 3H), 3.07-3.13 (m, 1H), 2.40-2.47 (m, 2H), 1.83-1.88 (m, 2H), 1.34-1.40 (m, 1H), 1.07-1.09 (m, 9H), 1.00-1.04 (m, 1H). LC/MS retention time=1.62 min; m/z=956.4[M+H]⁺ Column: Acquity BEH C18, 2.1×30 mm, 1.7 µm particles; Solvent A=0.1% Formic acid in 100% Water. Solvent B=0.1% Formic Acid in 100% Acetonitrile. Flow Rate=0.8 mL/min. Start % B=5. Final % B=95. Gradient Time=1.7 min, then a 0.2 min hold at 95% B. Wavelength=215 and 254 nm. ESI+Range: 150 to 1500 Dalton. System: Agilent 1290 Infinity II.

EXAMPLE 16

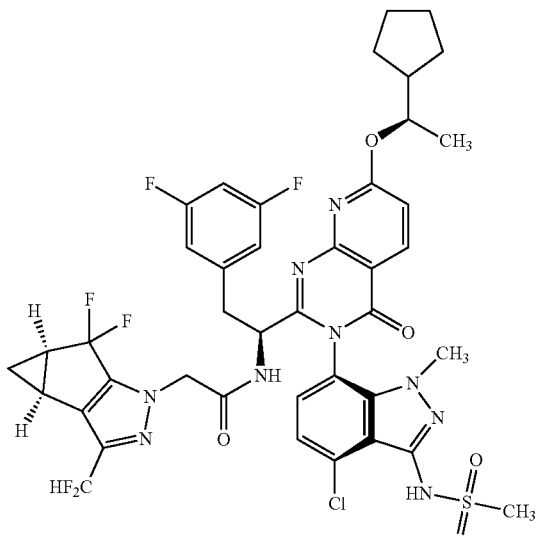

N—((S)-1-((3P)-3-(4-chloro-1-methyl-3-(methyl-sulfonamido)-1H-indazol-7-yl)-7-((R)-1-cyclopenty-lethoxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide A solution of diisopropyl (E)-diazene-1,2-dicarboxylate (0.022 ml, 0.111 mmol) in THF (0.2 mL) was added dropwise to a mixture of N—((S)-1-((3P)-3-(4-chloro-3-(N-(4-methoxybenzyl)methylsulfonamido)-1-methyl-1H-indazol-7-yl)-7-hydroxy-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (0.035 g, 0.037 mmol), (S)-1-cyclopentylethan-1-ol (0.013 g, 0.111 mmol), and triphenylphosphine (0.031 g, 0.119 mmol) in THF (0.8 mL) at ambient temperature. The reaction mixture was stirred for 18 h and then concentrated in vacuo. The residue was taken up in DCM (0.5 mL) and TFA (0.25 mL). Triflic acid (9.89 μL, 0.111 mmol) was added. The resultant purple solution was stirred for 1 h and then concentrated in vacuo. The crude residue was taken up in ethyl acetate (1.5 mL), washed with saturated aqueous NaHCO₃ (1 mL), and concentrated in vacuo. The crude product was purified by preparatory HPLC using the following conditions: Column: Zorbax Eclipse Plus C18, 21.2×100 mm, 5 μm particles; Solvent A=0.1% Formic Acid in 100% Water. Solvent B=Acetonitrile. Flow Rate=40 mL/min. Start % B=64.6 Final % B=84.6. Gradient Time=7 min, then a 2 min hold at 98% B. Wavelength=215 and 254 nm. ESI+Range: 150 to 1500 dalton. Sample was loaded at 65% B and afforded N—((S)-1-((3P)-3-(4-chloro-1-methyl-3-(methylsulfonamido)-1H-indazol-7-yl)-7-((S)-1-cyclopentylethoxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (0.0036 g, 3.72 μmol, 10.03% yield). LC/MS retention time=1.60 min; m/z=918.4[M+H]⁺ Column: Column: Acquity BEH C18, 2.1×30 mm, 1.7 μm particles; Solvent A=0.1% Formic acid in 100% Water. Solvent B=0.1% Formic Acid in 100% Acetonitrile. Flow Rate=0.8 mL/min. Start % B=5. Final % B=95. Gradient Time=1.7 min, then a 0.2 min hold at 95% B. Wavelength=215 and 254 nm. ESI+Range: 150 to 1500 Dalton. System: Agilent 1290 Infinity II.

EXAMPLE 18

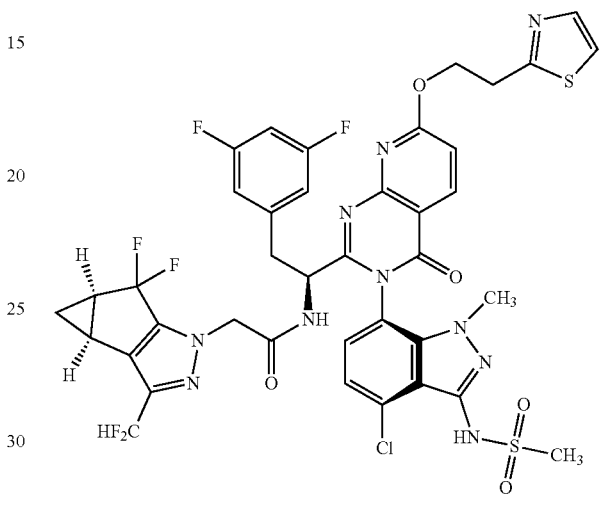

N—((S)-1-((3P)-3-(4-chloro-1-methyl-3-(methyl-sulfonamido)-1H-indazol-7-yl)-4-oxo-7-(2-(thiazol-2-yl)ethoxy)-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide A solution of diisopropyl (E)-diazene-1,2-dicarboxylate (0.026 g, 0.127 mmol) in THF (0.2 mL) was added dropwise to a mixture of N—((S)-1-((3P)-3-(4-chloro-3-(N-(4-methoxybenzyl)methylsulfonamido)-1-methyl-1H-indazol-7-yl)-7-hydroxy-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (0.04 g, 0.042 mmol), 2-(thiazol-2-yl)ethan-1-ol (0.016 g, 0.127 mmol), and triphenylphosphine (0.036 g, 0.136 mmol) in THF (0.8 mL) at ambient temperature. The reaction mixture was stirred for 18 h and then concentrated in vacuo. The residue was taken up in DCM (0.5 mL) and TFA (0.25 mL). Triflic acid (0.011 mL, 0.127 mmol) was added. The resultant purple solution was stirred for 1 h and concentrated in vacuo. The crude residue was taken up in ethyl acetate (1.5 mL), washed with saturated aqueous NaHCO₃ (1 mL), and concentrated in vacuo. The crude product was purified by preparatory HPLC using the following conditions: Column: Zorbax Eclipse Plus C18, 21.2×100 mm, 5 μm particles; Solvent A=0.1% Formic Acid in 100% Water. Solvent B=Acetonitrile. Flow Rate=40 mL/min. Start % B=49.7 Final % B=69.7. Gradient Time=7 min, then a 2 min hold at 98% B. Wavelength=215 and 254 nm. ESI+Range: 150 to 1500 dalton. Sample was loaded at 30% B and afforded N—((S)-1-((3P)-3-(4-chloro-1-methyl-3-(methylsulfonamido)-1H-indazol-7-yl)-4-oxo-7-(2-(thiazol-2-yl)ethoxy)-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (0.0077 g, 8.25 µmol, 19% yield). $^1$H NMR (500 MHz, METHANOL-$d_4$) δ ppm 8.46-8.55 (m, 1H), 7.75-7.79 (m, 1H), 7.53-7.57 (m, 1H), 7.29-7.33 (m, 1H), 7.18-7.24 (m, 1H), 7.04-7.09 (m, 1H), 6.54-6.83 (m, 4H), 4.92-4.97 (m, 3H), 4.52-4.64 (m, 2H), 3.64-3.70 (m, 2H), 3.58-3.63 (m, 3H), 3.43-3.51 (m, 1H), 3.22-3.26 (m, 3H), 3.08-3.16 (m, 1H), 2.37-2.50 (m, 2H), 1.32-1.41 (m, 1H), 0.97-1.04 (m, 1H). LC/MS retention time=1.66 min; m/z=933.4[M+H]$^+$ (Column: Zorbax Eclipse Plus C18, 2.1×50 mm, 1.7 µm particles; Solvent A=0.1% Formic acid in 100% Water. Solvent B=0.1% Formic Acid in 100% Acetonitrile. Flow Rate=1 mL/min. Start % B=5. Final % B=95. Gradient Time=2.1 min, then a 0.3 min hold at 95% B. Wavelength=215 and 254 nm. ESI+Range: 150 to 1500 Dalton.

EXAMPLE 19

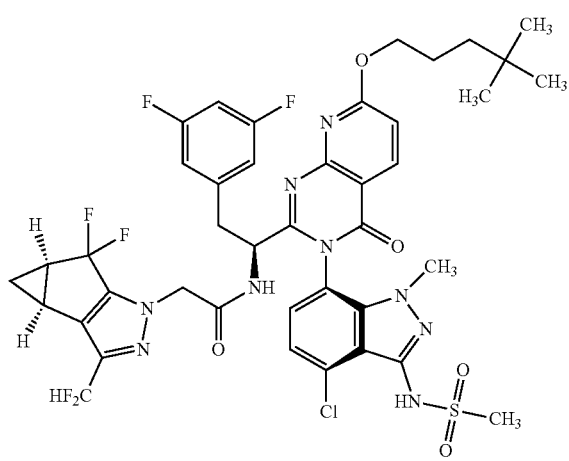

N—((S)-1-((3P)-3-(4-chloro-1-methyl-3-(methylsulfonamido)-1H-indazol-7-yl)-7-((4,4-dimethylpentypoxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide A solution of diisopropyl (E)-diazene-1,2-dicarboxylate (0.019 mL, 0.096 mmol) in THF (0.2 mL) was added dropwise to a mixture of N—((S)-1-((3P)-3-(4-chloro-3-(N-(4-methoxybenzyl)methylsulfonamido)-1-methyl-1H-indazol-7-yl)-7-hydroxy-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (0.03 g, 0.032 mmol), 4,4-dimethylpentan-1-ol (0.011 g, 0.096 mmol), and triphenylphosphine (0.027 g, 0.102 mmol) in THF (0.8 mL) at ambient temperature. The reaction mixture was stirred for 18 h and then concentrated in vacuo. The residue was taken up in DCM (0.5 mL) and TFA (0.25 mL). Triflic acid (8.48 µL, 0.096 mmol) was added. The resultant purple solution was stirred for 1 h and then concentrated in vacuo. The crude residue was taken up in ethyl acetate (1.5 mL), washed with saturated aqueous NaHCO$_3$ (1 mL), and concentrated in vacuo. The crude product was purified by preparatory HPLC using the following conditions: Column: Column: Zorbax Eclipse Plus C18, 21.2×100 mm, 5 µm particles; Solvent A=0.1% Formic Acid in 100% Water. Solvent B=Acetonitrile. Flow Rate=40 mL/min. Start % B=66 Final % B=86. Gradient Time=8 min, then a 2 min hold at 98% B. Wavelength=215 and 254 nm. ESI+Range: 150 to 1500 dalton. Sample was loaded at 66% B and afforded N—((S)-1-((3P)-3-(4-chloro-1-methyl-3-(methylsulfonamido)-1H-indazol-7-yl)-7-((4,4-dimethylpentypoxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (0.0061 g, 6.63 µmol, 21% yield). $^1$H NMR (500 MHz, METHANOL-d4) δ ppm 8.44-8.50 (m, 1H), 7.26-7.33 (m, 1H), 7.17-7.22 (m, 1H), 7.02-7.10 (m, 1H), 6.54-6.83 (m, 4H), 4.84-4.87 (m, 1H), 4.50-4.63 (m, 4H), 3.58-3.64 (m, 3H), 3.45-3.52 (m, 1H), 3.21-3.25 (m, 3H), 3.09-3.16 (m, 1H), 2.39-2.48 (m, 2H), 1.84-1.93 (m, 2H), 1.40-1.47 (m, 2H), 1.35-1.39 (m, 1H), 0.97-1.04 (m, 10H). LC/MS retention time=1.66 min; m/z=920.3[M+H]+ Column: Acquity BEH C18, 2.1×30 mm, 1.7 µm particles; Solvent A=0.1% Formic acid in 100% Water. Solvent B=0.1% Formic Acid in 100% Acetonitrile. Flow Rate=0.8 mL/min. Start % B=5. Final % B=95. Gradient Time=1.7 min, then a 0.2 min hold at 95% B. Wavelength=215 and 254 nm. ESI+Range: 150 to 1500 Dalton. System: Agilent 1290 Infinity II.

EXAMPLE 20

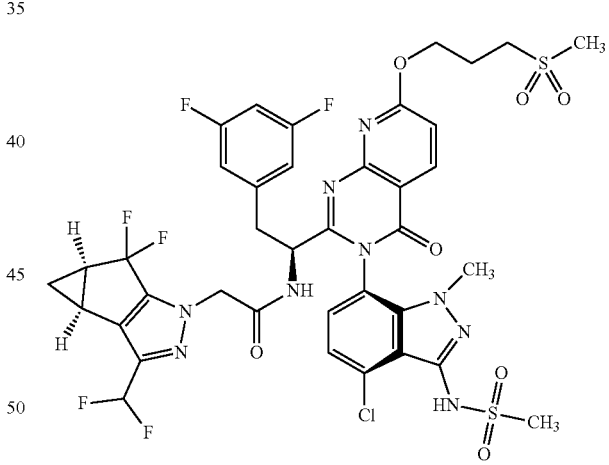

N—((S)-1-((3P)-3-(4-chloro-1-methyl-3-(methylsulfonamido)-1H-indazol-7-yl)-7-(3-(methylsulfonyl)propoxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide A solution of diisopropyl (E)-diazene-1,2-dicarboxylate (0.019 mL, 0.096 mmol) in THF (0.2 mL) was added dropwise to a solution of N—((S)-1-((3P)-3-(4-chloro-3-(N-(4-methoxybenzyl)methylsulfonamido)-1-methyl-1H-indazol-7-yl)-7-hydroxy-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (0.03 g, 0.032 mmol), 3-(methylsulfonyl)propan-1-ol (0.013 g, 0.096 mmol), and triphenylphosphine (0.027 g, 0.102 mmol) in THF (0.8 mL) at ambient temperature. The reaction mixture was stirred for 18 h and then concentrated in vacuo. The crude residue was taken up in DCM (0.5 mL) and TFA (0.25 mL). Triflic acid (8.48 μL, 0.096 mmol) was added. The resultant purple solution was stirred for 1 h and then concentrated in vacuo. The crude residue was taken up in ethyl acetate (1.5 mL), washed with saturated aqueous NaHCO$_3$ (1 mL), and concentrated in vacuo. The crude product was purified by preparatory HPLC using the following conditions: Column: Zorbax Eclipse Plus C18, 21.2× 100 mm, 5 μm particles; Solvent A=0.1% Formic Acid in 100% Water. Solvent B=Acetonitrile. Flow Rate=40 mL/min. Start % B=46 Final % B=64. Gradient Time=8 min, then a 2 min hold at 98% B. Wavelength=215 and 254 nm. ESI+Range: 150 to 1500 dalton. Sample was loaded at 46% B and afforded N—((S)-1-((3P)-3-(4-chloro-1-methyl-3-(methylsulfonamido)-1H-indazol-7-yl)-7-(3-(methylsulfonyl)propoxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (0.004 g, 4.03 μmol, 13% yield). $^1$H NMR (500 MHz, METHANOL-d$_4$) δ ppm 8.48-8.53 (m, 1H), 7.29-7.34 (m, 1H), 7.19-7.24 (m, 1H), 7.08-7.13 (m, 1H), 6.56-6.83 (m, 4H), 4.84-4.86 (m, 1H), 4.69-4.78 (m, 2H), 4.50-4.62 (m, 2H), 3.60-3.64 (m, 3H), 3.38-3.51 (m, 3H), 3.23-3.27 (m, 3H), 3.10-3.16 (m, 1H), 3.03-3.08 (m, 3H), 2.38-2.48 (m, 4H), 1.36-1.40 (m, 1H), 0.99-1.03 (m, 1H). LC/MS retention time=1.26 min; m/z=942.2[M+H]$^+$ Column: Acquity BEH C18, 2.1×30 mm, 1.7 μm particles; Solvent A=0.1% Formic acid in 100% Water. Solvent B=0.1% Formic Acid in 100% Acetonitrile. Flow Rate=0.8 mL/min. Start % B=5. Final % B=95. Gradient Time=1.7 min, then a 0.2 min hold at 95% B. Wavelength=215 and 254 nm. ESI+Range: 150 to 1500 Dalton. System: Agilent 1290 Infinity II.

EXAMPLE 22

N—((S)-1-((3P)-3-(4-chloro-1-(2,2-difluoroethyl)-3-(methylsulfonamido)-1H-indazol-7-yl)-7-(2-cyclopropylethoxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide A solution of diisopropyl (E)-diazene-1,2-dicarboxylate (0.024 mL, 0.121 mmol) in THF (0.2 mL) was added dropwise to a mixture of N—((S)-1-((3P)-3-(4-chloro-1-(2,2-difluoroethyl)-3-(N-(4-methoxybenzyl)methylsulfonamido)-1H-indazol-7-yl)-7-hydroxy-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (0.04 g, 0.040 mmol), 2-cyclopropylethan-1-ol (10.42 mg, 0.121 mmol) and triphenylphosphine (0.034 g, 0.129 mmol) in Tetrahydrofuran (THF) (0.8 mL) at rt. The reaction mixture was stirred for 18 h at ambient temperature. The reaction mixture was stirred for 18 h and then concentrated in vacuo. The crude residue was taken up in DCM (0.5 mL) and TFA (0.25 mL). Triflic acid (8.48 μL, 0.096 mmol) was added. The resultant purple solution was stirred for 1 h and then concentrated in vacuo. The crude residue was taken up in ethyl acetate (1.5 mL), washed with saturated aqueous NaHCO$_3$ (1 mL), and concentrated in vacuo. The crude product was purified by preparatory HPLC using the following conditions: Column: Zorbax Eclipse Plus C18, 21.2× 100 mm, 5 μm particles; Solvent A=0.1% Formic Acid in 100% Water. Solvent B=Acetonitrile. Flow Rate=40 mL/min. Start % B=59.4 Final % B=79.4. Gradient Time=7 min, then a 2 min hold at 98% B. Wavelength=215 and 254 nm. ESI+Range: 150 to 1500 dalton. Sample was loaded at 59.4% B and afforded N—((S)-1-((3P)-3-(4-chloro-1-(2,2-difluoroethyl)-3-(methylsulfonamido)-1H-indazol-7-yl)-7-(2-cyclopropylethoxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (0.0041 g, 4.14 μmol, 10% yield). $^1$H NMR (500 MHz, METHANOL-d$_4$) δ ppm 8.42-8.53 (m, 1H) 7.21-7.40 (m, 2H) 7.00-7.13 (m, 1H) 6.55-6.83 (m, 4H) 5.88-6.18 (m, 1H) 5.50-5.71 (m, 2H) 4.53-4.79 (m, 5H) 4.30-4.42 (m, 1 H) 3.87-4.00 (m, 1H) 3.39-3.45 (m, 1H) 3.23-3.26 (m, 3H) 3.06-3.13 (m, 1H) 2.55-2.62 (m, 1H) 2.40-2.47 (m, 2H) 1.70-1.74 (m, 3H) 1.35-1.39 (m, 2H) 0.99-1.04 (m, 1H). LC/MS retention time=1.40 min; m/z=932.2[M+H]$^+$ Column: Acquity BEH C18, 2.1×30 mm, 1.7 μm particles; Solvent A=0.1% Formic acid in 100% Water. Solvent B=0.1% Formic Acid in 100% Acetonitrile. Flow Rate=0.8 mL/min. Start % B=5. Final % B=95. Gradient Time=1.7 min, then a 0.2 min hold at 95% B. Wavelength=215 and 254 nm. ESI+Range: 150 to 1500 Dalton. System: Agilent 1290 Infinity II.

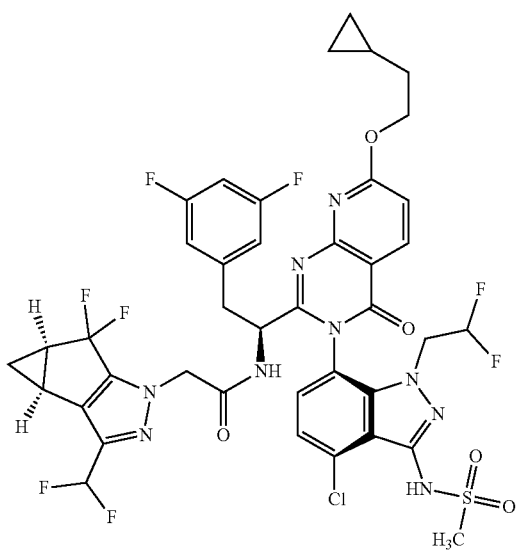

EXAMPLE 23

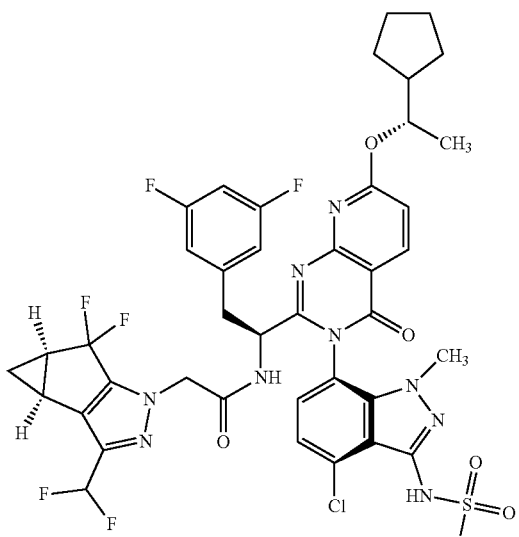

N—((S)-1-((3P)-3-(4-chloro-1-methyl-3-(methyl-sulfonamido)-1H-indazol-7-yl)-7-((S)-1-cyclopenty-lethoxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide A solution of diisopropyl (E)-diazene-1,2-dicarboxylate (0.022 ml, 0.111 mmol) in THF (0.2 mL) was added dropwise to a mixture of N—((S)-1-((3P)-3-(4-chloro-3-(N-(4-methoxybenzyl)methylsulfonamido)-1-methyl-1H-indazol-7-yl)-7-hydroxy-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (0.035 g, 0.037 mmol), (S)-1-cyclopentylethan-1-ol (0.013 g, 0.111 mmol) and triphenylphosphine (0.031 g, 0.119 mmol) in Tetrahydrofuran (THF) (0.8 mL) at ambient temperature. The reaction mixture was stirred for 18 h and then concentrated in vacuo. The crude residue was taken up in DCM (0.5 mL) and TFA (0.25 mL). Triflic acid (8.48 µL, 0.096 mmol) was added. The resultant purple solution was stirred for 1 h and then concentrated in vacuo. The crude residue was taken up in ethyl acetate (1.5 mL), washed with saturated aqueous NaHCO₃ (1 mL), and concentrated in vacuo. The crude product was purified by preparatory HPLC using the following conditions: Column: Zorbax Eclipse Plus C18, 21.2×100 mm, 5 µm particles; Solvent A=0.1% Formic Acid in 100% Water. Solvent B=Acetonitrile. Flow Rate=40 mL/min. Start % B=64.5 Final % B=84.5. Gradient Time=7 min, then a 2 min hold at 98% B. Wavelength=215 and 254 nm. ESI+Range: 150 to 1500 dalton. Sample was loaded at 64.5% B and afforded N—((S)-1-((3P)-3-(4-chloro-1-methyl-3-(methylsulfonamido)-1H-indazol-7-yl)-7-((S)-1-cyclopentylethoxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (0.0022 g, 2.276 µmol, 6% yield). LC/MS retention time=1.60 min; m/z=918.4[M+H]⁺ Column: Column: Acquity BEH C18, 2.1×30 mm, 1.7 µm particles; Solvent A=0.1% Formic acid in 100% Water. Solvent B=0.1% Formic Acid in 100% Acetonitrile. Flow Rate=0.8 mL/min. Start % B=5. Final % B=95. Gradient Time=1.7 min, then a 0.2 min hold at 95% B. Wavelength=215 and 254 nm. ESI+Range: 150 to 1500 Dalton. System: Agilent 1290 Infinity II.

EXAMPLE 24

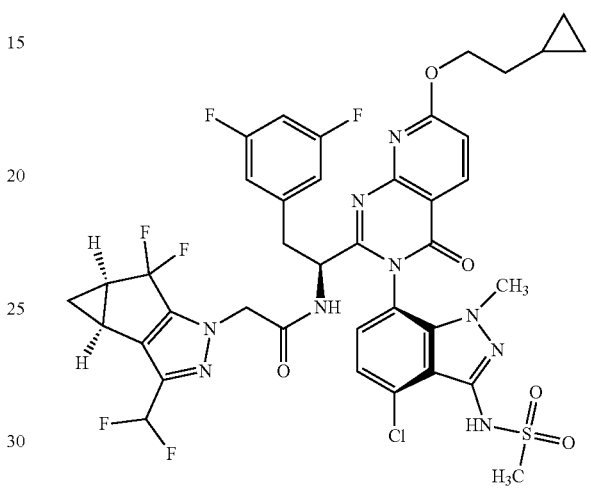

N—((S)-1-((3P)-3-(4-chloro-1-methyl-3-(methyl-sulfonamido)-1H-indazol-7-yl)-7-(2-cyclopropyl-ethoxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide A solution of diisopropyl (E)-diazene-1,2-dicarboxylate (0.023 mL, 0.115 mmol) in THF (0.2 mL) was added dropwise to a mixture of N—((S)-1-((3P)-3-(4-chloro-3-(N-(4-methoxybenzyl)methylsulfonamido)-1-methyl-1H-indazol-7-yl)-7-hydroxy-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (0.036 g, 0.038 mmol), 2-cyclopropylethan-1-ol (9.87 mg, 0.115 mmol) and triphenylphosphine (0.032 g, 0.122 mmol) in Tetrahydrofuran (THF) (0.8 mL) ambient temperature. The reaction mixture was stirred for 18 h and then concentrated in vacuo. The crude residue was taken up in DCM (0.5 mL) and TFA (0.25 mL). Triflic acid (8.48 µL, 0.096 mmol) was added. The resultant purple solution was stirred for 1 h and then concentrated in vacuo. The crude residue was taken up in ethyl acetate (1.5 mL), washed with saturated aqueous NaHCO₃ (1 mL), and concentrated in vacuo. The crude product was purified by preparatory HPLC using the following conditions: Column: Zorbax Eclipse Plus C18, 21.2×100 mm, 5 µm particles; Solvent A=0.1% Formic Acid in 100% Water. Solvent B=Acetonitrile. Flow Rate=40 mL/min. Start % B=59 Final % B=79. Gradient Time=7 min, then a 2 min hold at 98% B. Wavelength=215 and 254 nm. ESI+Range: 150 to 1500 dalton. Sample was loaded at 30% B and afforded N—((S)-1-((3P)-3-(4-chloro-1-methyl-3-(methylsulfonamido)-1H-indazol-7-yl)-7-(2-cyclopropylethoxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (0.0067 g, 7.53 μmol, 20% yield). $^1$H NMR (500 MHz, METHANOL-$d_4$) δppm 8.25-8.32 (m, 1H) 7.06-7.14 (m, 1H) 6.97-7.05 (m, 1H) 6.82-6.88 (m, 1H) 6.35-6.64 (m, 4H) 4.64-4.67 (m, 2H) 4.35-4.48 (m, 4H) 3.39-3.45 (m, 3H) 3.26-3.30 (m, 1H) 3.02-3.06 (m, 3H) 2.89-2.96 (m, 1H) 2.19-2.27 (m, 2H) 1.58-1.64 (m, 1H) 1.50-1.54 (m, 1H) 1.10-1.23 (m, 2H) 0.69-0.86 (m, 2H) 0.31-0.39 (m, 1H) −0.03-0.03 (m, 1H). LC/MS retention time=1.50 min; m/z=890.3[M+H]$^+$ Column: Acquity BEH C18, 2.1×30 mm, 1.7 μm particles; Solvent A=0.1% Formic acid in 100% Water. Solvent B=0.1% Formic Acid in 100% Acetonitrile. Flow Rate=0.8 mL/min. Start % B=5. Final % B=95. Gradient Time=1.7 min, then a 0.2 min hold at 95% B. Wavelength=215 and 254 nm. ESI+Range: 150 to 1500 Dalton. System: Agilent 1290 Infinity II.

EXAMPLE 25

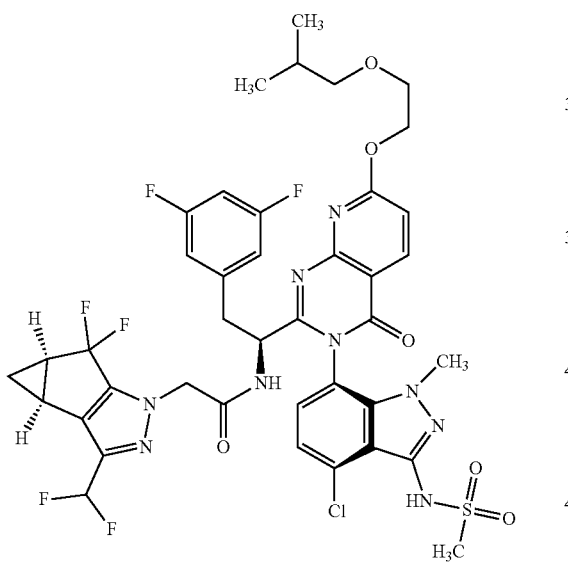

N—((S)-1-((3P)-3-(4-chloro-1-methyl-3-(methylsulfonamido)-1H-indazol-7-yl)-7-(2-isobutoxyethoxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide A solution of diisopropyl (E)-diazene-1,2-dicarboxylate ("DIAD", 0.034 ml, 0.174 mmol) in THF (0.1 mL) was added dropwise to a mixture of N—((S)-1-((3P)-3-(4-chloro-1-methyl-3-(N-(methylsulfonyl)acetamido)-1H-indazol-7-yl)-7-hydroxy-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (0.050 g, 0.058 mmol), 2-isobutoxyethan-1-ol (20 mg, 0.174 mmol) and triphenylphosphine (0.049 g, 0.185 mmol). The reaction mixture was stirred at room temperature for 18 h. To the solution was added ammonia in methanol (2M, 1 mL). The mixture was stirred at room temperature for 18 h. The mixture was concentrated under reduced pressure. The residue was dissolved in DMF, filtered through a syringe filter, and then subjected to prep-HPLC purification using the following conditions: Column=Waters XSelect CSH C18, 19×100 mm, 5 μm particles; Solvent A=0.1% Formic Acid in 100% Water. Solvent B=Acetonitrile; Flow Rate=40 mL/min.; Gradient profile [Time (min.)/% B]=0/25, 1/25, 1.01/58, 7/78, 7.01/98, 9/98. This purification afforded N—((S)-1-((3P)-3-(4-chloro-1-methyl-3-(methylsulfonamido)-1H-indazol-7-yl)-7-(2-isobutoxyethoxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. $^1$H NMR (500 MHz, METHANOL-$d_4$) δppm 8.45-8.52 (m, 1H) 7.26 (br d, J=1.49 Hz, 1H) 7.18 (d, J=7.45 Hz, 1H) 7.07 (d, J=8.64 Hz, 1H) 6.54-6.82 (m, 4H) 4.82 (br s, 1H) 4.67-4.73 (m, 2H) 4.50-4.61 (m, 2H) 3.85-3.91 (m, 2H) 3.58 (s, 3H) 3.45 (dd, J=13.86, 4.92 Hz, 1H) 3.33 (d, J=6.56 Hz, 2H) 3.21 (s, 3H) 3.11 (br d, J=9.54 Hz, 1H) 2.37-2.46 (m, 2H) 1.88 (dt, J=13.41, 6.71 Hz, 1H) 1.35 (qd, J=6.90, 1.34 Hz, 1H) 0.97-1.03 (m, 1H) 0.93 (d, J=6.85 Hz, 6H). LC/MS retention time=1.558 min; m/z=922.4[M+H]$^+$ using the following LC/MS method: Column=Acquity CSH C18, 2.1×30 mm, 1.7 μm particles; Solvent A=0.1% Formic acid in 100% Water; Solvent B=0.1% Formic Acid in 100% Acetonitrile; Flow Rate=0.8 mL/min; Start % B=5; Final % B=95; Gradient Time=1.7 min, then a 0.2 min hold at 95% B; Wavelength=215 and 254 nm; ESI+Range=150 to 1500 Dalton; System=Agilent 1290 Infinity II.

EXAMPLE 26

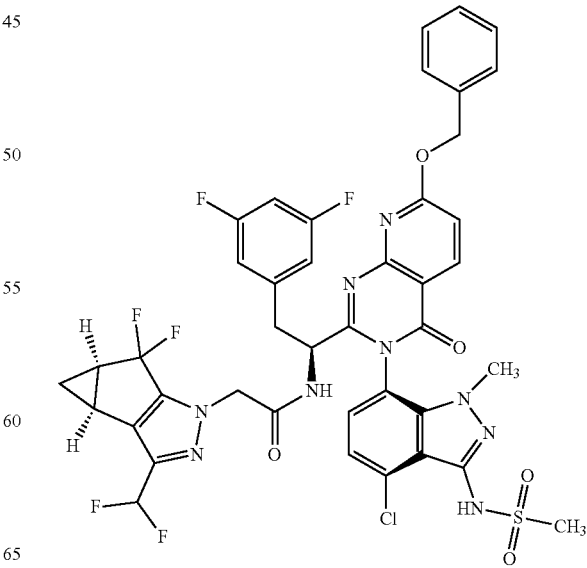

N—((S)-1-(7-(benzyloxy)-(3P)-3-(4-chloro-1-methyl-3-(methylsulfonamido)-1H-indazol-7-yl)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide A solution of diisopropyl (E)-diazene-1,2-dicarboxylate ("DIAD", 0.034 ml, 0.174 mmol) in THF (0.1 mL) was added dropwise to a mixture of N—((S)-1-((3P)-3-(4-chloro-1-methyl-3-(N-(methylsulfonyl)acetamido)-1H-indazol-7-yl)-7-hydroxy-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (0.050 g, 0.058 mmol), benzyl alcohol (19 mg, 0.174 mmol) and triphenylphosphine (0.049 g, 0.185 mmol). The reaction mixture was stirred at room temperature for 18 h. To the solution was added ammonia in methanol (2M, 1 mL). The mixture was stirred at room temperature for 18 h. The mixture was concentrated under reduced pressure. The residue was dissolved in DMF, filtered through a syringe filter, and then subjected to prep-HPLC purification using the following conditions: Column: Waters XSelect CSH C18, 19×100 mm, 5 μm particles; Solvent A=0.1% Formic Acid in 100% Water. Solvent B=Acetonitrile. Flow Rate=40 mL/min. Gradient profile [Time (min.)/% B]=0/30, 1/30, 1.01/57.5, 7/77.5, 7.01/98, 9/98. This purification afforded N—((S)-1-(7-(benzyloxy)-(3P)-3-(4-chloro-1-methyl-3-(methylsulfonamido)-1H-indazol-7-yl)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. $^1$H NMR (500 MHz, METHANOL-d$_4$) δppm 8.43-8.59 (m, 1H) 7.09-7.58 (m, 8H) 6.54-6.83 (m, 4H) 5.62-5.69 (m, 2H) 4.83-4.84 (m, 1H) 4.49-4.64 (m, 2H) 3.60-3.67 (m, 3H) 3.45-3.52 (m, 1H) 3.25-3.26 (m, 3H) 3.10-3.16 (m, 1H) 2.40-2.48 (m, 2H) 1.34-1.40 (m, 1H) 0.98-1.05 (m, 1H). LC/MS retention time=1.537 min; m/z=912.2[M+H]$^+$ using the following LC/MS method: Column=Acquity CSH C18, 2.1×30 mm, 1.7 μm particles; Solvent A=0.1% Formic acid in 100% Water; Solvent B=0.1% Formic Acid in 100% Acetonitrile; Flow Rate=0.8 mL/min; Start % B=5; Final % B=95; Gradient Time=1.7 min, then a 0.2 min hold at 95% B; Wavelength=215 and 254 nm; ESI+Range=150 to 1500 Dalton; System=Agilent 1290 Infinity II.

EXAMPLE 27

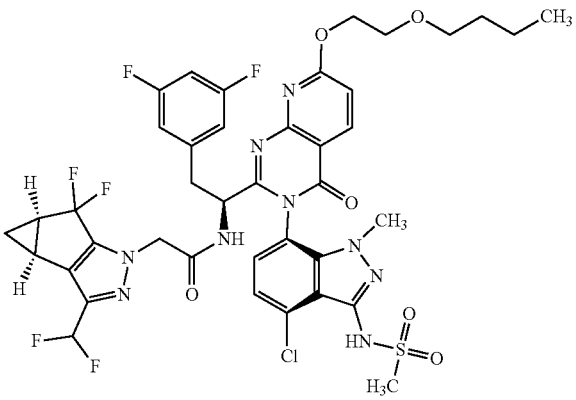

N—((S)-1-(7-(2-butoxyethoxy)-(3P)-3-(4-chloro-1-methyl-3-(methylsulfonamido)-1H-indazol-7-yl)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide A solution of diisopropyl (E)-diazene-1,2-dicarboxylate ("DIAD", 0.034 ml, 0.174 mmol) in THF (0.1 mL) was added dropwise to a mixture of N—((S)-1-((3P)-3-(4-chloro-1-methyl-3-(N-(methylsulfonyl)acetamido)-1H-indazol-7-yl)-7-hydroxy-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (0.050 g, 0.058 mmol), 2-butoxyethan-1-ol (21 mg, 0.174 mmol) and triphenylphosphine (0.049 g, 0.185 mmol). The reaction mixture was stirred at room temperature for 18 h. To the solution was added ammonia in methanol (2M, 1 mL). The mixture was stirred at room temperature for 18 h. The mixture was concentrated under reduced pressure. The residue was dissolved in DMF, filtered through a syringe filter, and then subjected to prep-HPLC purification using the following conditions: Column=Waters XSelect CSH C18, 19×100 mm, 5 μm particles; Solvent A=0.1% Formic Acid in 100% Water. Solvent B=Acetonitrile; Flow Rate=40 mL/min.; Gradient profile [Time (min.)/% B]=0/30, 1/30, 1.01/57.6, 7/77.6, 7.01/98, 9/98. This purification afforded N—((S)-1-(7-(2-butoxyethoxy)-(3P)-3-(4-chloro-1-methyl-3-(methylsulfonamido)-1H-indazol-7-yl)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. 1H NMR (500 MHz, METHANOL-d4) δppm 8.43-8.52 (m, 1H) 7.04-7.32 (m, 3H) 6.53-6.82 (m, 4H) 4.83-4.84 (m, 1H) 4.65-4.73 (m, 2H) 4.48-4.61 (m, 2H) 3.84-3.92 (m, 2H) 3.56-3.64 (m, 5H) 3.43-3.48 (m, 1H) 3.20 (s, 3H) 3.10 (dd, J=14.16, 9.39 Hz, 1H) 2.38-2.45 (m, 2H) 1.56-1.63 (m, 2H) 1.32-1.45 (m, 3H) 0.97-1.01 (m, 1H) 0.94 (t, J=7.45 Hz, 3H). LC/MS retention time=1.545 min; m/z=922.4 [M+H]$^+$ using the following LC/MS method: Column=Acquity CSH C18, 2.1×30 mm, 1.7 μm particles; Solvent A=0.1% Formic acid in 100% Water; Solvent B=0.1% Formic Acid in 100% Acetonitrile; Flow Rate=0.8 mL/min; Start % B=5; Final % B=95; Gradient Time=1.7 min, then a 0.2 min hold at 95% B; Wavelength=215 and 254 nm; ESI+Range=150 to 1500 Dalton; System=Agilent 1290 Infinity II.

EXAMPLE 28

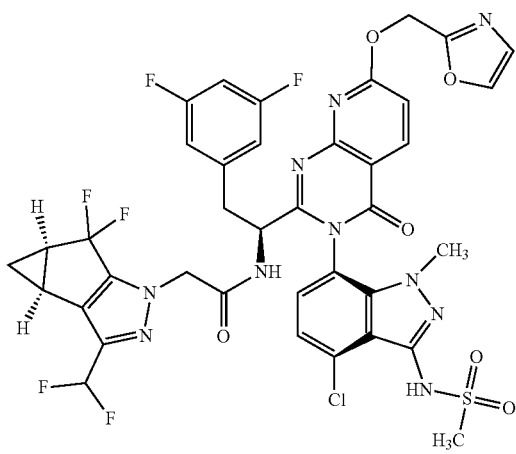

N—((S)-1-((3P)-3-(4-chloro-1-methyl-3-(methyl-sulfonamido)-1H-indazol-7-yl)-7-(oxazol-2-yl-methoxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide A solution of diisopropyl (E)-diazene-1,2-dicarboxylate ("DIAD", 0.034 ml, 0.174 mmol) in THF (0.1 mL) was added dropwise to a mixture of N—((S)-1-((3P)-3-(4-chloro-1-methyl-3-(N-(methylsulfonyl)acetamido)-1H-indazol-7-yl)-7-hydroxy-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (0.050 g, 0.058 mmol), oxazol-2-ylmethanol (17 mg, 0.174 mmol) and triphenylphosphine (0.049 g, 0.185 mmol). The reaction mixture was stirred at room temperature for 18 h. To the solution was added ammonia in methanol (2M, 1 mL). The mixture was stirred at room temperature for 18 h. The mixture was concentrated under reduced pressure. The residue was dissolved in DMF, filtered through a syringe filter, and then subjected to prep-HPLC purification using the following conditions: Column: Waters XSelect CSH C18, 19×100 mm, 5 μm particles; Solvent A=0.1% Formic Acid in 100% Water. Solvent B=Acetonitrile. Flow Rate=40 mL/min. Gradient profile [Time (min.)/% B]=0/20, 1/20, 1.01/47.4, 7/67.4, 7.01/98, 9/98. This purification afforded N—((S)-1-((3P)-3-(4-chloro-1-methyl-3-(methylsulfonamido)-1H-indazol-7-yl)-7-(oxazol-2-ylmethoxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. $^1$H NMR (500 MHz, METHANOL-d4) δppm 8.52-8.60 (m, 1H) 7.99-8.04 (m, 1H) 7.14-7.34 (m, 4H) 6.54-6.83 (m, 4H) 5.72-5.78 (m, 2H) 4.84-4.87 (m, 1H) 4.48-4.62 (m, 2H) 3.60-3.64 (m, 3H) 3.44-3.49 (m, 1H) 3.23-3.26 (m, 3H) 3.08-3.15 (m, 1H) 2.40-2.47 (m, 2H) 1.34-1.40 (m, 1H) 0.99-1.04 (m, 1H). LC/MS retention time=1.351 min; m/z=903.2[M+H]$^+$ using the following LC/MS method: Column=Acquity CSH C18, 2.1×30 mm, 1.7 μm particles; Solvent A=0.1% Formic acid in 100% Water; Solvent B=0.1% Formic Acid in 100% Acetonitrile; Flow Rate=0.8 mL/min; Start % B=5; Final % B=95; Gradient Time=1.7 min, then a 0.2 min hold at 95% B; Wavelength=215 and 254 nm; ESI+Range=150 to 1500 Dalton; System=Agilent 1290 Infinity II.

EXAMPLE 29

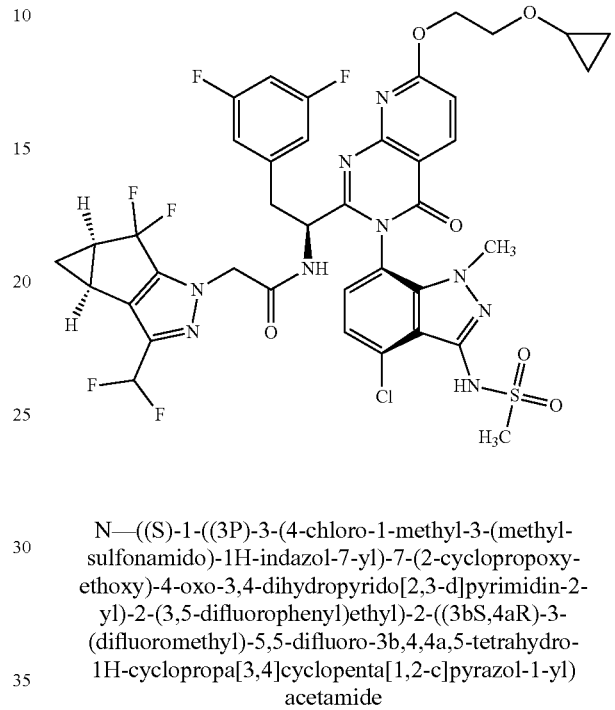

N—((S)-1-((3P)-3-(4-chloro-1-methyl-3-(methyl-sulfonamido)-1H-indazol-7-yl)-7-(2-cyclopropoxy-ethoxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide A solution of diisopropyl (E)-diazene-1,2-dicarboxylate ("DIAD", 0.034 ml, 0.174 mmol) in THF (0.1 mL) was added dropwise to a mixture of N—((S)-1-((3P)-3-(4-chloro-1-methyl-3-(N-(methylsulfonyl)acetamido)-1H-indazol-7-yl)-7-hydroxy-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (0.050 g, 0.058 mmol), 2-cyclopropoxyethan-1-ol (18 mg, 0.174 mmol) and triphenylphosphine (0.049 g, 0.185 mmol). The reaction mixture was stirred at room temperature for 18 h. To the solution was added ammonia in methanol (2M, 1 mL). The mixture was stirred at room temperature for 18 h. The mixture was concentrated under reduced pressure. The residue was dissolved in DMF, filtered through a syringe filter, and then subjected to prep-HPLC purification using the following conditions: Column: Waters XSelect CSH C18, 19×100 mm, 5 μm particles; Solvent A=0.1% Formic Acid in 100% Water. Solvent B=Acetonitrile. Flow Rate=40 mL/min. Gradient profile [Time (min.)/% B]=0/30, 1/30, 1.01/48.9, 7/68.9, 7.01/98, 9/98. This purification afforded N—((S)-1-((3P)-3-(4-chloro-1-methyl-3-(methylsulfona-mido)-1H-indazol-7-yl)-7-(2-cyclopropoxyethoxy)-4-oxo-3,4-dihydropyrido[2,3-d]pyrimidin-2-yl)-2-(3,5-difluoro-phenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. $^1$H NMR (500 MHz, METHANOL-d4) δppm 8.52-8.60 (m, 1H) 7.99-8.04 (m, 1H) 7.14-7.34 (m, 4H) 6.54-6.83 (m, 4H) 5.72-5.78 (m, 2H) 4.84-4.87 (m, 1H) 4.48-4.62 (m, 2H) 3.60-3.64 (m, 3H)

3.44-3.49 (m, 1H) 3.23-3.26 (m, 3H) 3.08-3.15 (m, 1H) 2.40-2.47 (m, 2H) 1.34-1.40 (m, 1H) 0.99-1.04 (m, 1H). LC/MS retention time=1.444 min; m/z=906.3[M+H]+ using the following LC/MS method: Column=Acquity CSH C18, 2.1×30 mm, 1.7 μm particles; Solvent A=0.1% Formic acid in 100% Water; Solvent B=0.1% Formic Acid in 100% Acetonitrile; Flow Rate=0.8 mL/min; Start % B=5; Final % B=95; Gradient Time=1.7 min, then a 0.2 min hold at 95% B; Wavelength=215 and 254 nm; ESI+Range=150 to 1500 Dalton; System=Agilent 1290 Infinity II.

EXAMPLE 30

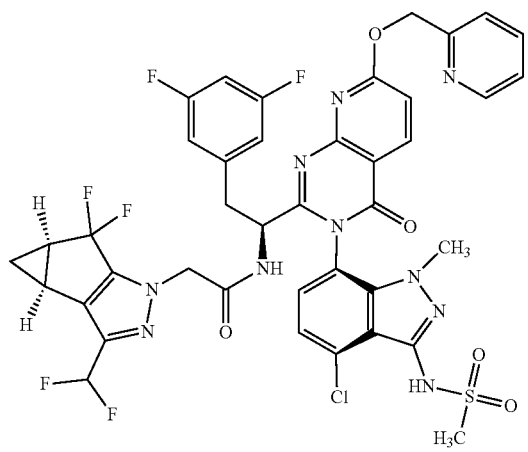

N—((S)-1-((3P)-3-(4-chloro-1-methyl-3-(methylsulfonamido)-1H-indazol-7-yl)-4-oxo-7-(pyridin-2-ylmethoxy)-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide A solution of diisopropyl (E)-diazene-1,2-dicarboxylate ("DIAD", 0.034 ml, 0.174 mmol) in THF (0.1 mL) was added dropwise to a mixture of N—((S)-1-((3P)-3-(4-chloro-1-methyl-3-(N-(methylsulfonyl)acetamido)-1H-indazol-7-yl)-7-hydroxy-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (0.050 g, 0.058 mmol), pyridin-2-ylmethanol (19 mg, 0.174 mmol) and triphenylphosphine (0.049 g, 0.185 mmol). The reaction mixture was stirred at room temperature for 18 h. To the solution was added ammonia in methanol (2M, 1 mL). The mixture was stirred at room temperature for 18 h. The mixture was concentrated under reduced pressure. The residue was dissolved in DMF, filtered through a syringe filter, and then subjected to prep-HPLC purification using the following conditions: Column: Waters XSelect CSH C18, 19×100 mm, 5 μm particles; Solvent A=0.1% Formic Acid in 100% Water. Solvent B=Acetonitrile. Flow Rate=40 mL/min. Gradient profile [Time (min.)/% B]=0/25, 1/25, 1.01/44.5, 7/64.5, 7.01/98, 9/98. This purification afforded N—((S)-1-((3P)-3-(4-chloro-1-methyl-3-(methylsulfonamido)-1H-indazol-7-yl)-4-oxo-7-(pyridin-2-ylmethoxy)-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. 1H NMR (500 MHz, METHANOL-d4) δppm 8.51-8.62 (m, 2H) 7.93 (d, J=1.79 Hz, 1H) 7.66 (d, J=7.75 Hz, 1H) 7.17-7.48 (m, 4H) 6.52-6.86 (m, 4H) 5.69-5.80 (m, 2H) 4.83-4.86 (m, 1H) 4.47-4.62 (m, 2H) 3.62 (s, 3H) 3.42-3.50 (m, 1H) 3.24 (s, 3H) 3.06-3.15 (m, 1H) 2.38-2.47 (m, 2H) 1.34-1.40 (m, 1H) 0.98-1.04 (m, 1H). LC/MS retention time=1.332 min; m/z=913.2[M+H]+; LC/MS method: Column=Acquity CSH C18, 2.1×30 mm, 1.7 μm particles; Solvent A=0.1% Formic acid in 100% Water; Solvent B=0.1% Formic Acid in 100% Acetonitrile; Flow Rate=0.8 mL/min.; Start % B=5; Final % B=95; Gradient Time=1.7 min, then a 0.2 min hold at 95% B; Wavelength=215 and 254 nm; ESI+Range: 150 to 1500 Dalton; System=Agilent 1290 Infinity II.

EXAMPLE 31

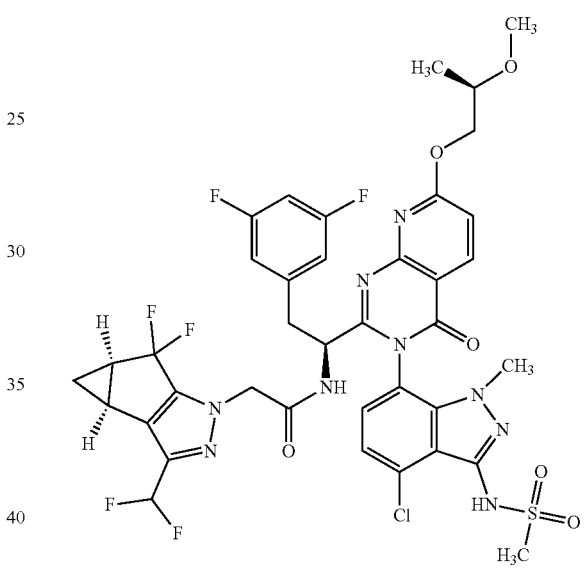

N—((S)-1-((3P)-3-(4-chloro-1-methyl-3-(methylsulfonamido)-1H-indazol-7-yl)-7-((R)-2-methoxypropoxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide A solution of diisopropyl (E)-diazene-1,2-dicarboxylate ("DIAD", 0.034 ml, 0.174 mmol) in THF (0.1 mL) was added dropwise to a mixture of N—((S)-1-((3P)-3-(4-chloro-1-methyl-3-(N-(methylsulfonyl)acetamido)-1H-indazol-7-yl)-7-hydroxy-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (0.050 g, 0.058 mmol), (R)-2-methoxypropan-1-ol (16 mg, 0.174 mmol) and triphenylphosphine (0.049 g, 0.185 mmol). The reaction mixture was stirred at room temperature for 18 h. To the solution was added ammonia in methanol (2M, 1 mL). The mixture was stirred at room temperature for 18 h. The mixture was concentrated under reduced pressure. The residue was dissolved in DMF, filtered through a syringe filter, and then subjected to prep-HPLC purification using the following conditions: Column: Waters XSelect CSH C18, 19×100 mm, 5 μm particles; Solvent A=0.1% Formic Acid in 100% Water. Solvent B=Acetonitrile. Flow Rate=40 mL/min. Gradient profile [Time (min.)/% B]=0/30, 1/30, 1.01/47.5, 7/67.5, 7.01/98, 9/98. This purification afforded N—((S)-1-((3P)-3-(4-chloro-1-methyl-3-(methylsulfonamido)-1H-indazol-7-yl)-7-((R)-2-methoxypropoxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. $^1$H NMR (500 MHz, METHANOL-d$_4$) δppm 8.46-8.53 (m, 1H) 7.28-7.33 (m, 1H) 7.20-7.24 (m, 1H) 7.07-7.13 (m, 1H) 6.56-6.83 (m, 4H) 4.84-4.86 (m, 1H) 4.48-4.63 (m, 4H) 3.84-3.92 (m, 1H) 3.60-3.64 (m, 3H) 3.44-3.51 (m, 4H) 3.23-3.26 (m, 3H) 3.09-3.16 (m, 1H) 2.40-2.48 (m, 2H) 1.35-1.41 (m, 1H) 1.32-1.34 (m, 3H) 1.00-1.04 (m, 1H). LC/MS retention time=1.38 min; m/z=894.3[M+H]$^+$; LC/MS method: Column=Acquity CSH C18, 2.1×30 mm, 1.7 μm particles; Solvent A=0.1% Formic acid in 100% Water; Solvent B=0.1% Formic Acid in 100% Acetonitrile; Flow Rate=0.8 mL/min.; Start % B=5; Final % B=95; Gradient Time=1.7 min, then a 0.2 min hold at 95% B; Wavelength=215 and 254 nm; ESI+Range: 150 to 1500 Dalton; System=Agilent 1290 Infinity II.

IUPAC Chemical Names: The IUPAC chemical names for each example are listed below. At this time these names are not recognized by common software such tools such as ChemDraw or JChem. Therefore, the chemical names used throughout the Examples section above were generated with ChemDraw and then appended with the correct P/M designation. The chemical names above can be converted to chemical structures using ChemDraw after the P/M nomenclature—e.g., "(3P)-"—is removed.

| Example | IUPAC Name |
| --- | --- |
| Example 1 | N-[(1S)-1-[(3P)-3-(4-chloro-3-methanesulfonamido-1-methyl-1H-indazol-7-yl)-7-hydroxy-4-oxo-3H,4H-pyrido[2,3-d]pyrimidin-2-yl]-2-(3,5-difluorophenyl)ethyl]-2-[(2S, 4R)-9-(difluoromethyl)-5,5-difluoro-7,8-diazatricyclo[4.3.0.0$^{2,4}$]nona-1(6),8-dien-7-yl]acetamide |
| Example 2 | N-[(1S)-1-[(3P)-3-(4-chloro-3-methanesulfonamido-1-methyl-1H-indazol-7-yl)-7-(cyclopentylmethoxy)-4-oxo-3H,4H-pyrido[2,3-d]pyrimidin-2-yl]-2-(3,5-difluorophenyl)ethyl]-2-[(2S, 4R)-9-(difluoromethyl)-5,5-difluoro-7,8-diazatricyclo[4.3.0.0$^{2,4}$]nona-1(6),8-dien-7-yl]acetamide |
| Example 3 | N-[(1S)-1-[(3P)-3-(4-chloro-3-methanesulfonamido-1-methyl-1H-indazol-7-yl)-7-(3,3-dimethylbutoxy)-4-oxo-3H,4H-pyrido[2,3-d]pyrimidin-2-yl]-2-(3,5-difluorophenyl)ethyl]-2-[(2S, 4R)-9-(difluoromethyl)-5,5-difluoro-7,8-diazatricyclo[4.3.0.0$^{2,4}$]nona-1(6),8-dien-7-yl]acetamide |
| Example 4 | N-[(1S)-1-[(3P)-3-(4-chloro-3-methanesulfonamido-1-methyl-1H-indazol-7-yl)-4-oxo-7-[2-(propan-2-yloxy)ethoxy]-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 7 | N-[(1S)-1-[(3P,3P)-3-(4-chloro-3-methanesulfonamido-1-methyl-1H-indazol-7-yl)-7-[2-(1,1-dioxo-1λ$^6$-thiomorpholin-4-yl)ethoxy]-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 9 | N-[(1S)-1-[(3P,3P)-3-(4-chloro-3-methanesulfonamido-1-methyl-1H-indazol-7-yl)-4-oxo-7-[(pyrimidin-2-yl)methoxyl]-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 11 | N-[(1S)-1-[(3P,3P)-3-(4-chloro-3-methanesulfonamido-1-methyl-1H-indazol-7-yl)-4-oxo-7-[2-(piperidin-1-yl)ethoxyl]-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 13 | N-[(1S)-1-[(3P)-3-(4-chloro-3-methanesulfonamido-1-methyl-1H-indazol-7-yl)-7-[(3,3-dimethylpentyl)oxy]-4-oxo-3H,4H-pyrido[2,3-d]pyrimidin-2-yl]-2-(3,5-difluorophenyl)pethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 14 | N-[(1S)-1-[(3P)-3-[4-chloro-1-(2,2-difluoroethyl)-3-methanesulfonamido-1H-indazol-7-yl]-7-(3,3-dimethylbutoxy)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 16 | N-[(1S)-1-[(3P)-3-(4-chloro-3-methanesulfonamido-1-methyl-1H-indazol-7-yl)-7-[(1R)-1-cyclopentylethoxy]-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 18 | N-[(1S)-1-[(3P,3P)-3-(4-chloro-3-methanesulfonamido-1-methyl-1H-indazol-7-yl)-4-oxo-7-[2-(1,3-thiazol-2-yl)ethoxyl-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 19 | N-[(1S)-1-[(3P)-3-(4-chloro-3-methanesulfonamido-1-methyl-1H-indazol-7-yl)-7-[(4,4-dimethylpentyl)oxy]-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 20 | N-[(1S)-1-[(3P)-3-(4-chloro-3-methanesulfonamido-1-methyl-1H-indazol-7-yl)-7-(3-methanesulfonylpropoxy)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |

-continued

| Example | IUPAC Name |
| --- | --- |
| Example 22 | N-[(1S)-1-[(3P,3P)-3-[4-chloro-1-(2,2-difluoroethyl)-3-methanesulfonamido-1H-indazol-7-yl]-7-(2-cyclopropylethoxy)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 23 | N-[(1S)-1-[(3P)-3-(4-chloro-3-methanesulfonamido-1-methyl-1H-indazol-7-yl)-7-[(1S)-1-cyclopentylethoxyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 24 | N-[(1S)-1-[(3P,3P)-3-(4-chloro-3-methanesulfonamido-1-methyl-1H-indazol-7-yl)-7-(2-cyclopropylethoxy)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 25 | N-[(1S)-1-[(3P)-3-(4-chloro-3-methanesulfonamido-1-methyl-1H-indazol-7-yl)-7-[2-(2-methylpropoxy)ethoxy]-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 26 | N-[(1S)-1-[(3P)-7-(benzyloxy)-3-(4-chloro-3-methanesulfonamido-1-methyl-1H-indazol-7-yl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 27 | N-[(1S)-1-[(3P)-7-(2-butoxyethoxy)-3-(4-chloro-3-methanesulfonamido-1-methyl-1H-indazol-7-yl)-4-oxo-3H,4H-pyrido[2,3-dlpyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 28 | N-[(1S)-1-[(3P)-3-(4-chloro-3-methanesulfonamido-1-methyl-1H-indazol-7-yl)-7-[(1,3-oxazol-2-yl)methoxy]-4-oxo-3H,4H-pyrido[2,3-d]pyrimidin-2-yl]-2-(3,5-difluorophenylethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 29 | N-[(1S)-1-[(3P,3P)-3-(4-chloro-3-methanesulfonamido-1-methyl-1H-indazol-7-yl)-7-(2-cyclopropoxyethoxy)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 30 | N-[(1S)-1-[(3P,3P)-3-(4-chloro-3-methanesulfonamido-1-methyl-1H-indazol-7-yl)-4-oxo-7-[(pyridin-2-yl)methoxyl-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 31 | N-[(1S)-1-[3-(4-chloro-3-methanesulfonamido-1-methyl-1H-indazol-7-yl)-7-[(2R)-2-methoxypropoxy]-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |

Biological Methods

HIV cell culture assay-MT-2 cells, 293T cells and the proviral DNA clone of $NL_{4-3}$ virus were obtained from the NIH AIDS Research and Reference Reagent Program. MT-2 cells were propagated in RPMI 1640 media supplemented with 10% heat inactivated fetal bovine serum (FBS), 100 µg/ml penicillin G and up to 100 units/mL streptomycin. The 293T cells were propagated in DMEM media supplemented with 10% heat inactivated FBS, 100 µg/mL penicillin G and 100 µg/mL streptomycin. A recombinant $NL_{4-3}$ proviral clone, in which a section of the nef gene was replaced with the Renilla luciferase gene, was used to make the reference virus used in these studies. The recombinant virus was prepared through transfection of the recombinant $NL_{4-3}$ proviral clone into 293T cells using Transit-293 Transfection Reagent from Minis Bio LLC (Madison, WI). Supernatant was harvested after 2-3 days and the amount of virus present was titered in MT-2 cells using luciferase enzyme activity as a marker by measuring luciferase enzyme activity. Luciferase was quantitated using the EnduRen Live Cell Substrate from Promega (Madison, WI). Antiviral activities of compounds toward the recombinant virus were quantified by measuring luciferase activity in MT-2 cells infected for 4-5 days with the recombinant virus in the presence of serial dilutions of the compound.

The 50% effective concentration ($EC_{50}$) was calculated by using the exponential form of the median effect equation where (Fa)=1/[1+($ED_{50}$/drug conc.)m] (Johnson V A, Byington R T. Infectivity Assay. In Techniques in HIV Research. ed. Aldovini A, Walker B D. 71-76. New York: Stockton Press. 1990).

Compound cytotoxicity and the corresponding $CC_{50}$ values were determined using the same protocol as described in the antiviral assay except that uninfected cells were used. Cytotoxicity was assessed on day 4 in uninfected MT2 cells by using an XTT (2,3-bis[2-Methoxy-4-nitro-5-sulfophenyl]-2H-tetrazolium-5-carboxyanilide inner salt)-based colorimetric assay (Sigma-Aldrich, St Louis, Mo.).

| Example | $EC_{50}$ nM | $CC_{50}$ µM |
| --- | --- | --- |
| Example 1 | 2.7 | >1 |
| Example 2 | 0.06 | >1 |
| Example 3 | 0.06 | >1 |
| Example 4 | <0.05 | >1 |
| Example 7 | 0.26 | >1 |
| Example 9 | 0.03 | >1 |
| Example 11 | 0.49 | >1 |
| Example 13 | 0.17 | |
| Example 14 | 0.12 | >0.5 |
| Example 16 | 0.22 | >0.5 |
| Example 18 | 0.038 | >0.5 |
| Example 19 | 0.11 | |
| Example 20 | 0.18 | >0.5 |
| Example 22 | 0.29 | >0.5 |
| Example 23 | 0.17 | >0.5 |
| Example 24 | 0.051 | >0.5 |
| Example 25 | 0.054 | >0.1 |
| Example 26 | 0.1 | >0.1 |

-continued

| Example | EC$_{50}$ nM | CC$_{50}$ μM |
|---|---|---|
| Example 27 | 0.041 | >0.1 |
| Example 29 | 0.034 | >0.1 |
| Example 30 | 0.043 | >0.1 |
| Example 31 | 0.019 | >0.1 |

The disclosure is not limited to the foregoing illustrative examples and the examples should be considered in all respects as illustrative and not restrictive, reference being made to the appended claims, rather than to the foregoing examples, and all changes which come within the meaning and range of equivalency of the claims are therefore intended to be embraced.

What is claimed is:
1. A compound of Formula I, or a pharmaceutically acceptable salt thereof:

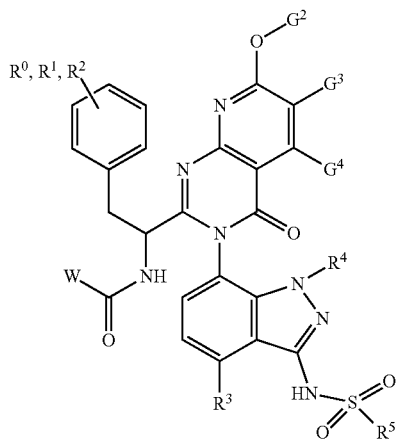

wherein:
R$^0$, R$^1$, and R$^2$ are each independently hydrogen, Cl, F, —OMe, —CN, —C$_1$-C$_3$alkyl, or —C$_3$-C$_5$ cycloalkyl, wherein C$_1$-C$_3$ alkyl may be optionally substituted with from 1-3 fluorines;
G$^2$ is hydrogen, 6 membered aryl, 5-6 membered heteroaryl, —C$_6$-C$_8$ alkyl, —C$_3$-C$_7$ cycloalkyl, or —C$_1$-C$_3$ alkyl wherein —C$_1$-C$_3$ alkyl is substituted with G$^5$;
G$^3$ is hydrogen, methyl, fluoro, chloro, phenyl, OC$_1$-C$_3$ alkyl, or OPh;
G$^4$ is hydrogen, methyl, fluoro, chloro, phenyl, OC$_1$-C$_3$ alkyl, or OPh;
G$^5$ is —OG$^6$, —C$_3$-C$_7$ cycloalkyl, 6 membered aryl, 5 membered heteroaryl, 4-7 membered heterocycle, —C(O)N(G$^7$)(G$^8$), C(O)OH, —SO$_2$(G$^7$), —N(G$^7$)(G$^8$), —SO$_2$-morpholine, C(O)-morpholine, or one of the following:

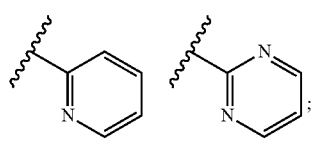

G$^6$ is —C$_1$-C$_6$ alkyl, —C$_3$-C$_7$ cycloalkyl, 6 membered aryl, 5 membered heteroaryl, 4-7 membered heterocycle;
G$^7$ is —C$_1$-C$_6$ alkyl or C$_3$-C$_6$ cycloalkyl;
G$^8$ is —C$_1$-C$_6$ alkyl or C$_3$-C$_6$ cycloalkyl;
R$^3$ is hydrogen, Cl, or F;
R$^4$ is hydrogen, C$_1$-C$_3$ alkyl, or cyclopropyl wherein cyclopropyl or C$_1$-C$_3$ cycloalkyl is optionally substituted with 1-3 fluorines;
R$^5$ is C$_1$-C$_6$ alkyl, C$_3$-C$_6$ cycloalkyl, or N(G$^7$)(G$^8$);
W is selected from:

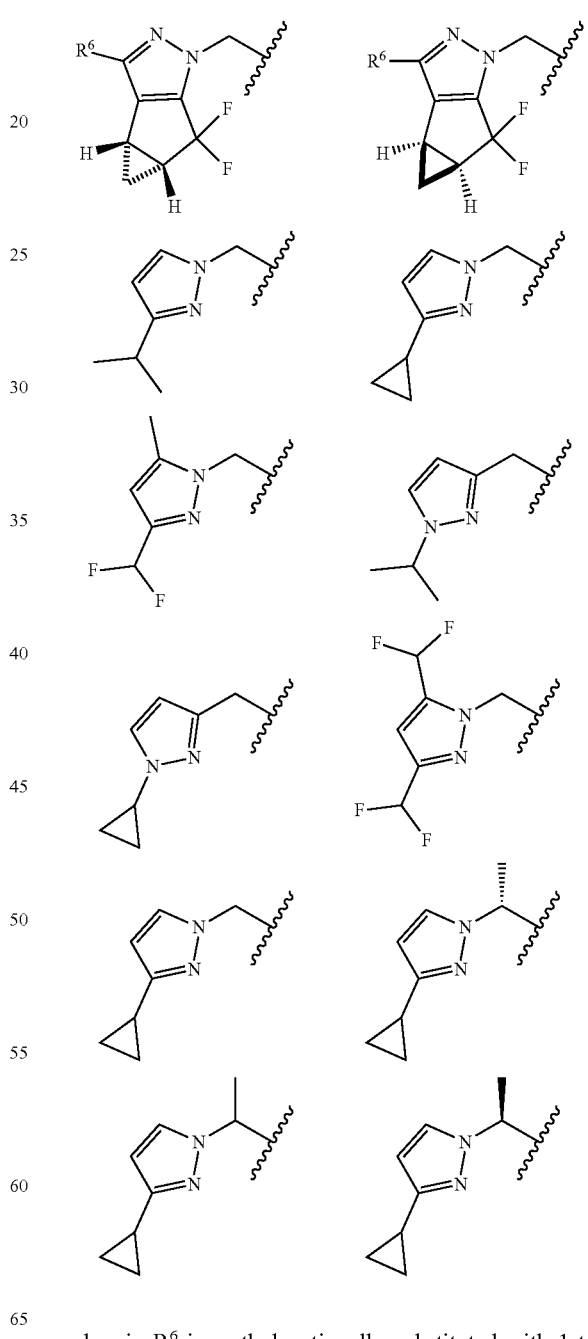

wherein R$^6$ is methyl optionally substituted with 1 to 3 fluorines.

2. A compound or salt according to claim 1 wherein the position of $R^0$, $R^1$, and $R^2$ are

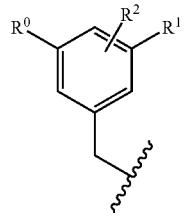

and $R^0$, $R^1$, and $R^2$ are each independently selected from hydrogen, Cl, F, —OCH$_3$, —CN, or —CH$_3$ with the proviso that substituents Cl, —OMe, and —CH$_3$ may not be used more than twice and substituent —CN may not be used more than once.

3. A compound or salt according to claim 1 wherein $G^3$ and $G^4$ are independently selected from hydrogen, methyl, fluoro, chloro, or OC$_1$-C$_2$ alkyl with the proviso that at least one of $G^3$ and $G^4$ must be hydrogen.

4. A compound or salt according to claim 1 wherein $R^3$ is hydrogen, Cl, or F;
$R^4$ is hydrogen, C$_1$-C$_3$ alkyl, or cyclopropyl wherein C$_1$-C$_3$ alkyl is optionally substituted with 1-3 fluorines and cyclopropyl is optionally substituted with 1-2 fluorines; $R^5$ is C$_1$-C$_3$ alkyl or C$_3$-C$_4$ cycloalkyl.

5. A compound or salt according to claim 1 wherein W is

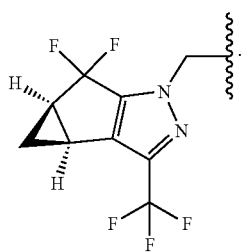 [SMILES: *Cn1nc(C(F)(F)F)c2c1C(F)(F)[C@@H]1C[C@H]21]

6. A compound or salt according to claim 1 wherein W is

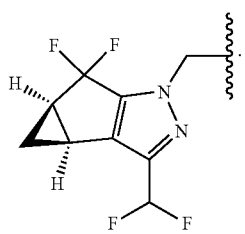 [SMILES: *Cn1nc(C(F)F)c2c1C(F)(F)[C@@H]1C[C@H]21]

7. A compound or salt according to claim 1 wherein W is one of the following:

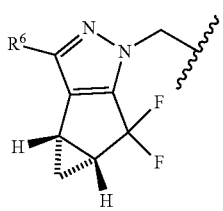 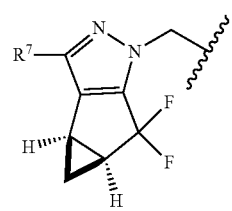

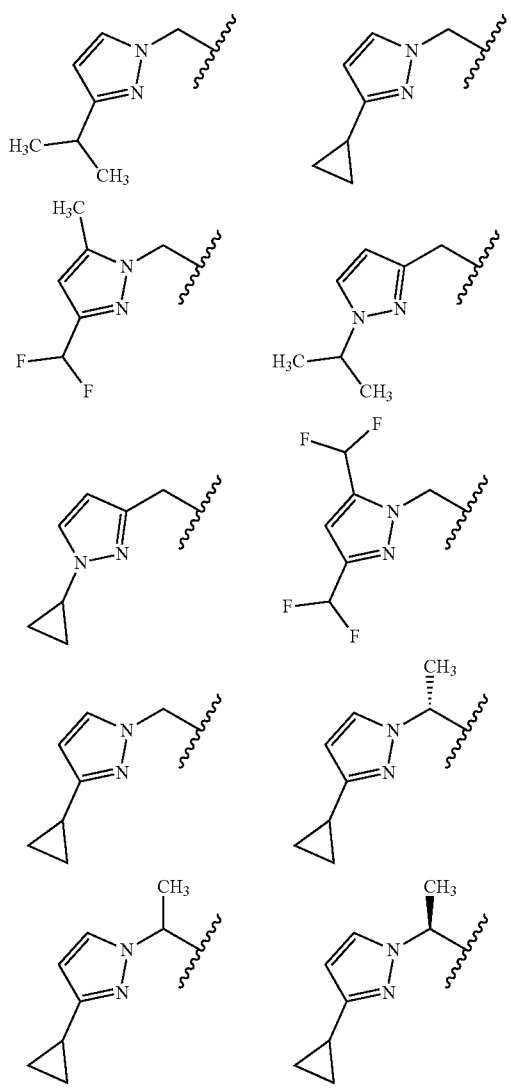

wherein $R^6$ is methyl optionally substituted with one fluorine and $R^7$ is methyl optionally substituted with 1 to 3 fluorines.

8. A compound or salt according to claim 1 wherein $G^2$ is hydrogen, —C$_6$-C$_8$ alkyl, or —C$_1$-C$_3$ alkyl wherein —C$_1$-C$_3$ alkyl is substituted with $G^5$; $G^5$ is —OG$^6$, —C$_3$-C$_6$ cycloalkyl, 6 membered aryl, 5 membered heteroaryl, 4-7 membered heterocycle, —C(O)N(G$^7$)(G$^8$), —SO$_2$(G$^7$), —N(G$^7$)(G$^8$), —SO$_2$-morpholine, C(O)-morpholine, or one of the following:

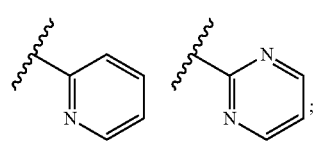

$G^7$ is —C$_1$-C$_3$ alkyl or C$_3$-C$_6$ cycloalkyl; and
$G^8$ is —C$_1$-C$_3$ alkyl or C$_3$-C$_6$ cycloalkyl.

9. A compound or salt according to claim 1 wherein $G^2$ is one of the following:

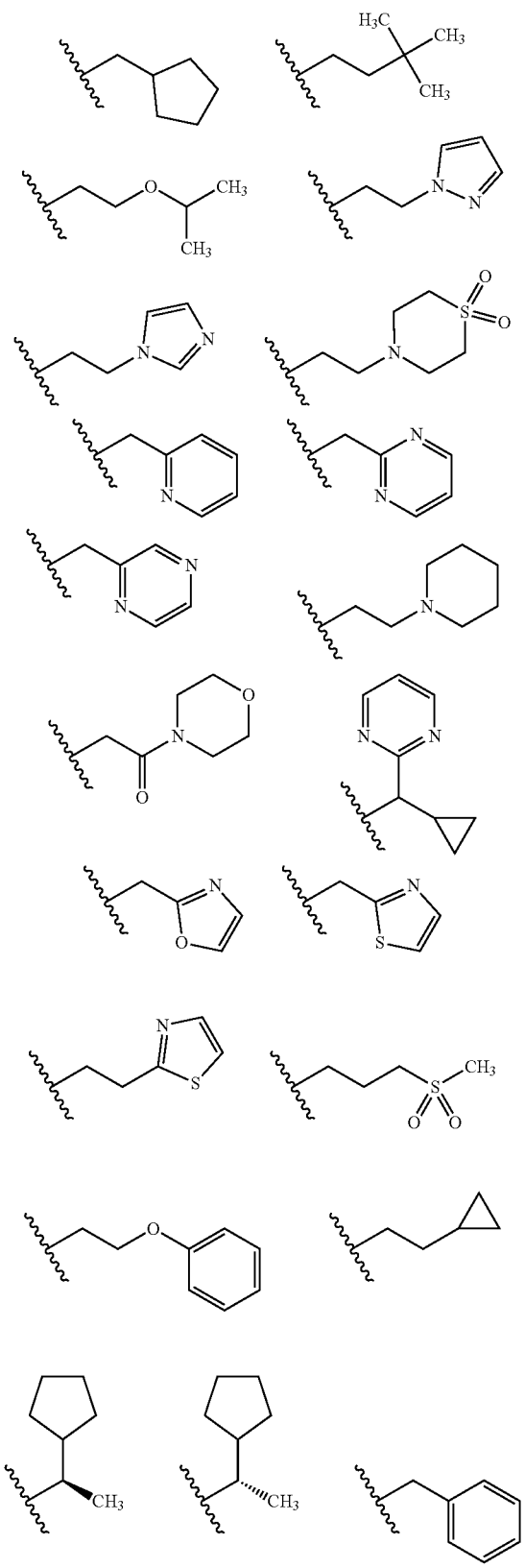

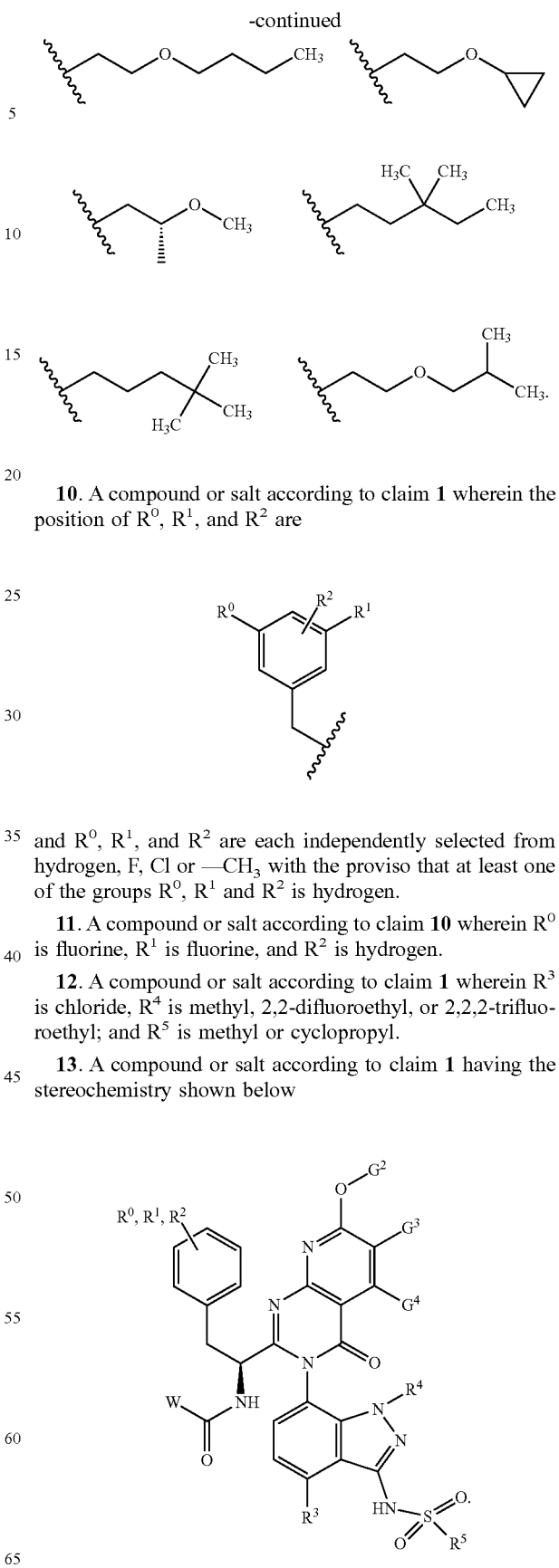

10. A compound or salt according to claim 1 wherein the position of $R^0$, $R^1$, and $R^2$ are and $R^0$, $R^1$, and $R^2$ are each independently selected from hydrogen, F, Cl or —$CH_3$ with the proviso that at least one of the groups $R^0$, $R^1$ and $R^2$ is hydrogen.

11. A compound or salt according to claim 10 wherein $R^0$ is fluorine, $R^1$ is fluorine, and $R^2$ is hydrogen.

12. A compound or salt according to claim 1 wherein $R^3$ is chloride, $R^4$ is methyl, 2,2-difluoroethyl, or 2,2,2-trifluoroethyl; and $R^5$ is methyl or cyclopropyl.

13. A compound or salt according to claim 1 having the stereochemistry shown below

14. A compound or salt according to claim 13 having the stereochemistry shown below
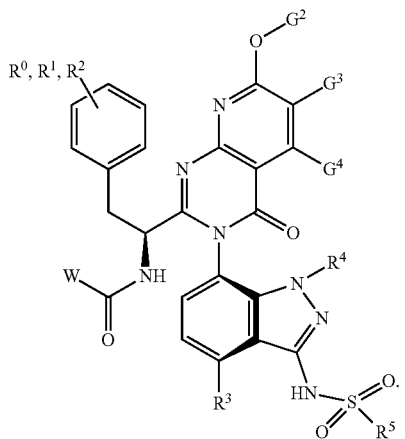
15. A compound or salt according to claim 1, selected from the group consisting of:
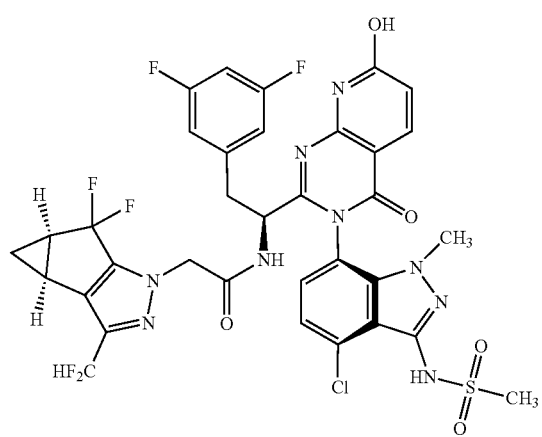
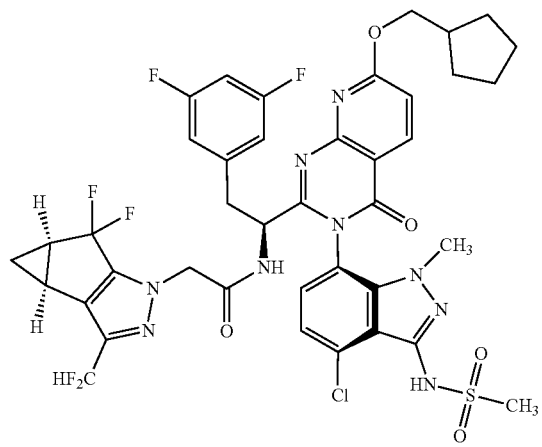
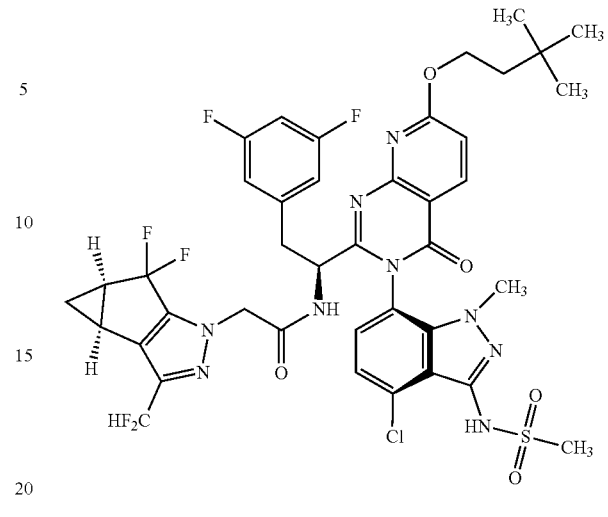
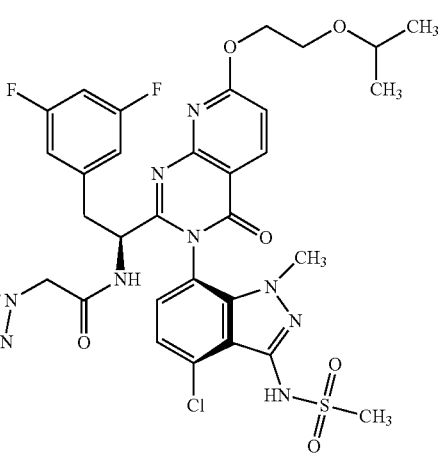

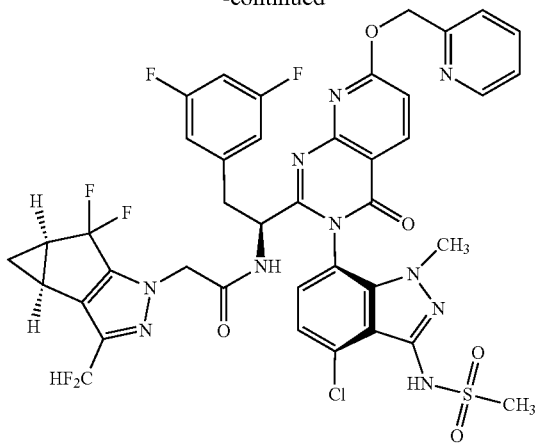
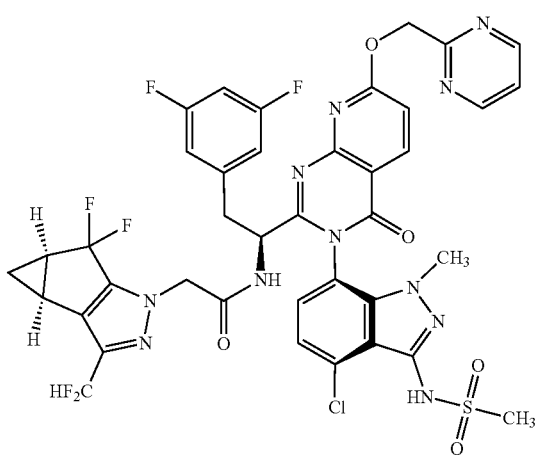
and pharmaceutically acceptable salts thereof.
16. A compound or salt according to claim 1, selected from the group consisting of:
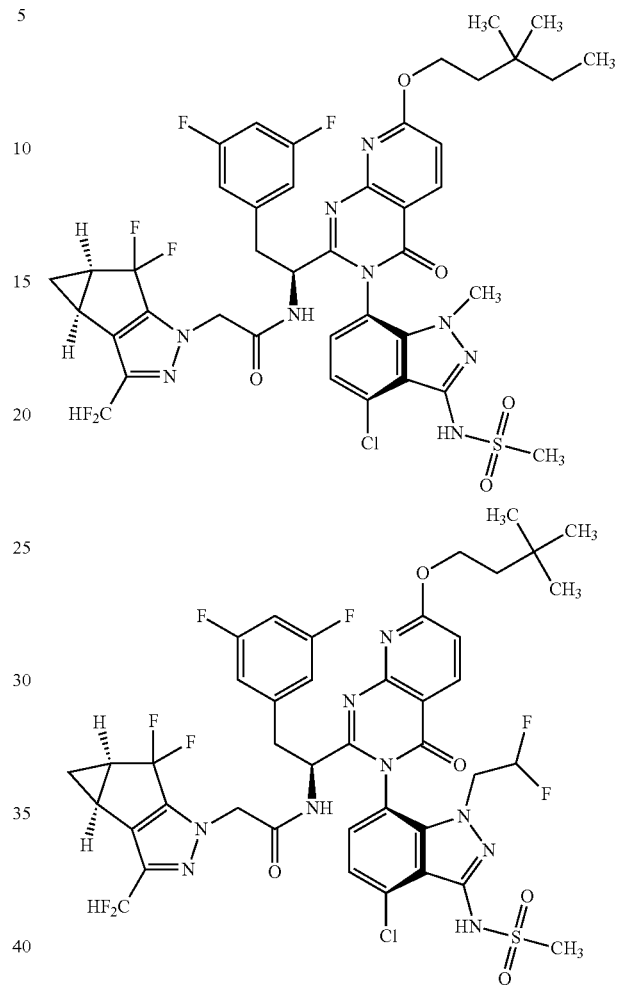

91
-continued
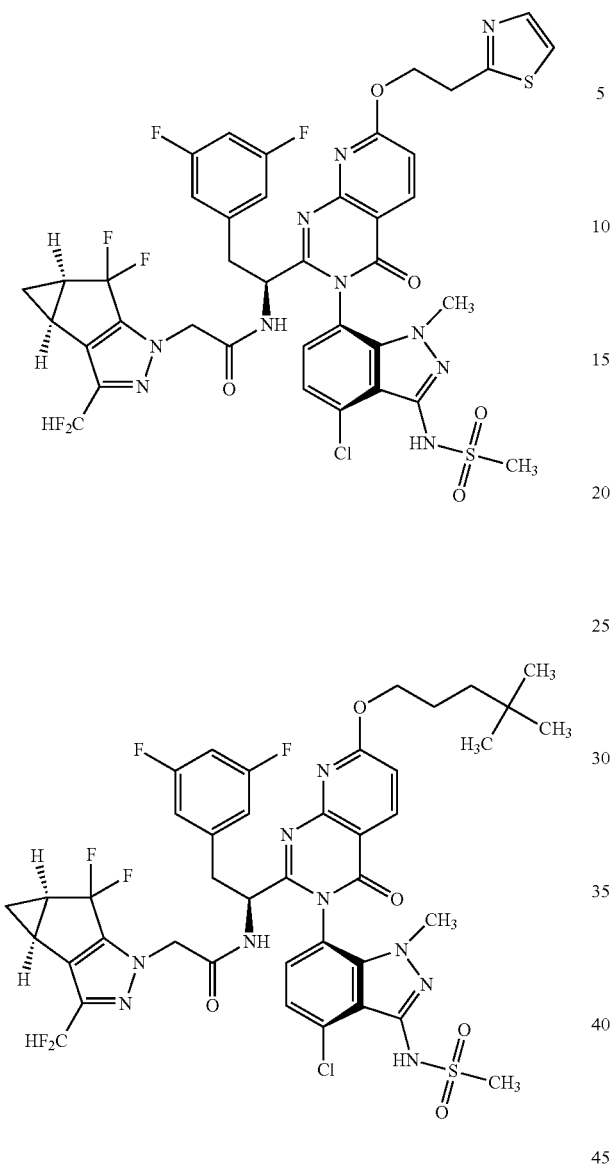
92
-continued
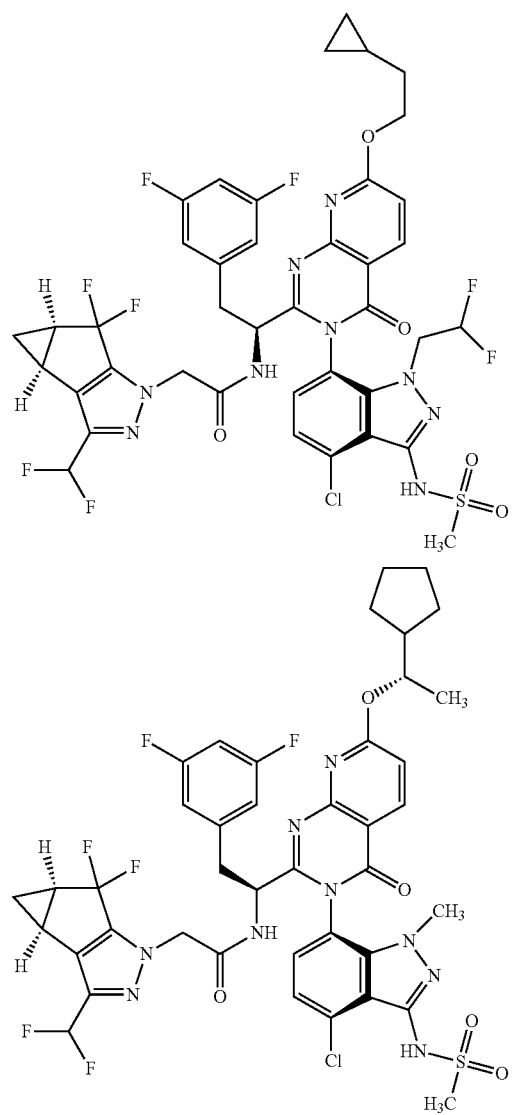
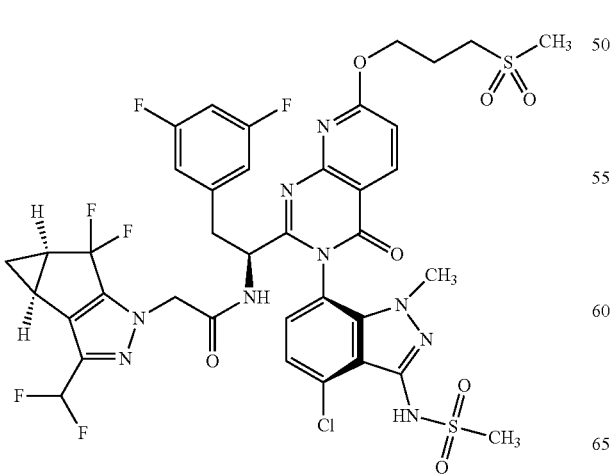
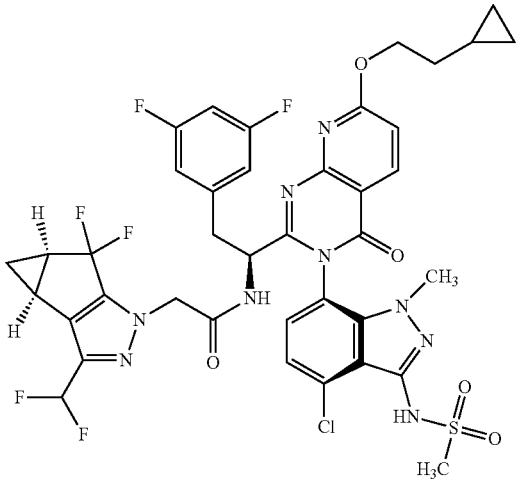

93
-continued

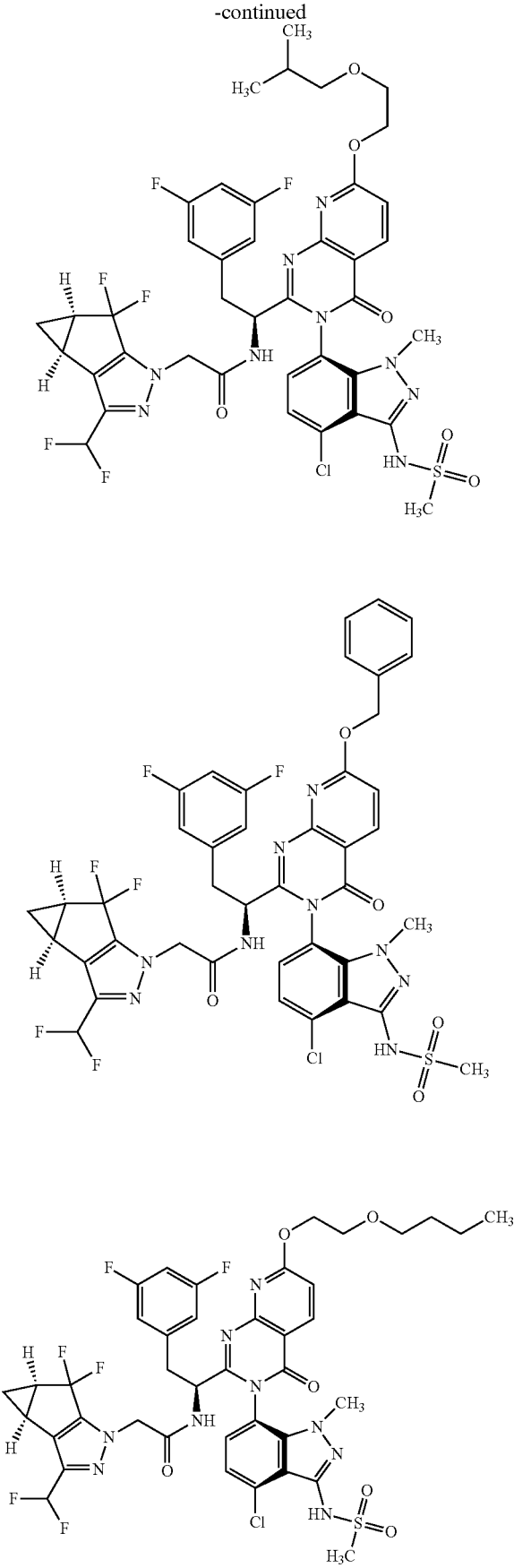

94
-continued

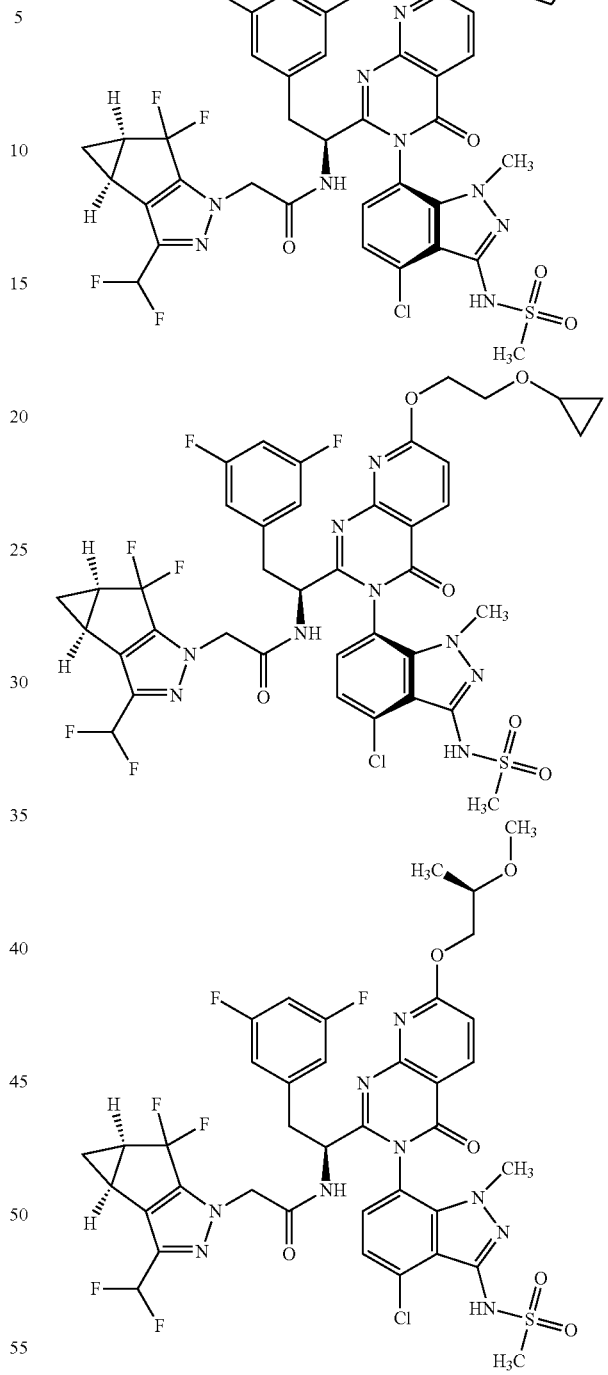

and pharmaceutically acceptable salts thereof.

17. A pharmaceutical composition comprising a compound or salt according to claim 1.

18. A composition according to claim 17 further comprising a pharmaceutically acceptable carrier, excipient, and/or diluent.

19. A method of treating HIV infection comprising administering a composition according to claim 13 to a patient.

20. The method of claim 19 wherein said administration is oral.

21. The method of claim 19 wherein said administration comprises administering by injection intramuscularly.

22. The method of claim 19 wherein said administration comprises administering by injection subcutaneously.

23. The method of claim 19 wherein said method further comprises administration of at least one other agent used for treatment of AIDS or HIV infection.

24. The method of claim 23 wherein the other agent or agents is selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors.

25. The method of claim 24 wherein said at least one other agent is selected from the group consisting of FTC, ibalizumab, PRO-140, dolutegravir, cabotegravir, fostemsavir, abacavir, lamivudine, fosamprenavir, rilpivirine, atazanavir, darunavir, MK-8718, MK-8591, tenofovir alfenamide, and bictegravir.

* * * * *